United States Patent
Li et al.

(10) Patent No.: US 9,529,974 B2
(45) Date of Patent: Dec. 27, 2016

(54) SYSTEM AND METHOD FOR DETECTING, COLLECTING, ANALYZING, AND COMMUNICATING EVENT-RELATED INFORMATION

(75) Inventors: Peter C. Li, McLean, VA (US); Jeffrey R. Collmann, Washington, DC (US); Jane W. Blake, Alexandria, VA (US); Mark G. Polyak, Alexandria, VA (US); James M. Wilson, Cedaredge, CO (US); Jae I. Yoon, Centreville, VA (US); Manabu Torii, Newark, DE (US); Carla S. Thomas, Bodega Bay, CA (US)

(73) Assignee: Georgetown University, Washington, DC (US)

( * ) Notice: Subject to any disclaimer, the term of this patent is extended or adjusted under 35 U.S.C. 154(b) by 887 days.

(21) Appl. No.: 13/192,160

(22) Filed: Jul. 27, 2011
(Under 37 CFR 1.47)

(65) Prior Publication Data

US 2012/0197896 A1    Aug. 2, 2012

Related U.S. Application Data

(63) Continuation-in-part of application No. 12/230,397, filed on Aug. 28, 2008.
(Continued)

(51) Int. Cl.
    *G06F 15/16* (2006.01)
    *G06F 19/00* (2011.01)
    (Continued)

(52) U.S. Cl.
    CPC ..... *G06F 19/3493* (2013.01); *G06F 17/30616* (2013.01); *G06Q 10/04* (2013.01);
    (Continued)

(58) Field of Classification Search
    CPC .......... G06F 19/3493; G06F 17/30616; G06Q 10/0631; G06Q 10/08; G06Q 10/067; G06Q 10/04; G06Q 10/06; G06Q 10/10; G06Q 50/22; G06Q 50/26; H04L 67/42
    (Continued)

(56) References Cited

U.S. PATENT DOCUMENTS

| 4,224,669 A | 9/1980 | Brame |
| 5,659,732 A | 8/1997 | Kirsch |

(Continued)

FOREIGN PATENT DOCUMENTS

| WO | 0137097 A1 | 5/2001 |
| WO | 02/19246 A2 | 3/2002 |
| WO | 2008/013553 A2 | 1/2008 |

OTHER PUBLICATIONS

Coleman, "Community Disorganization," Contemporary Social Problems, 1966, pp. 670-722, Harcourt, Brace & World, Inc., New York, NY, USA.

(Continued)

*Primary Examiner* — Zarni Maung
(74) *Attorney, Agent, or Firm* — Blank Rome LLP; Michael C. Greenbaum; Jonathan R. King

(57) ABSTRACT

A system and method involves detecting operational social disruptive events on a global scale, assigning event staging and warnings to express data in more simplistic terms, modeling data in conjunction with linguistics analysis to establish responsive actions, generating visualization and modeling capabilities for communicating information, and modeling propagation of events for containment and forecasting purposes.

24 Claims, 39 Drawing Sheets

Related U.S. Application Data

(60) Provisional application No. 61/368,054, filed on Jul. 27, 2010, provisional application No. 61/064,256, filed on Feb. 25, 2008, provisional application No. 61/046,275, filed on Apr. 18, 2008, provisional application No. 61/077,713, filed on Jul. 2, 2008.

(51) Int. Cl.
| | | |
|---|---|---|
| *H04L 29/08* | (2006.01) | |
| *G06F 17/30* | (2006.01) | |
| *G06Q 10/04* | (2012.01) | |
| *G06Q 50/22* | (2012.01) | |
| *G06Q 50/26* | (2012.01) | |
| *G06F 12/00* | (2006.01) | |

(52) U.S. Cl.
CPC ............ *G06Q 50/22* (2013.01); *G06Q 50/26* (2013.01); *H04L 29/08072* (2013.01)

(58) Field of Classification Search
USPC ............... 709/203, 217–219, 223–229, 250
See application file for complete search history.

(56) References Cited

U.S. PATENT DOCUMENTS

| | | |
|---|---|---|
| 5,748,954 A | 5/1998 | Mauldin |
| 5,924,090 A | 7/1999 | Krellenstein |
| 6,112,203 A | 8/2000 | Bharat et al. |
| 6,710,711 B2 | 3/2004 | Berry |
| 6,842,737 B1 | 1/2005 | Stiles et al. |
| 7,024,370 B2 | 4/2006 | Epler et al. |
| 7,146,358 B1 | 12/2006 | Gravano et al. |
| 7,146,361 B2 | 12/2006 | Broder et al. |
| 7,266,484 B2 | 9/2007 | Lombardo et al. |
| 7,269,568 B2 | 9/2007 | Stiles et al. |
| 7,343,302 B2 | 3/2008 | Aratow et al. |
| 7,343,303 B2 | 3/2008 | Meyer et al. |
| 7,346,492 B2 | 3/2008 | Shaw |
| 7,356,461 B1 | 4/2008 | Tremblay et al. |
| 7,373,524 B2 | 5/2008 | Motsinger et al. |
| 7,698,246 B2 | 4/2010 | Friedlander et al. |
| 7,725,565 B2* | 5/2010 | Li .................... G06Q 10/067 709/219 |
| 8,799,113 B2* | 8/2014 | Markham et al. ............. 705/29 |
| 2002/0005935 A1 | 1/2002 | Robin |
| 2002/0128925 A1 | 9/2002 | Angeles |
| 2002/0143469 A1 | 10/2002 | Alexander et al. |
| 2002/0193967 A1 | 12/2002 | Siegel |
| 2003/0084349 A1 | 5/2003 | Friedrichs et al. |
| 2003/0093580 A1 | 5/2003 | Thomas et al. |
| 2003/0129578 A1 | 7/2003 | Mault |
| 2003/0130873 A1 | 7/2003 | Nevin et al. |
| 2003/0163351 A1 | 8/2003 | Brown et al. |
| 2003/0177038 A1 | 9/2003 | Rao |
| 2004/0034288 A1 | 2/2004 | Hennessy et al. |
| 2004/0073459 A1 | 4/2004 | Barthell |
| 2004/0078146 A1 | 4/2004 | Lombardo et al. |
| 2004/0089156 A1 | 5/2004 | Gartstein et al. |
| 2004/0093331 A1 | 5/2004 | Garner et al. |
| 2004/0111399 A1 | 6/2004 | Rice |
| 2004/0122703 A1* | 6/2004 | Walker .................. G06F 19/325 705/2 |
| 2004/0122709 A1* | 6/2004 | Avinash ................ G06F 19/322 705/2 |
| 2005/0004835 A1 | 1/2005 | Roslansky et al. |
| 2005/0055308 A1 | 3/2005 | Meyer et al. |
| 2005/0071741 A1 | 3/2005 | Acharya et al. |
| 2005/0086088 A1 | 4/2005 | Stiles et al. |
| 2005/0102259 A1 | 5/2005 | Kapur |
| 2005/0182722 A1 | 8/2005 | Meyer et al. |
| 2005/0188423 A1 | 8/2005 | Motsinger et al. |
| 2006/0036619 A1 | 2/2006 | Fuerst |
| 2006/0054092 A1* | 3/2006 | Valencia et al. ............ 119/51.02 |
| 2006/0155581 A1 | 7/2006 | Eisenberger et al. |
| 2006/0161392 A1 | 7/2006 | Sholl et al. |
| 2006/0178910 A1 | 8/2006 | Eisenberger et al. |
| 2006/0185605 A1 | 8/2006 | Renz et al. |
| 2006/0224409 A1 | 10/2006 | Leininger et al. |
| 2006/0229822 A1 | 10/2006 | Theobald et al. |
| 2006/0230071 A1 | 10/2006 | Kass et al. |
| 2006/0241874 A1 | 10/2006 | Carter |
| 2006/0253477 A1 | 11/2006 | Maranhao |
| 2007/0016439 A1 | 1/2007 | Stiles et al. |
| 2007/0038587 A1 | 2/2007 | Watanabe et al. |
| 2007/0228145 A1 | 10/2007 | Diemer |
| 2008/0027749 A1 | 1/2008 | Meyer et al. |
| 2008/0115221 A1 | 5/2008 | Yun et al. |
| 2008/0140348 A1 | 6/2008 | Frank |
| 2008/0172352 A1 | 7/2008 | Friedlander et al. |
| 2008/0175266 A1 | 7/2008 | Alperovitch et al. |
| 2008/0202445 A1* | 8/2008 | Rugg ............................ 119/712 |
| 2008/0306768 A1 | 12/2008 | Fotsch et al. |
| 2008/0319942 A1 | 12/2008 | Courdy et al. |
| 2009/0006311 A1 | 1/2009 | Ting et al. |
| 2009/0010842 A1 | 1/2009 | O'Brien et al. |
| 2009/0151644 A1* | 6/2009 | Valencia et al. ............ 119/51.02 |
| 2009/0216747 A1* | 8/2009 | Li ......................... G06Q 10/067 |
| 2009/0216860 A1* | 8/2009 | Li et al. ........................ 709/219 |
| 2009/0319295 A1 | 12/2009 | Kass-Hout et al. |
| 2010/0066540 A1 | 3/2010 | Theobald et al. |
| 2010/0175006 A1* | 7/2010 | Li ................................. 715/764 |

OTHER PUBLICATIONS

Rosenthal, et al., "The World of Crises and Crisis Management," Coping with Crises: The Management of Disasters, Riots and Terrorism, 1989, pp. 3-33, Charles C. Thomas, Springfield, IL, USA.

Madoff, et al., "The Internet and the Global Monitoring of Emerging Diseases: Lessons from the First 10 Years of ProMED-Mail," Archives of Medical Research, Nov.-Dec. 2005, pp. 724-730, vol. 36, No. 6, Elsevier Inc., Maryland Heights, MO, USA.

Turell, "Effect of Environmental Temperature on the Vector Competence of Aedes fowlri for Rift Valley Fever Virus," Research in Virology, Mar.-Apr. 1989, pp. 147-154, vol. 140, No. 2, Elsevier, Paris, France.

Rossi, et al., "Characterization of Attenuated Strains of Rift Valley Fever Virus," Journal of General Virology, Apr. 1988, pp. 817-823, vol. 69, pt. 4, Great Britain.

Hardy, et al., "Effect of Rearing Temperature on Transovarial Tranmission of St. Louis Encephalitis Virus on Mosquitos," American Journal of Tropical Medicine and Hygiene, Sep. 1980, pp. 963-968, vol. 29, No. 5, Deerfield, IL, USA.

Dohm, et. al., "Effect of Environmental Temperature on the Ability of Culex pipiens (Diptera: Culicidae) to Transmit West Nile Virus," Journal of Medical Entomology, Jan. 2002, pp. 221-225, vol. 39, No. 1, Lanham, MD, USA.

Turell, et al., "Effect of Holding Conditions on the Detection of West Nile Viral RNA by Reverse Transcriptase-Polymerase Chain Reaction from Mosquito (Diptera: Culicidae) Pools," Journal of Medical Entomology, Jan. 2002, pp. 1-3, vol. 39, No. 1, Lanham, MD, USA.

Dohm, et al., "Effect of Incubation at Overwintering Temperatures on the Replication of West Nile Virus in New York Culex pipiens (Diptera: Culicidae)," Journal of Medical Entomology, May 2001, pp. 462-464, vol. 38, No. 3, Lanham, MD, USA.

Brubaker, et al., "Effect of Environmental Temperature on the Susceptibility of Culex pipiens (Diptera: Culicidae) to Rift Valley Fever Virus," Journal of Medical Entomology, Nov. 1998, pp. 918-921, vol. 35, No. 6, Lanham, MD, USA.

Symanzik, et al., "Visualizing the Spread of West Nile Virus," Joint Statistical Meetings—Section on Statistical Graphics, 2003, pp. 4178-4188, San Francisco, CA, USA.

Wilson, "Use of Remote Sensing in Integrated Biodefense," 30th Annual International Symposium on Remote Sensing and Environment, Nov. 2003, pp. 264-267, Washington, DC, USA.

Campbell, "Traditional Indications and Warnings for Host Based Intrusion Detection," CERT Conference, 1999, 38 pp., Litton PRC, Inc., McLean, VA, USA.

(56) References Cited

OTHER PUBLICATIONS

Davis, "A Watchman for All Seasons," Central Intelligence Agency, Jul. 1996, 6 pp., Washington, DC.
Prince, "Catastrophe and Social Change," 1920, 153 pp., New York, NY, USA.
Wilson, "Bioalert: Disease Knows No Borders, Prevention is Key," Forum, Georgetown Journal of International Affairs, Summer/Fall 2001, pp. 3-14, Washington, DC, USA.
Sweeney, "The Struggle for a New Internationalism," Georgetown Journal of International Affairs, Winter/Spring 2001, pp. 5-14, Washington, DC, USA.
Wilson, et al., "Prospectus: Use of Remote Sensing in Epidemic Surveillance and Response," date unknown, 12 pp., Washington, DC and Greenbelt, MD, USA.
Lehner, et al., "Automated Detection of Social Disruption Related to Disease Outbreaks: An Empirical Test," date unknown, 17 pp., The Mitre Corporation, Washington, DC, USA.
Mykhalovskiy, et al., "The Global Public Health Intelligence Network and Early Warning Outbreak Detection," Revue Canadienne de Sante Publique, Jan.-Feb. 2006, pp. 42-44, vol. 97, No. 1, Ottawa, Ontario, Canada.
Collman, "Towards a Doctrine of Biosurveillance: A Case Study," Department of Radiology, Georgetown University, date unknown, 1 p., Washington, DC, USA.
Polyak, "Retrospective Analyses Demonstrate the Presence of 'Indications and Warnings' Leading Up to Bioevents," Department of Radiology Imaging Science and Information Systems (ISIS) Center, date unkown, 1 p., Washington, DC, USA.
Blake, et al., "Anatomy of a Bioevent: Venezuelan Equine Encephalitis 1995," ISIS Center, 1995, 1 p., Washington, DC, USA.
Wilson, "Project Argus: A National Biodefense Priming System," Division of Integrated Biodefense, ISIS Center, date unknown, 1 p., Washington, DC, USA.
Wilson, "Indications and Warnings to Detect and Track Biological Events," AROC Argus Research Operations Center, date unknown, 16 pp., Georgetown University, Washington, DC, USA.
Wilson, "Use of Satellite Imagery for Epidemic Surveillance and Response," Department of Pediatrics, Georgetown University Hospital, date unknown, 4 pp., Washington, DC, USA.
Pinzon, et al., "Trigger Events: Enviroclimatic Coupling of Ebola Hemorrhagic Fever Outbreaks," American Journal of Tropical Medicine and Hygiene, 2004, pp. 664-674, vol. 71, No. 5, The American Society of Tropical Medicine and Hygiene, Deerfield, IL, USA.
Parker, et al., "Proceedings from The Consensus Conference on the Role of Biosensors in the Detection of Agents of Bioterrorism," TATRC Telemedic & Advanced Technology Research Center, Sep. 2003, cover page and pp. 1-15, U.S. Army Medical Research and Material Command, Fort Detrick, MD, USA.
De Groeve, "Global Disaster Alert and Coordination System for More Effective and Efficient Humanitarian Response," TIEMS Conference, Jun. 2006, 31. pp., European Commission, Directorate-General, Joint Research Centre, Brussels, Belgium.
Wilson, et al., "Proceedings from the Integrated Research Team Workshop on the Role of Indications and Warnings for Prediction and Surveillance of Catastrophic Biological Events," TATRC Telemedicine & Advanced Technology Research Center, Jun. 2004, cover page and pp. 1-15, Fort Detrick, MD, USA.
Collmann, et al., "Designing Ethical Practice in Biosurveillance: The Project Argus Doctrine," date unknown, pp. 1-26, O'Neill Institute for National and Global Health Law, School of Nursing and Health Studies, Georgetown University Medical Center, Washington, DC, USA.
McGrath, "Biological Impact of Social Disruption Resulting From Epidemic Disease," American Journal of Physical Anthropology, 1991, vol. 84, pp. 407-419, John Wiley & Sons, Inc., Hoboken, NJ, USA.
Wilson, et al., "A Heuristic Indication and Warning Staging Model for Detection and Assessment of Biological Events," Journal of the American Medical Informatics Association, 2008, pp. 158-171, vol. 15, American Medical Informatics Association, Bethesda, MD, USA.
Chute, "Biosurveillance, Classification, and Semantic Health Technologies," Journal of the American Medical Informatics Association, 2008, pp. 172-173, vol. 15, American Medical Informatics Association, Bethesda, MD, USA.
Damianos, et al., "MiTAP for Biosecurity: A Case Study," American Association for Artificial Intelligence, 2002, pp. 13-29, Menlo Park, CA, USA.
Damianos, et al., "MiTAP, Text and Audio Processing for Bio-Security: A Case Study," American Association for Artificial Intelligence, 2002, pp. 807-814, Menlo Park, CA, USA.
Damianos, et al., "The MiTAP System for Monitoring Reports of Disease Outbreak," date unknown, 12 pp., The MITRE Corporation, Bedford, MA, USA.
Beck, et al., "Remote Sensing and Human Health: New Sensors and New Opportunities," Emerging Infectious Diseases, May-Jun. 2000, pp. 217-226, vol. 6, No. 3, Centers for Disease Control, Atlanta, GA, USA.
Horimoto, et al., "Influenza: Lessons from Past Pandemics, Warnings from Current Incidents," Nature Reviews Microbiology, Aug. 2005, pp. 591-600, vol. 3, Nature Publishing Group, New York, NY, USA.
Reingold, "If Syndromic Surveillance is the Answer, What is the Question?" Biosecurity and Bioterrorism: Biodefense Strategy, Practice, and Science, 2003, pp. 77-81, vol. 1, No. 2, Mary Ann Liebert, Inc., New Rochelle, NY, USA.
Buehler, et al., "Syndromic Surveillance and Bioterrorism-related Epidemics," Emerging Infectious Diseases, Oct. 2003, pp. 1197-1204, vol. 9, No. 10, Centers for Disease Control, Atlanta, GA, USA.
Linthicum, et al., "Climate and Satellite Indicators to Forecast Rift Valley Fever Epidemics in Kenya," Science Magazine, Jul. 1999, pp. 397-400, vol. 285, Washington, DC, USA.
Raloff, "How Climate Perturbations Can Plague Us," Science News, Sep. 1995, pp. 196-197, vol. 148, No. 13, Society for Science & the Public, Washington, DC, USA.
Harris, "Papanicolaou Smear Recommendations, Patient Complaints, and Patient Satisfaction in Managed-Care Medical Organizations," Medical Care, Mar. 1995, pp. 272-279, vol. 33, No. 3, Lippincott Williams & Wilkins, Philadelphia, PA, USA.
Corrigan, "How Do Purchasers Develop and Use Performance Measures?" Medical Care, Jan. 1995, pp. 18-24, Lippincott Williams & Wilkins, Philadelphia, PA, USA.
Brownstein, et al., "Surveillance Sans Frontieres: Internet-Based Emerging Infectious Disease Intelligence and the HealthMap Project," PLoS Medicine, 2008, pp. 1-19, Public Library of Science, San Francisco, CA, USA.
Freifeld, et al., "HealthMap: Global Infectios Disease Monitoring through Automated Classification and Visualization of Internet Media Reports," Children's Hospital Informatics Program at the Harvard-MIT Division of Health Sciences and Technology, Feb. 2008, 3 pp., Boston, MA, USA.
Kawazoe, "The Development of a Schema for the Annotation of Terms in the BioCaster Disease Detecting/Tracking System," KR-MED 2006, "Biomedical Ontology in Action," Nov. 2006, pp. 77-85, American Medical Informatics Association, Baltimore, MD, USA.
Stein, "SARS Shows WHO Disease Hunters' Skills, and Limits," The Washington Post, May 2003, 4 pp., Washington, DC, USA.
Author Unknown, "A Shot of Transparency," The Economist, Aug. 2006, 3 pp., St. Louis, MO, USA.
Lin, et al., "S'pore Unveils Intelligent Risk Warning System," The Straits Times, Mar. 2007, 3 pp., News Centre, Singapore.
Gray, "Medisys Just What the Doctor Ordered," The Gazette, Jun. 1992, 4 pp., Montreal, Quebec, Canada.
Dorsey, "Medisys Targets U.S.," The Herald, Aug. 1997, 2 pp., Glasgow, Scotland.
Cash, et al., "Impediments to Global Surveillance of Infectious Diseases: Consequences of Open Reporting in a Global Economy," Bulletin of the World Health Organization, 2000, pp. 1358-1367, vol. 78, World Health Organization, Geneva, Switzerland.

(56) References Cited

OTHER PUBLICATIONS

Author Unknown, "Public Health Agency of Canada (PHAC)—PHAC Monitors Global Health with the Help of Nstein Technologies and Microsoft," Aug. 2005, 5 pp.
Li, "Real-Time Event Driven Architecture for Activity Monitoring and Early Warning," 2005, 4 pp., IEEE, Washington, DC, USA.
Morse, "Global Infectious Disease Surveillance and Health Intelligence," Health Affairs, Jul./Aug. 2007, pp. 1069-1077, vol. 26, No. 4, Bethesda, MD, USA.
Barton, "Communities in Disaster: A Sociological Analysis of Collective Stress Situations," 1969, Doubleday Anchor, New York, NY, USA. (This citation refers to a book, which is available upon request.)
Strauss, et al., "Basics of Qualitative Research: Grounded Theory Procedures and Techniques," 1990, SAGE Publications, Inc., Newbury Park, CA, USA. (This citation refers to a book, which is available upon request.).
Author Unknown, "Headlines," The American Journal of Nursing, Aug. 1993, p. 9, vol. 93, No. 8, Lippincott Williams & Wilkins, Philadelphia, PA, USA.
Buehler, et al., "Syndromic Surveillance," Emerging Infectious Diseases, Jul. 2004, pp. 1333-1335, vol. 10, No. 7, Centers for Disease Control, Atlanta, GA, USA.
Schoenbaum, "Health Care Reform and Its Implications for Quality of Care," Medical Care, Jan. 1995, pp. 37-40, vol. 33, No. 1, Lippincott Williams & Wilkins, Philadelphia, PA, USA.
Author Unknown, "Protecting the Nation's Health in an Era of Globalization: CDC's Global Infectious Disease Strategy," Department of Health and Human Services, Centers for Disease Control and Prevention, 2002, cover page and pp. 3-72, Atlanta, GA, USA.
Thomson, et al., "Satellite Mapping of Loa Loa Prevalence in Relation to Ivermectin Use in West and Central Africa," The Lancet, Sep. 2000, 3 pp., vol. 356, No. 9235, Elsevier, Maryland Heights, MO, USA.
Pinzon, et al., "Climate-Based Health Monitoring Systems for Eco-Climatic Conditions Associated with Infectious Diseases," Bulletin de la Societe de Pathologie Exotique, Sep. 2005, pp. 239-243, vol. 98, No. 3, Paris, France.
Turell, et al., "Mechanical Transmission of Bacillus anthracis by Stable Flies (Stomoxys calcitrans) and Mosquitos (Aedes aegypti and Aedestaeniortiynchus)," Infection and Immunity, Aug. 1987, pp. 1859-1861, vol. 55, No. 8, Washington, DC, USA.
Turell, "Effect of Environmental Temperature on the Vector Competence of Aedes taeniorhynchus for Rift Valley Fever and Venezuelan Equine Encephalitis Viruses," American Journal of Tropical Medicine and Hygiene, Dec. 1993, pp. 672-676, vol. 49, No. 6, Deerfield, IL, USA.
Turell, et al., "Protection of Hamsters by Venezuelan Equine Encephalitis Virus Candidate Vaccine V3526 Against Lethal Challenge by Mosquito Bite and Intraperitoneal Injection," American Journal of Tropical Medicine and Hygiene, Feb. 2008, pp. 328-332, vol. 78, No. 2, Deerfield, IL, USA.
Turell, et al., "Effect of Environmental Temperature on the Vector Competence of Aedes aegypti and Ae. taeniorhynchus for Ockelbo Virus," American Journal of Tropical Medicine and Hygiene, Nov. 1990, pp. 543-550, vol. 43, No. 5, Deerfield, IL, USA.
Turell, et al., "Increased Mosquito Feeding on Rift Valley Fever Virus-Infected Lambs," American Journal of Tropical Medicine and Hygiene, Nov. 1984, pp. 1232-1238, vol. 33, No. 6, Deerfield, IL, USA.
Turell, et al., "Transovarial and Trans-Stadial Transmission of California Encephalitis Virus in Aedes dorsalis and Aedes melanimon, "American Journal of Tropical Medicine and Hygiene, Sep. 1982, pp. 1021-1029, vol. 31, No. 5, Deerfield, IL, USA.
Agarwal, et al., "Monitoring Massive Streams Simultaneously: A Holistic Framework for Integrated Biosurveillance," date unknown, 21 pp.
Author Unknown "Intelligence Analysis Management," Wikipedia, accessed on Dec. 12, 2009, pp. 1-14, at http://en.wikipedia.org/wiki/Intelligence_analysis_management.
Author Unknown, "Alerts—Disease Information," OIE World Animal Health Information Database website, accessed on Dec. 12, 2009, 2 p. at http://www.oie.int/eng/.
Author Unknown, "Current Disaster Events," Global Disaster Alert and Coordination System website, accessed on Dec. 16, 2009, 3 pp., at http://www.gdacs.org/.
Author Unknown, "Disaster Management Floods in Asia," International Federation of Red Cross and Red Crescent Societies website, accessed on Dec. 12, 2009, 3 pp., at http://www.ifrc.org/what/disasters/response/sasia_floods.asp.
Author Unknown, "Diseases and Conditions," Centers for Disease Control and Prevention website, accessed on Dec. 12, 2009, 2 pp., at http://www.cdc.gov/DiseasesConditions/.
Author Unknown, "Fujita Tornado Damage Scale," accessed on Feb. 17, 2010, 1 p., at www.spc.noaa.gov/faq/tornado/f-scale.html.
Author Unknown, "Global Disaster Alert and Coordination System," IPSC Institute for the Protection and Security of the Citizen, date unknown, 2 pp., European Commission, Directorate-General, Joint Research Centre, Brussels, Belgium.
Author Unknown, "Global Disaster Alert Coordination System," GDACS, accessed on Mar. 8, 2010, 5 pp., GDACS Secretariat, Geneva, Switzerland.
Author Unknown, "Global Health Monitor," BioCaster Global Health Monitor, accessed on Mar. 8, 2010, 1 p., National Institute of Informatics, Tokyo, Japan.
Author Unknown, "Global Infectious Disease Surveillance and Detection: Assessing the Challenges—Finding Solutions, Workshop Summary," 2007, 2 pp., at http://www.nap.edu/openbook.php?record_id=11996&page=20.
Author Unknown, "Global Public Health Intelligence Network (GPHIN)," Public Health Agency of Canada, Nov. 2004, 2 pp., at http://www.phac_aspc.gc.Ca/medialnr_rp/2004/200&..9phin-rmisPbk-eflg.PhP.
Author Unknown, "Health Topics," WHO website, accessed on Dec. 12, 2009, 13 pp., at http://www.who.int/topicslen/.
Author Unknown, "HealthMap Global Disease Alert Map," HealthMap website, accessed on Dec. 16, 2009, 12 pp., at http://www.healthmap.org/en.
Author Unknown, "iJEt Intelligent Risk Systems," IJET website, accessed on Dec. 16, 2009, 1 p., at http://www.ijet.com/index.asp.
Author Unknown, "Instructions for Ordering USAMRIID Reference Materials," U.S. Army Medical Research Institute of Infectious Diseases website, accessed on Dec. 12, 2009, 4 PP., at http://www.usamriid.arrny.mil/education/instruct.htm.
Author Unknown, "International Health Regulations FAQs," Centers for Disease Control and Prevention website, accessed on Dec. 12, 2009, 8 pp., at http://origin2.cdc.govfglobalhealth/ihrMaterial/IHRFaq.htm#ihr.
Author Unknown, "International Health Regulations," WHO website, accessed on Dec. 12, 2009, 2 pp., at http://www.who.int/topics/intemational_health_regulations/en/.
Author Unknown, "Medisys Inc. Reports Earnings for Qtr to Jun. 30," The New York Times, Aug. 15, 1991, p. 6, section D, col. 1.
Author Unknown, "Nationally Notifiable Infectious Diseases," Centers for Disease Control and Prevention website, accessed on Dec. 12, 2009, 2 pp., at http://www.cdc.gov/ncphi/disss/nndss/phslinfdis.htm.
Author Unknown, "Nstein Connecting People with Content," Nstein website, accessed on Dec. 12, 2009, 6 pp., at hftp://www.nstein.com/en/index.php.
Author Unknown, "Political and Security Risk Analysis," Control Risks website, accessed on Dec. 12, 2009, 2 pp., at http://www.controlrisks.com/.
Author Unknown, "ProMED-mail," ProMED-mail website, accessed on Dec. 16, 2009, 2 pp., at http://www.promedmail.org/pls/otn/f?p=2400;1000.
Author Unknown, "STRATFOR Global Intelligence," STRATFOR website, accessed on Dec. 12, 2009, 3 pp., at http://www.stratfor.com/.
Author Unknown, "The Saffir-Simpson Hurricane Wind Scale (Experimental)," National Weather Service website, accessed on Dec. 12, 2009, 3 pp., at http://www.nhc.noaa.gov/aboutsshs.shtml.

(56) References Cited

OTHER PUBLICATIONS

Author Unknown, "United Nations Climate Change Conference," Relief Web website, accessed on Dec. 12, 2009, 3 pp., at http://www.reliefweb.intlrw/dbc.nsf/.

Author Unknown, "WAHID Interface," OIE World Animal Health Information Database website, accessed on Dec. 12, 2009, 1 p., at http://www.oie.intlwahislpublic.php?page=home.

Author Unknown, "Welcome to Shoreland," Shoreland website, accessed on Dec. 12, 2009, 1 p., at http:llwww.shoreland.com/.

Author Unknown, "Worldwide Reach Human Touch," International SOS website, accessed on Dec. 12, 2009, 2 pp., at http://www.intemationalsos.com/en/.

Brownstein, et al, "HealthMap: The Development of Automated Real-Time Internet Surveillance for Epidemic Intelligence," Eurosurveillance, Nov. 2007, pp. 1-4, vol. 12, issue 48, Stockholm, Sweden.

Carr, "Disaster and the Sequence-Pattern Concept of Social Change," The American Journal of Sociology, 1932, pp. 207-218, vol. 38, No. 2, Chicago, IL, USA.

Chase, et al., "The Specter of Infection," Environmental Health Perspectives, Jul. 1996, pp. 694-699, vol. 104, No. 7, The National Institute of Environmental Health Sciences (NIEHS), Triangle Park, NC, USA.

Damianos, et al., "MiTAP: A Case Study of Integrated Knowledge Discovery Tools," Proceedings of the 36th Hawaii International Conference on System Sciences, 2002, 10 pp., IEEE Computer Society, Washington, DC, USA.

Damianos, et at., "MiTAP for Real Users, Real Data, Real Problems," 2003, pp. 656-657, CHI 2003: New Horizons, Ft. Lauderdale, FL, USA.

Doan, et al., "Global Health Monitor—A Web-based System for Detecting and Mapping Infectious Diseases," date unknown, 6 pp., National Institute of Informatics, Tokyo, Japan.

Hartley, et al., "Indications and Warnings of Infectious Disease: A Public Health Tool for the 21st Century," date unknown, pp. 1-16, Baltimore, MD, USA.

Lehner, et al., "An Application of Document Filtering in an Operational System," Information Processing and Management, 2010, pp. 611-627, vol. 46, Elsevier, Maryland Heights, MO, USA.

Lehner, et al., "An Empirical Test of the Use of Social Disruption as an Early Indicator of Biological Outbreaks," Journal Intelligence Community Research and Development, date unknown, pages unknown.

Lehner, et al., "Document Filtering in an Operational System," date unknown, pp. 1-19, The Mitre Corporation, McLean, VA, USA.

Lundstrom, et al., "Effect of Environmental Temperature on the Vector Competence of Culex pipiens and Cx. torrentium for Ockelbo Viruses," American Journal of Tropical Medicine and Hygiene, Nov. 1990, pp. 534-542, vol. 43, No. 5, Deerfield, IL, USA.

Menezes, "Going Global: GPHIN2 Gains International Recognition," CIO Government Review, Jan. 2005, pp. 1-3, IDG Global Solutions, Staines, Middlesex, United Kingdom.

O'Guinn, et al., "Effect of Triethylamine on the Recovery of Selected South American Alphaviruses, Flaviviruses and Bunyaviruses from Mosquito (Diptera: Culicidae) Pools," Journal of Medical Entomology, Sep. 2002, pp. 806-808, vol. 39, No. 5, Lanham, MD, USA.

Polyak, et al., "Anthrax in Sverdlovsk, U.S.S.R., Apr.-Jun. 1979: A Case Study in Examining Open-Source Media for Indications and Warnings of an Accidental Biological Weapons Release," date unknown, pp. 1-17, Washington, DC, USA.

Stallings, "Disaster and the Theory of Social Order," What is Disaster? Perspectives on the Question, 1998, pp. 127-145, Routledge, New York, NY, USA.

Tucker, et at., "Climatic and Ecological Context of the 1994-1996 Ebola Outbreaks," Photogrammetric Engineering & Remote Sensing, Feb. 2002, pp. 147-152, vol. 68, No. 2, American Society for Photogrammetry and Remote Sensing, Bethesda, MD, USA.

Turell, et al., "Effect of Extrinsic Incubation Temperature on the Ability of Aedes taeniorhynchus and Culex pipiens to Transmit Rift Valley Fever Virus," American Journal of Tropical Medicine and Hygiene, Nov. 1985, pp. 1211-1218, vol. 34, No. 6, Deerfield, IL, USA.

Valleron, et al., "A Computer Network for the Surveillance of Communicable Diseases: The French Experiment," American Journal of Public Health, Nov. 1986, pp. 1289-1292, vol. 76, No. 11, Washington, DC, USA.

Wilson, "Argus: A Global Detection and Tracking System for Biological Events," Advances in Disease Surveillance, 2007, 1 p., vol. 4, No. 21, Georgetown University Medical Center, Washington, DC.

Wilson, et al., "Anthrax in Zimbabwe, 1978-80: A Case Study in Assessing the Causes of a Biological Event," date unknown, 30 pp., Washington, DC, USA.

Wilson, et al., "Biosurveillance Tradecraft," Wiley Handbook of Science and Technology for Homeland Security, 2008, pp. 1-19, John Wiley & Sons, Inc., Hoboken, NJ, USA.

Winchester, "The Frequency of Biological Events Relevant to National Security is Increasing, and Current Disease Surveillance Systems in the United States (U.S.) Have Been Unable to Detect These Events in a Timely Fashion. The Danger to the U.S. Spans Human, Animal, and Plant Infectious Disease," Department of Radiology, Imaging Science and Information Systems (ISIS) Center, date unknown, 1 p., Washington, DC, USA.

Woodall, "Stalking the Next Epidemic: ProMED Tracks Emerging Diseases," Public Health Reports, Jan.-Feb. 1997, pp. 78-82, Association of Schools of Public Health, Washington, DC, USA.

Woodall, et al., "ProMED-Mail: Background and Purpose," Emerging Infectious Diseases, Jun. 2001, p. 563, vol. 7, No. 3, Rio de Janeiro, Brazil and Fort Collins, CO, USA.

Author Unknown, "Summary of the Indications and Warnings of Social Disruption that are Associated with VEE, RVF and SARS," (Table 2), released to JAMIA in Mar. of 2008.

Georgetown University/The Mitre Corp., "Project Argus, Capabilities Specification Document Version 1.0," Aug. 2005.

Li, et al., "Watch Board v2.0," Dec. 15, 2005, Division of Integrated BioDefence, ISIS Center.

Li, et al., "Argus Watchboard Requirement Analysis, A Global Argus Sub-System Specification, Division of Integrated BioDefence," Jun. 2006, ISIS Center, Georgetown University Medical Center.

Author Unknown, "Prospective Case Studies Conducted," (Table 3), released to JAMIA in Mar. of 2008.

Blake, et al., "Indications and Warnings of Rift Valley Fever in Kenya, 1997-1998," date unknown, pp. 1-41, Washington, DC, USA.

Blake, et al., "Venezuelan Equine Encephalitis: A Case Study in International Biological Threat Detection and Assessment," date unknown, pp. 1-21, Washington, DC, USA.

Polyak, at al., "Emergence of Severe Acute Respiratory Syndrome (SARS) in the People's Republic of China, 2002-2003; A Case Study to Define Requirements for Detection and Assessment of International Biological Threats," date unknown, pp. 1-46, Washington, DC, USA.

* cited by examiner

FIG. 9

Turkish Respiratory Disease

Listing 1 to 36 unique documents Elapsed search time: 1.776sec

Terms: HSN1 OR "kuş gribi" OR grip OR "soğuk hastalık" OR "soğuk hastalıkları" OR "soğuk hastalığı" OR influenza OR "Tavuk Vebası"

| Sources: | All Turkish sources |
| Dates: | last 2 days |
| Limits: | none |

| Pub Date | (#Duplicates) Subject | Source Name | Source Country |
|---|---|---|---|
| 2008-02-06 | İşte aşkın fotoğrafı | Sabah | TURKEY |
| 2008-02-06 | Türk arkeologlara "Şövalyelik Nişanı" | Sabah | TURKEY |
| 2008-02-06 | Kontrolsüz üretim ve haksız rekabet var | Yeni Asya | TURKEY |
| 2008-02-06 | Kuş gribi şimdi de Sakarya'da | Radikal | TURKEY |
| 2008-02-06 | Tehlikeli bulaşıcılar | Takvim | TURKEY |
| 2008-02-06 | Kuş gribi karantinası | Takvim | TURKEY |
| 2008-02-06 | Hep ilkleri gerçekleştiridik | Kıbrıs Gazetesi | CYPRUS |
| 2008-02-06 | Eksik çalıştılar | Yeni Safak | TURKEY |
| 2008-02-06 | Kanatlı hayvan itlafı başladı | Turk Medya | TURKEY |

Argus Watchboard™

Wild Fire Test Bed | Currently, there are 2 active Wild Fire Alert(s).

| | Home | Reports | Tools | Training | Administration |

Welcome, *cheeseman_S*

*cheeseman_S*, welcome to WatchBoard v3.2
Your last activity was logged at 2/6/2008 7:36:47 AM. (If this is incorrect, please contact the Admin)

Today's Regional Summary Report has not been submitted. — 2002
Write Report

[Country Report V2 Review]

| ID | Warning Lvl | Country | Title |
|---|---|---|---|
| 519 | Watch | PAKISTAN | Undiagnosed Animal Disease (Cattle), Bird Die-Off, H5N1 Avian In Undiagnosed Animal Disease (Goat) |

[Country Report for Review]

| UID | EID | Country | Province | Entity | Hst | ASt | Pst | Date |
|---|---|---|---|---|---|---|---|---|
| 53039 | 15912 | MARTINIQUE NOT A FIPS10 CODE_ | Martinique (general) | Dengue | hS2 | na | na | 2/6/2008 13:12:53 |
| 53043 | 23935 | TURKEY | Kocaeli | H5 Avian Influenza | na | na | na | 2/6/2008 13:15:49 |

Submitted for your Review

| UID | EID | Country | Province | Entity | Hst | ASt | Pst | Date |
|---|---|---|---|---|---|---|---|---|
| 53015 | 23935 | TURKEY | Kocaeli | H5 Avian Influenza | na | aS1 | na | 2/6/2008 9:11:43 AM |
| 53008 | 22522 | UNITED KINGDOM | Dorset | H5 Avian Influenza | hSP | aS1 | na | 2/6/2008 8:39:19 AM |
| 52997 | 23860 | BULGARIA | Razgrad | Respiratory Disease | hS2 | na | na | 2/6/2008 8:14:36 AM |
| 52995 | 23934 | TURKEY | Sakarya | H5 Avian Influenza | hS0 | aS1 | na | 2/6/2008 8:02:12 A |

-Biological Event Country Reports-

| Country | Title | Date |
|---|---|---|
| CZECH REPUBLIC | Respiratory Disease | 2/1/2008 |
| EGYPT | H5N1 Avian Influenza | 2/5/2008 |
| HONDURAS | Pox Disease | 2/1/2008 |
| INDONESIA | H5N1 Avian Influenza | 2/5/2008 |
| ZAMBIA | Suspected Drug Contamination (HIV) | 2/4/2008 |
| INDIA | Polio, H5N1 Avian Influenza, Bird Die-Off | 2/6/2008 |
| PAKISTAN | H5N1 Avian Influenza | 2/6/2008 |
| PARAGUAY | Yellow Fever | 2/6/2008 |
| ROMANIA | Respiratory Disease | 2/1/2008 |
| RUSSIA | Respiratory Disease | 2/6/2008 |
| SAUDI ARABIA | Undiagnosed Animal Die-off, H5N1 Avian Influenza, Animal Die-Off, Undiagnosed Animal Disease | 2/5/2008 |
| SOMALIA | Undiagnosed Human Disease | 1/31/2008 |
| SOUTH KOREA | Respiratory Disease | 1/31/2008 |
| SPAIN | Respiratory Disease | 2/5/2008 |
| THAILAND | Bird Die-Off, H5N1 Avian Influenza | 2/6/2008 |

FIG. 25

2600 — Argus Research Operations Center (AROC), Washington DC

The below information is obtained through publicly available local media based upon socio-economic factors associated with a local or regional biological event. The assessment of each event is based upon unidentified social, economic, and geographic indicators contained in local media sources and additional analysis by Argus regional experts. This overview consists of the most serious biological events identified over the past 7 days throughout the world and is meant to provide a summary of these occurrences. For in-depth reporting and assessment of these events, as well as other emerging incidents, please refer to the section entitled "Event Listing".

2602 — ☼ Basic Information
- Country: ALGERIA
- Warning Level: Watch
- Entity: Suspected H5N1 Avian Influenza, Undiagnosed Human Disease
- Type: Biological Alert Report
- Date: 9/17/2007 3:47:42 PM

2604 — ☼ Recent Country Report Highlights

| Date | Summary |
|---|---|
| 9/17/2007 | National news media continue to report on an undiagnosed human disease in Sidi Bel Abbes. |
| 9/17/2007 | International blog post suggesting H5N1 avian influenza as the possible etiology in Algeria. |

2606 — ☼ Current Alert Events

| Detail Info | Content |
|---|---|
| -SubTopic: Undiagnosed Human Disease<br>-Date: 9/17/2007 3:47:20 PM<br>-Source Overview: National<br>-Credibility: Medium<br>-Economic Impact: False | National news media continue to report on an undiagnosed human disease in Sidi Bel Abbes that has affected approximately 100 people since 20 August. Media reports have indicated disagreement among health officials on the cause of illness as well as conflicting accounts of disease confirmation status. To date, 98 people presented with nephritis and have been released from the hospital. Several media outlets have highlighted that this is the first appearance of acute nephritis [implied] related to the disease in Algeria. |
| | Since 11 September, Algerian media have reported an outbreak of tonsillitis affecting as many as 250 police and border agents in Bejaia. Diphtheria is considered the suspected cause, and symptoms described include fever, respiratory difficulties, sore throat (sometimes involving blocked airways), and stomachache. |
| -SubTopic: Suspected H5N1 Avian Influenza<br>-Date: 9/17/2007 3:46:05 PM<br>-Source Overview: National; International:<br>-Credibility: Low<br>-Economic Impact: False | The Algiers Pasteur Institute has confirmed tonsillitis, although they have not reported a specific etiological agent. On 14 September, however, an international blog posted one article on this outbreak with a title suggesting H5N1 avian influenza as the possible etiology. The report does not provide any other indication of the presence of the disease. |

2608 — Air-Traffic Data for ALGERIA (2005).

2610 — ☼ AROC Note

Concerning the disease outbreak in Bejaia, media reports to date indicate that patients have presented with symptoms of fever and sore throat and state that most health officials believe the outbreak to be diphtheria, though food poisoning has also been suggested. Moreover, we do not consider the blog referenced above to be a highly credible source. While it is AROC's assessment that the symptoms described may be attributed to diphtheria or another upper respiratory pathogen, in the absence of a confirmed diagnosis, we are posting this report for advisement purposes. Note that neither AROC nor the OIE has recorded current H5N1 avian influenza outbreaks in Algeria.

Concerning the disease outbreak in Sidi Bel Abbes, due to conflicting media reports, AROC considers the illness in this area to be undiagnosed. To date, reports have indicated leptospirosis, an RNA virus of the Hantaan group of hantavirus, food poisoning, typhoid, and a previously undiscovered disease; it is unclear if one or any of the disease etiologies have been confirmed by the Pasteur Institutes in both Algeria and France. A recent report indicates that the illness remains undiagnosed and tests from a US laboratory are pending. AROC monitors the first appearance or reappearance of a pathogen in a country as it can often signify abnormal disease activity.

FIG. 26

SYSTEM AND METHOD FOR DETECTING, COLLECTING, ANALYZING, AND COMMUNICATING EVENT-RELATED INFORMATION

CROSS-REFERENCE TO RELATED APPLICATIONS

The present application is related to and claims priority to U.S. Provisional Patent Application Ser. No. 61/368,054, filed Jul. 27, 2010, and is a continuation-in-part of U.S. patent application Ser. No. 12/230,397, filed Aug. 28, 2008, which is related to and claims priority to U.S. Provisional Patent Application Ser. Nos. 61/064,256, filed Feb. 25, 2008, 61/046,275, filed Apr. 18, 2008, and 61/077,713, filed Jul. 2, 2008, the contents of which are incorporated herein in their entirety.

STATEMENT REGARDING FEDERALLY SPONSORED RESEARCH OR DEVELOPMENT

This invention is related to federally sponsored research and development under ITIC contract number 2006-1016 426-000, TATRC contract numbers W81XWH-04-1-0857 and DAMD17-94-V-4015, NLM Contract number N01-LM-3-3306, and DC DOH Contract number PO-HC-2004-P-1545, and OSC contract number 2008-1176516-000. The invention was made with U.S. government support. The U.S. government has certain rights in the invention.

BACKGROUND OF THE INVENTION

Field of the Invention

The present invention involves detecting and tracking global events, such as communicable disease outbreaks, and collecting, analyzing, and reporting information relating to those events to decision makers and the public using various communications modes.

Description of the Related Art

Malaria, diphtheria, cholera, smallpox, influenza, and plague, among many other diseases, have had devastating consequences throughout human history. The first recorded pandemic of plague is thought to have begun in Egypt around 540 AD and to have swept through Europe, Africa, and parts of Asia, killing an estimated 50 percent of the population in those areas. A second pandemic, the Black Death of 1346 to 1352, killed an estimated 20 to 30 million people in Europe, or approximately one-third of the continent's inhabitants. Echoes of that pandemic reverberated for centuries, resulting in major political, cultural, and religious upheaval. A third pandemic, which is ongoing, originated in China in the late nineteenth century and brought plague to the United States early in the twentieth century. By 1718, this third pandemic had claimed an estimated 12 million lives in India alone.

At the root of those pandemics was *Yersinia pestis*, the bacterium that causes three different kinds of plague: bubonic, characterized by bubos, often in the groin or axillae; pneumonic, characterized by involvement of the lungs; and septicemic, characterized by bacteremia. All forms of the disease have high mortality rates when left untreated. Moreover, the disease can be spread not only by insect vectors (e.g., fleas that have fed on infected rodents), but also, in the pneumonic form, from person to person via infectious aerosols and droplets. Human migration and travel spread the disease over long distances.

While plague is more virulent than many other infectious diseases, its infamy in terms of geographic coverage and numbers infected is hardly atypical. Epidemic and pandemic measles, tuberculosis, and cholera have exacted staggering death tolls. Near the end of World War I in 1718, a vicious strain of influenza A virus emerged and spread rapidly throughout the world. The 1718 strain—called the "Spanish flu," although it is unclear where the strain originated—was unusual in that it tended to cause death in young and healthy adults, as opposed to young children and the old and infirm. Spreading efficiently through droplet transmission, the upheaval of the war probably made global transmission more efficient. The disease first spread easily in close military quarters and was then translocated throughout the world as troops returned to their native countries. The pandemic, lasting about a year, killed an estimated 20 to 50 million people, and sickened another 300 million. In the United States, 300,000 or more people are believed to have died of the 1718 flu. By comparison, in 2003, an estimated 3 million people died from human immunodeficiency virus (HIV) infection globally, of which about 20,000 of those deaths occurred in the United States, and an estimated 35 to 40 million globally were living with the infection. Thus, the 1718 flu counts among the most devastating events in human history.

More recently, a previously unknown agent, severe acute respiratory syndrome (SARS) coronavirus, emerged from Asia and spread rapidly throughout the Pacific Rim and beyond. Between November 2002 and July 2003, more than 8,000 people worldwide developed SARS, of which nearly 800 died. The SARS virus is spread primarily by droplet via person-to-person contact, although aerosol transmission may also play a role. The SARS outbreak was particularly problematic in Southeast Asia, as well as in Canada, where more than 200 cases were recorded in multiple provinces. In late July 2003, the World Health Organization (WHO) declared the global outbreak to be over, although laboratory-associated infections have since occurred. While SARS is thought to have been eliminated from the human population, its significant case fatality rate (approximately 10 percent), and its ease of spread, warrant continued global surveillance.

New infectious agents continue to emerge. Over the past 30 years, dozens of previously unknown agents have been discovered. The nature of these newly emergent pathogens is varied, and in many cases is incompletely understood. Moreover, known pathogens can mutate to create new strains to which the human immune system is naïve or ill-adapted, and which do not respond to existing vaccines and pharmacological treatments. This scenario is common among influenza viruses, which undergo reassortment at random intervals, potentially producing pandemic strains capable of causing devastating disease.

For example, after the devastation of 1718, influenza pandemics occurred in 1957 and 1968, although they were less lethal than their 1718 predecessor. Today the world awaits the next such pandemic event. At present, there is heightening concern that a recently emergent avian influenza virus, A/H5N1, may have the potential to ignite the next influenza pandemic. Regardless of what happens with avian flu, the question is when, not if, the world will next experience pandemic influenza. Whether the next pandemic will unfold into a catastrophic event, akin to that of 1718, will depend on a variety of molecular, social, economic, medical, and public health factors.

On the darker side of human endeavor is the specter of biological warfare and bioterrorism, in which dangerous communicable agents can be spread either intentionally to human populations or agriculture. Although the Cold War superpowers did not engage in biological warfare, accidental infections have occurred among workers involved in weapons programs. Similarly, at least one catastrophic accidental release of a bio-warfare agent has been documented. Accidental infections with common pathogens have also occurred in research as well as public health laboratories. If terrorists, who almost certainly lack sophisticated laboratory infrastructure and advanced containment protocols, pursue bio-weapons, the world will likely be at risk for additional accidental releases, to say nothing of intentional attacks.

In addition to morbidity and mortality, the widespread propagation of disease can have devastating social and economic impacts. For example, the U.S. General Accounting Office (now the Government Accountability Office) reported that the SARS crisis "temporarily dampened consumer confidence in Asia, costing Asian economies $11 billion to $18 billion and resulting in estimated losses of 0.5 percent to 2 percent of total output, according to official and academic estimates. SARS had significant, but temporary, negative impacts on a variety of economic activities, especially travel and tourism. Moreover, in the modern world of international investment, economic losses in one region can affect performance in distant regions. For example, a number of U.S. companies suspect that they experienced quarterly losses in 2003 because of SARS.

The tremendous impact of the HIV/Acquired Immune Deficiency Syndrome (AIDS) pandemic on African economies has been widely studied. Certainly, the impact has been complex; however, the pandemic has clearly tended to reduce labor supply and productivity while increasing the need for imports. Economic models suggest that HIV/AIDS will continue to have serious, long-term economic consequences throughout sub-Saharan Africa. These consequences pose a challenge to all nations, which must deal with reduced foreign markets and the increasing need for humanitarian outreach and international aid.

Emergent plant and animal diseases also affect economic and social institutions. In 2001, during the outbreak of foot and mouth disease in the United Kingdom, agricultural producers suffered estimated losses of £355 million, or about 20 percent of the region's estimated total income from farming that year. Moreover, businesses directly affected by tourist expenditures lost an estimated £2.7-£3.2 billion as fewer people visited the countryside. Overall, the outbreak is estimated to have reduced the United Kingdom's gross domestic product by approximately 0.2 percent in 2001.

A variety of socio-economic factors encourage the spread of infection. Predating the Spanish flu pandemic by nearly three decades, the influenza pandemic of 1890 demonstrated that even by that the late 19th century, steamship and railroad travel had made the rapid, global propagation of pathogens possible. Since then, influenza pandemics have reached farther and wider as a result of advances in travel technology such as air transport, and on account of the global proliferation of traffic nodes.

The world is growing more crowded and more interconnected. Should any pathogen, such as influenza A/H5N1, emerge as a major threat to human health, it could spread rapidly throughout the globe. In 1718, the global population was approximately 1.8 billion; today it has surpassed 6 billion, and it is projected to be near 9 billion by 2050. This population increase has resulted in the phenomenon of megacities (cities with populations greater than 10 million).

In 1960 there were two such cities; by 2000 the number had risen to 20 worldwide. The number of such cities projected for 2015 is 26, with 22 of them in developing nations and 18 in Asia alone.

Such high populations are likely to dramatically increase the opportunity for close-contact transmission of many pathogens, including diarrheal, respiratory, and foodborne agents, and to pose unique problems for rapid containment. This concern is particularly relevant for megacities in the poorest areas of the world, where problems of malnutrition and diminished immune status may be expected to grow. It can be expected that large populations will surpass the threshold numbers required to sustain as-yet undiscovered diseases. Measles, for example, did not become endemic until the size of human settlements surpassed about 250,000 inhabitants. It is not unreasonable to expect that newly emergent pathogens will gain footholds and thrive in our increasingly densely populated world.

The proliferation of air travel is also likely to facilitate the transmission of new pathogens. In 1990, 81 million passengers and 7.7 billion pounds of freight were exchanged between the United States and the rest of the world by air. By 2004, global air traffic had increased to 138 million passengers and more than 16 billion pounds of freight. In 1718 there was essentially no international air travel; today more than 18 million commercial flights serve virtually all areas of the world. It is currently possible to circumnavigate the globe in 36 hours via regularly scheduled commercial flights.

These statistics highlight two crucial epidemiological trends over the last few decades: (1) people are traveling more, and (2) travel times are dramatically shorter. Thus, larger numbers of individuals are traveling to areas where exotic and emerging pathogens circulate. Similarly, more people, living species, and agricultural commodities are crossing borders than ever before, increasing the likelihood that diseases previously confined to areas where populations have developed some immunity to the responsible pathogens will be introduced into immunologically naive populations. Moreover, once a new pathogen appears in any given area, it is increasingly likely to be spread globally via air travel within a matter of days. Under these combined circumstances, nations are likely to confront new infectious diseases as their citizens travel abroad and return. The effects of such easy disease transmission on international commerce could be enormous.

To preserve human health and economic well-being in this new context of dense populations and frequent air travel, there must be effective global surveillance of infectious diseases. Only through such surveillance will it be possible to prevent outbreaks from spreading throughout the world. The payoff from early warnings regarding infectious disease is well documented. Cases accumulate exponentially in the early phases of an epidemic until some degree of population immunity is achieved. At this point, new cases appear more slowly and eventually cease. If an epidemic is identified early, and effective control measures such as quarantine, immunization, and travel/trade embargos are instituted, the appearance of new cases slows, and ultimately ceases as the epidemic is brought under control. In such a scenario, morbidity and mortality are significantly lower than in the case with no early warning and no control. Under the best-case scenario, one with even earlier warning and action, action is taken earlier and the epidemic is brought under control shortly thereafter. Note that, because of the exponential character of epidemics, the tiniest bit of action taken at an early stage can dramatically alter the course of the disease; thus, illustrating the importance of early warning.

One international effort to facilitate early warning of dangerous infectious disease globally involves the International Health Regulations (IHRs; revised in May 2005). The IHRs have their origins in the cholera epidemics that affected Europe between 1830 and 1847. They are designed to "prevent, protect against, control and provide a public health response to the international spread of disease." The regulations require member nations to notify WHO within 24 hours of finding a single case of any of the diseases on WHO's watch list, and to report other public health emergencies of "international concern" within their jurisdictions. Furthermore, the regulations set forth measures for deratting, disinfecting, and disinfecting international conveyances (such as ships and aircraft) at points of arrival and departure. Under the IHRs, nations are obligated to build "national capacity for routine preventive measures as well as to detect and respond to public health emergencies of international concern. These routine measures include public health actions at ports, airports, land borders and for means of transport that use them to travel internationally." Thus the IHRs embody the public health maxim that "an ounce of prevention is worth a pound of cure." However, not all nations have the capacity to detect such diseases within their own borders. Moreover, in some instances, governments may suppress information relating to outbreaks that could lead to adverse economic consequences (such as embargoes on potentially infected products, or reduced tourism).

At the international level, there are both official and unofficial mechanisms for international disease notification. The primary means of official notification resides with WHO's Global Alert and Response Network (GOARN), a global network of WHO member states, United Nations organizations, and partner nongovernmental organizations that respond to the needs of member states in crisis due to epidemic disease. Standardized protocols for network structure, operations, and communications have been agreed upon in an effort to improve coordination among the GOARN partners. WHO provides institutional support for the network (such as employment of project managers and support for the steering committee) and coordinates international outbreak response using network resources.

One of the services GOARN maintains is the Canadian-based Global Public Health Intelligence Network (GPHIN), which scans global media articles via the Internet for references to disease outbreaks and epidemics. In May 2003, partly in response to the SARS crisis, WHO began formally utilizing the information sources searched by GPHIN, in conjunction with government reports, to issue global disease alerts.

Unofficial notification occurs via many means, such as the Program of Monitoring Emerging Diseases (ProMED), a moderated Internet mailing list that tracks emerging infections of humans, plants, and animals. Currently a program of the International Society for Infectious Diseases (ISID) and, therefore, not bound by multilateral agreements, ProMED does not require an official mandate to post and disseminate information. Rather, it relies on volunteers from around the world to submit information about infectious diseases and related issues. Much, though not all, of this information consists of media articles. Submitted material is vetted by a group of experts so that only the most relevant and credible information is displayed.

The GPHIN utilizes the international connectivity of the Internet to help detect disease. However, at present, it is limited by the volume and type of media material that can be processed in multiple languages. Additional limitations affect WHO's ability to detect and assess a rapidly spreading epidemic, including the lack of adequate public health infrastructure in member nations, the potential involvement of a previously uncharacterized pathogen (as in the case of SARS), ongoing conflict that inhibits the flow of information out of nations, and the willingness of states to report the extent of an outbreak.

Likewise, while ProMED and similar networks are valuable complements to official sources, their volunteer nature limits the number of staff available to process the volume of submitted reports. Similarly, such networks tend to have limited resources to support language translation issues. In concert, these limitations compromise the ability of volunteer networks to provide comprehensive early warning of potential outbreaks.

The limitations described above highlight differences between raw medical surveillance data and the translation of those data into actionable threat information. During the initial stages of an outbreak, very little may be known about an event. As time progresses, this uncertainty typically decreases, though it may do so slowly. On the other hand, the probability of translocation to other areas tends to increase with time. The key public health question is, when should action be taken to reduce risk? There are many choices. The time at which preventive actions are taken will be a function of medical as well as social, political, and economic factors. Nonetheless, actionable information acts to decrease uncertainty and can provide a strong rationale for early measures to minimize the likelihood of translocation.

For example, the VEE epidemic represents a possible translocation issue for the U.S. given air traffic from Maracaibo, Venezuela, connected directly to Miami (with unknown connector flights to other destinations within the U.S.) that seasonally peaked during the month of containment loss. To-date, it is unknown whether it would have been possible that VEE could translocate to Miami, trigger an outbreak that progressed to an epidemic, ecological establishment, and repeated seasonal transmission thereafter for years to come. A comprehensive assessment of the transmission competency of endemic mosquito species in Miami would be necessary to determine if this was a valid hazard concern.

In 1979, a laboratory accident involving aerosolized anthrax occurred in Sverdlovsk, Russia. From Apr. 14-May 18, 1979, local media in Sverdlovsk explicitly reported the occurrence of a series of human cases of inhalation anthrax along with draconian countermeasures as officials sought to rapidly contain and conceal the true etiology of the event. In 1992 and 1993, a team of American and Russian researchers led by Meselson and colleagues traveled to Sverdlovsk to investigate evidence for two hypotheses of the anthrax epidemic of 1979, the official USSR version that infected meat caused the outbreak and the US intelligence claims that the true etiology of the epidemic was an accidental release of aerosolized anthrax spores from the Compound 19 within the Voyenny Gorodok 47 biological weapons laboratory located in the city. The Meselson team concluded that an accidental aerosol release had indeed occurred on Apr. 2, 1979, resulting in what is thought to be the largest documented outbreak of human inhalation anthrax in history. Declassified U.S. intelligence archives suggest the intelligence community was unaware of this event until months after the fact.

This example highlights the requirement for a tactical approach to detect biological events and to baseline not only the epidemiological data for the disease itself, but social responses as well. Identifying "unusual" biological events that are evolving rapidly, with an attendant recurrence, elevation, and diversification of the indications and warnings, may assist in a time-sensitive evaluation of whether there may be a question of attribution. Of particular note, through retrospective and prospective studies, it has been known that an indicator of intentional release is not often the first apparent tip to an analyst; rather, it is the identification of an "unusual" biological event that is later found to be related to suspicious conditions.

In each of those examples, the biological event in question produced a "ripple effect" whereby indications and warnings (I&Ws) appeared in media. The analyst is in a struggle against time to put pieces together to tell enough of a coherent story to alert the user community to awareness. To properly capture events and triage advisories appropriately, a blended I&Ws reporting requirement list that incorporates an integrated disease list has been developed.

At a workshop sponsored by the U.S. Army in 2004, entitled "The Role of Indications and Warnings for Prediction and Surveillance of Catastrophic Biological Events," a panel of researchers concluded that decision making could be strengthened by using a graded threat awareness scale that corresponds to varying levels of confidence in the potential for a given disease to spread. However, neither the newly revised WHO Pandemic Phases nor the Canadian or U.S. governments' current concepts of how to respond to pandemic influenza provide specific guidance for cross-matching actionable threat information to response decisions. Such a scale could support a graded response to imperfectly known threats.

Researchers have recently investigated the use of local-level syndromic surveillance to anticipate reports of clinically confirmed disease. The basic idea is to target the early manifestations of disease as they are presented to health care workers. Whether syndromic surveillance is likely to detect an epidemic sooner than the usual methods (such as reporting by alert clinicians) is unclear. Nonetheless, the underlying concept of discerning peri-event signatures that are indicative of disease transmission may prove useful in initiating more traditional epidemiological investigations at earlier points in the life of a disease.

Panelists at the 2004 I&W workshop concluded that there may be observable social, economic, and political signatures of the early stages of large-scale biological events. If such signatures could be used to cue confirmatory epidemiological investigations, it might be possible to identify and contain outbreaks days or weeks before current approaches are able to do so. Thus, these I&Ws may have the potential to identify an epidemic in its early stages, thereby allowing for more effective control and prevention of its regional or international spread. Conference attendees published their proceedings in 2004, which included postulating use of the Internet to gather documents containing I&Ws for event detection purposes.

No single approach can achieve that goal. Rather, a combination of approaches is necessary to reduce risk and support decision making that is meant to mitigate the translocation of biological threats. It is posited that at least two approaches can be combined to create a global I&W system that meets the goals of early detection. The first is environmental surveillance for ecological markers of conditions supporting disease emergence. In many areas of the world, environmental conditions are known to play a key role in the emergence of certain infectious agents, especially vectorborne pathogens. Satellite sensors can monitor environmental conditions (such as vegetation health, rainfall, and standing water) over large areas, and the risk of disease emergence can be assessed based on those observations. Static or seasonal maps of areas that are ecologically suitable for disease emergence or transmission, coupled with maps of transportation routes for different disease hosts (such as humans and livestock) and vectors, may prove useful in the short term. Longer-term, more sophisticated systems that collect and update such data, then make it available for analysis, are needed.

The second approach is to monitor the Internet for markers of "social disruption" that indicate anomalous infectious activity. Both adaptive and maladaptive social responses to disease epidemics have been studied previously. McGrath (1991) examined the historical ethnographies of 229 ethnic groups from North and South America, Europe, Africa, the Middle East, Russia, and Oceania, and recorded six basic social responses to epidemics: mass evacuation or flight from the site of the epidemic, extraordinary therapeutic or preventive measures, scapegoating of individuals or institutions, acceptance of disease, ostracism of the ill, and conflict. Of these, flight was found to be the most common. McGrath noted that the acute, dramatic appearance of disease, particularly unfamiliar disease, with high rates of morbidity and mortality provoked the strongest social response. McGrath observed that if established indigenous countermeasures failed, innovative countermeasures were undertaken, followed by social disruption that began with flight, then proceeded to acceptance of disease, to rejection of authorities, and ultimately to conflict. This sequence, McGrath argued, depicts a society that has degraded from normal functional status to disintegration. It is inferred that social disruption may be characterized as an emergent property triggered by a biological threat that defies countermeasures, control, and containment.

The near-global coverage of the Internet has led to highly fluid formal and informal reporting of local and regional news and events relating to social disruptions. Such reports contain information about the collective behavior of communities, which in turn can provide implicit or explicit information on the health of peoples. That approach promises to become even more comprehensive as the Internet continues to expand its reach. The use of the Internet for that purpose was described in a NASA open source reader in 1998.

Both approaches—monitoring the environment for ecological markers of conditions supporting disease emergence, and monitoring the Internet for markers of "social disruption" that indicate anomalous infectious activity—are supported by advances in information technology. For example, multisource data mining, machine learning, and language translation algorithms are now available to expand upon the GPHIN approach of exploiting published media reports. Similarly, remote sensing of many types of relevant environmental conditions is now possible at low or no cost over the Internet. Moreover, computer modeling and simulation can be used for analysis. For example, the Soviet Union developed computer models that successfully tracked the nationwide spread of influenza. Later, the approach was used retrospectively to analyze the 1968-69 pandemic of influenza A/H3N2. Recent research suggests that such a tool, together with up-to-date data on transportation and human movement, could be used to examine optimal control strategies early in an epidemic. Transportation network analysis, an active area of research, is necessary for understanding the relationship between global connectivity and infectious disease threats.

A global I&W system represents only one tool in the armamentarium of ways to address the threats posed by infectious disease. Knowing that a potentially threatening biological event is under way somewhere in the world is a necessary condition for mitigating its effects, but it is not sufficient. The social, economic, and political context of the threat will determine how it can be controlled. It may be useful to think of infectious disease threats in the same way we think of meteorological threats. In the United States, the National Weather Service operates a warning system for severe weather. It is generally acknowledged that this system is important and worth maintaining and improving, but knowing that severe weather is threatening a particular area at a particular time is not sufficient to save lives; people must use the information to that end. Such is the case with infectious disease, as well.

Nonetheless, early warnings of infectious disease threats remain a pillar of public health and national biodefense decision making, especially in the face of current world trends in transportation, commerce, and population. A global I&W system would be broadly applicable to natural, accidental, and terrorist-induced outbreaks of human and agricultural diseases. Any such tool would facilitate more informed decision making and thus would help mitigate the international spread of infectious disease.

It is necessary to have a balance between rapid identification and interdiction of state and non-state sponsored biological weapons programs, and recognition that a Spanish flu of 1718 scenario may severely incapacitate a country's infrastructure, to include its national defenses. It has traditionally been the view held by some that pandemic influenza is a public health, not intelligence concern. The creation of Homeland Security Presidential Directives-7, -9, and -10; National Security Presidential Directive-33; and now Public Law 110-53 have attempted to resolve this debate and place intelligence within the context of a national biosurveillance integration strategy for biological defense. The operational reality is that a biological event effecting humans or animals may translocate from any place in the world to any other place before adequate ground truth and attribution assessment can occur due to the substantial global transportation and commerce grid.

Topical and geographic focus, as has been observed in agencies such as the U.S. Centers for Disease Control and Prevention (CDC) and the U.S. Department of Agriculture (USDA), has been typically stove-piped within specialty programs that do not readily share information with other programs. A global picture of situational awareness that spans all attribution concern has not been available either at the intra- or inter-departmental level sufficient to operate in the new global operations environment that demands a rapid event detection-to-ground truth cycle. Determination of attribution is often a time-sensitive forensic process, as evidenced by the activities of Aum Shynrikyo, the Rajnessh cult, Japan Unit 731, South Africa's Project Coast, and the immense former Soviet Union biological weapons program. Coupling near-real time I&Ws to traditional epidemiological approaches and intelligence is a critical need in today's global community.

The intelligence community faces several issues that may present themselves similarly in an I&W detection and tracking environment:

Naturally occurring biological events of high potential consequence to the U.S. and its allies (e.g., pandemic influenza);

Accident of biotechnology producing a biological event of high potential consequence to the U.S. and its allies (e.g., accidental reintroduction of pandemic influenza virus that has not been in global circulation for decades such as the appearance of H1N1 in 1977);

Accident of state or non-state sponsored biological weapons program resulting in a biological event of high potential consequence to the U.S. and its allies (e.g., hypothetical laboratory accident involving terrorists that releases a respiratory virus that transmits efficiently in the surrounding community);

Intentional test release of a pathogen by a state or non-state sponsored biological weapons program resulting in a biological event of high potential consequence to the U.S. and its allies (e.g., terrorist group performs a limited field test with a respiratory virus that transmits efficiently in the surrounding community); or Intentional deployment of a biological weapon by a state or non-state sponsored program (e.g., terrorists deliberately release plague in an urban area).

Other issues of importance include rapid identification and monitoring of suspected state or non-state programs that may be associated with named individuals or institutions.

There are different time differentials, sensitivities, and specificities associated with the spectrum of products involving rapid processing of I&Ws versus a finished assessment.

I&Ws have long been used in intelligence. In World War II, one effective indicator of the success of Allied bombing raids on the French railroads was the price of oranges in Paris: successful raids disrupted transportation of the fruits (from southern France to the capital city) sufficiently to cause a transient price spike. In biological surveillance, one family of indirect indicators is based on observations of other, "sentinel" species that serve as alternative hosts for an infectious agent or are exposed to the same pathogen to a relatively greater extent. Historically, a plague epidemic was heralded by the appearance of numerous dead rodents: the fleas that spread the disease among them would now move to another source of blood (human hosts). Human methyl-mercury poisoning in Japan (Minamata disease) was preceded by neurological symptoms in cats that ate contaminated fish, and bird deaths are monitored during surveillance for West Nile fever. Other indicators are more remote, in that the causal links are less obvious given the state of existing knowledge. Edward Jenner's work on vaccination was triggered by his exploration of the old wives' tale that milkmaids rarely got smallpox. It turned out that, after they were infected with cowpox from the animals they milked, they acquired immunity to the smallpox pathogen.

Today's researchers, unlike their counterparts of the past, have near real-time access to vast amounts of different types of data. The technologies grouped under the rubric "data mining" enable researchers to plow through data to generate a vast number of hypotheses in a prioritized fashion. Offset against that advantage are the following caveats:

Few data mining techniques are associated with tests of statistical significance: a suggested hypothesis does not usually come with a "p-value."

An observed relationship between an indirect indicator and the pathogen does not, in the absence of additional knowledge, imply cause or effect. Further, because of the problem of confounding variables, the factors that may be predictors may turn out not to be so. That problem has been known since the devising of the Pearson correlation coefficient in the early 20th century. Two variables that were apparently highly correlated were found to be associated only because of a third unconsidered variable. The spurious association reported by Huff between the salaries of Presbyterian ministers in Massachusetts and the price of rum in Havana (with the common variable being inflation) is an example of this problem. Thus, indirect indicators may not always reflect cause-and-effect relationships.

Given finite resources, the number of hypotheses that one would like to explore is always far greater than the number of hypotheses that one can explore.

Previous investigators have attempted to define event evolution as a function of media reporting. Cieri and colleagues (1802) proposed that an event be defined as "a specific thing that happens at a specific time and place along with all necessary pre-conditions and unavoidable consequences." Makkonen (2003) observed that a seminal event can lead to various related events and outcomes, and the initial cause of these events may become less obvious over time. Chin and colleagues proposed that a media-reported event can be considered "a life form with stages of birth, growth, decay, and death," and that the maintenance of the reported event is dependent on sensationalism. Those analyses, however, did not identify variable properties of media reports that are potentially useful as indirect measures of the intensification of I&Ws over time: recurrence, elevation, and diversification. By these measures, biological events may be reported as increasingly complex phenomena over time, whose "nourishment" is dependent on whether the biological agent in question is perceived by the local community to remain an active threat of concern.

What is needed is a system and method for facilitating disease reporting that covers regions of the world where there is poor or nonexistent disease reporting infrastructure. What is also needed is a system and method that provides situational awareness of biological events, especially epidemics of infectious disease in regions where such information is suppressed, and newly-emergent pathogen events where the pathogen has unknown characteristics. What is also needed is a system and method to detect and respond to a pandemic that is transparent, facilitates scientific cooperation, and allows for rapid reporting of biological outbreaks in birds and humans.

In the summer of 2004, an allocation of funds from the Intelligence Technology Innovation Center (ITIC) and the Department of Homeland Security (DHS) was made available to support research and development of a completely novel approach in foreign biosurveillance: Project Argus (now Global Argus), which is a real-world embodiment of the presently disclosed invention.

SUMMARY OF THE INVENTION

Biosurveillance requires a synthesis of analytic approaches derived from the natural disaster, intelligence, public health, epidemiological, medical, veterinary, agricultural, meteorological, anthropological, and sociological communities, among others. With the exception of the GPHIN and WHO, at the time of conception of the present invention, a formalized professional discipline in operational biosurveillance with research, education, and training support did not exist in the U.S. Accordingly, a principal object of the present invention is to provide such an operational biosurveillance capability. In particular, it is an object of the present invention to provide a global biological event detection and tracking capability that provides early warnings of biological events, and estimations of the probabilities of such events escalating. To reach that object, the present invention relies on monitoring social disruption through native language reports in electronic local sources around the globe, because local societies are highly sensitive to perceived emergence of biological threats, and the resulting conditions and responses are readily identifiable through a granular review of local sources of information using the present system and method.

Without limiting the invention, the term "social disruption" is defined generally as a severe alteration in the normal functioning of a social system that, under extreme conditions, can lead to the collapse of social infrastructure. Social infrastructure is the range of activities, organizations, and facilities supporting the social relationship in a community. Extreme social disruption exacerbates the effects of biological events.

In the present invention, prior sociological and anthropological descriptions of social disruption have been expanded by applying the concept to the detection and assessment of biological threats. I&Ws (or markers) of social disruption, used in tandem with explicit reports of disease, can identify an emerging biological event and indicate its level of containment. Without limiting the invention, the term "containment," as used herein, is defined to mean the process by which an indigenous public health and medical infrastructure undertakes countermeasures aimed at controlling an outbreak or epidemic. Three general conditions favor the use of the social disruption approach: inadequate support for local disease reporting, suppression of information about health crises, and/or the emergence of a previously unrecognized pathogen or of a well-known pathogen that displays dramatically different transmission properties than previously known or suspected.

Biosurveillance involves significant human analysis of information. Thus, it is another object of the present invention to use manual and automated computerized techniques for collecting electronic information relating to social disruption, by looking for specific I&Ws, and then analyzing the collected information. The information collection, information processing, and analysis subsystems of the present invention are based on the isisMiTAP (ISIS Center/MITRE Text and Audio Processing) platform originally developed under the Defense Advanced Research Projects Agency's Translingual Information Detection Extraction and Summarization Program (DARPA-TIDES). The isisMiTAP offered an online news service and information retrieval system that captured and categorized information according to user-defined, searchable newsgroups. Using isisMiTAP, media sources could be iteratively searched using multiple keyword combinations. The searches included only articles published in English or translated into English by regional news sources. To extend the range of data sources, additional searches with isisMiTAP using Chinese-, Russian-, and Korean-language local news sources and regional business and financial reports were conducted, sometimes with the aid of a bilingual human translator. From that platform, the present invention as described herein evolved.

It is another object of the present invention to use grounded sociological theory to develop a set of I&Ws of social disruption illustrating the dynamic properties of each type of social response over time. I&Ws include reports of human or animal disease, demand for medical services, local perception of threat, official acknowledgment, official action, and integrity of infrastructure. The I&Ws represent important ways in which an emerging epidemic might disrupt the everyday social life of individuals, communities, and institutions; therefore they might appear in local, regional, or national media sources. The expanded capture of media reports from local and regional sources provides crucial information because such sources reflect local knowledge of typical and atypical phenomena.

It has been hypothesized that selected I&Ws would display cross-cultural reliability. For example, it was expected that evidence of local perception of threat wherever and whenever individuals initially become aware of an emerging epidemic would be found. Without limiting the invention, the term "parameter" is used herein to refer to manifestations of a marker appearing in a specific cultural or historical context. It was expected that parameters for most markers would display not only cross-cultural reliability, but also cross-cultural variation depending on the impact of the disease and local conceptions of appropriate response. The parameters for some markers, such as official acknowledgment, may display less cross-cultural variation than others, a point for exploration in future analyses.

It is another object of the present invention to monitor the changes in I&Ws over time. Three variable properties of media reports have been identified—recurrence, elevation, and diversification—that may serve as indirect measures of the intensification of I&Ws over time. Without limiting the invention, "recurrence" is used herein to refer to additional reports of a phenomenon already described at least once in the media. Media reports may also describe increases in a phenomenon, indicating "elevation" of its manifestation. Without limiting the invention, "diversification" as used herein to refers to the emergence of multiple parameters of a single marker. As media reports repeatedly describe elevated levels of increasingly diverse parameters of particular I&Ws, a picture emerges of an uncontained, intensifying biological threat with increasing potential for international translocation.

Two broad categories of I&Ws—direct and indirect—are consistent across the cultures, diseases, and situations that have been examined. Direct I&Ws, such as reports of a disease outbreak, derive from medical and veterinary information and refer specifically to a biological event. Indirect I&Ws encompass qualitative information regarding social disruption and containment status, such as reports suggesting that individuals and organizations have begun changing their daily routine activities in response to a perceived biological event.

It was hypothesized that when analyzed as a whole, media-based I&Ws may reveal a biological event evolving in geotemporal fashion. Remarkable similarity in social disruption parameters across biological events that involved different pathogens affecting humans has been observed. This similarity has also been seen across multiple countries and time periods. The initial findings also suggested a similarity between the social disruption caused by pathogens that affect humans and those that affect animals. It is recognized that more research was required to define the temporal, pathogenic, and cultural differences that existed at various levels of the sociological model.

It is another object of the present invention to use manual and automated computerized techniques for identifying and collecting temporally dynamic social disruption evidence and ranking or defining the evidence by degrees, classifications, or categories.

It is still another object of the present invention to employ a heuristic staging model to characterize an event. Previous scales, including the Saffir-Simpson hurricane, Fujita tornado, and Ricther earthquake scales, are unsuited to the present invention. The present invention uses a heuristic scale model (previously referred to as the Wilson-Collmann Scale), based on the I&Ws of social disruption described above, which is better suited than current methods to detect and assess the dramatic appearance of diseases, particularly unfamiliar diseases, with high rates of morbidity and mortality. Such evolving biological events provoke the strongest social response.

The present heuristic staging model is intended to serve as a guide for analysis and as an interdisciplinary standard operational language. In daily real-world analysis, it would be unlikely to observe a logical flow of information representing the systematic progression of a biological event and associated social responses. As suggested earlier, gaps in information are likely because of inadequate local disease reporting, information suppression, the emergence of a previously unrecognized pathogen, or the emergence of a well-known pathogen that displays dramatically different transmission properties. As with the storm severity scales mentioned above, the present model estimates the impact of a biological event on society, and thus can be used to prompt response decisions about mitigative measures and anticipatory consequence management. Such decisions may range from simple requests for more information to quarantine, closure of country borders, and international trade restrictions. Just as most storms are given low stage designations, the majority of biological events that have been evaluated merited low stage assessments, reflecting the relatively low probability of social collapse induced by biological events.

It is another object of the present invention to provide I&W profiles using a sample size that is appropriate for gauging social disruption induced by various diseases over time. It is believed that there is some variation in the social disruption caused by biological events not only across diseases, but also across countries. That variation is likely due to differences in social tolerance for disruption, the sophistication of public health and medical infrastructures, and the direct effects of the disease in question. It was experientially observed that biological events taking place in countries with limited infrastructure were likely to progress to higher stages more quickly than those occurring in countries with more robust infrastructure. One disease in particular—influenza-like illness—was observed to consistently defy countermeasures across multiple countries with a wide range of medical sophistication. This finding was troubling, particularly in light of current concern about pandemic influenza.

It was hypothesized that, after an appropriate sample size was examined over time, each disease will exhibit a characteristic level of social disruption. If a disease that typically exhibits focal transmission characteristics was found to generate higher levels of social disruption, this information may prompt closer scrutiny of the event for unusual epidemiological features and possible implications regarding attribution. Stages 1 to 4 apply across disease and location, whereas Stage 0 appeared to apply for specific diseases in particular locations. Stage R refers to specific recovery aspects of observed events.

It is still another object of the invention to provide a staging model that allows for upgraded and downgraded staging on a dynamic basis. With the present model, biological event-related social disruption can be readily described as it escalates in severity. However, the dynamic progression of a biological event may follow a pattern of upgraded and downgraded staging to reflect successful countermeasures or particular disease transmission characteristics, among other factors. Future investigations would be necessary to address the difficult question of how social disruption is resolved and normalcy is reestablished in a society. Furthermore, observations of media behavior suggested that reporting became more vigorous and descriptive as an event evolved and generated maximal impact (and sensational interest in media reporting). However, the media tended to report resolution of an event less vigorously, particularly in closed societies. This trend continues to pose a challenge to the analyst with regard to downgrading the staging of an event.

It is noted that the real-world application of the present staging model is likely be complicated by uncertainty. It is anticipated that media reporting of some biological events at any stage may provide only indirect I&Ws, just a single report, or social disruption parameters not included in the model. It is recognized that some biological events may not follow the order of social disruption embodied in the present model. Nevertheless, it is another object of the invention to use categories of recurrence, elevation, and diversification, along with proper contextualization of I&Ws, to allow for more precise categorization of a biological event. Such a staging model would likely be revised as more analyses were conducted across time, cultures, and disease entities. It is recognized that ongoing operational use of this methodology may yield longitudinal data that could be used in forecasting models.

Another object of the invention is to facilitate linking progressive warnings generated in Stages 1 through 4 with prompt, appropriately coordinated response decisions by response officials or end users. Difficult response decisions may have to be made using limited I&W information when no diagnostic information regarding the disease in question is available. If a response must await the receipt of diagnostic information, the resulting delay may mean the difference between mitigation and having to manage consequences after the fact. With regard to the current threat of pandemic influenza, the United States would be prompted into action once WHO has declared that a pandemic is occurring. It has been shown that the system can identify I&Ws that are often present in indigenous local media weeks to months in advance of WHO's public declaration of an international public health threat. Such I&Ws, considered within a model such as the one disclosed here, may enable earlier threat assessment that can prompt scrutiny for an event of potentially global concern.

It is still another object of the present invention to provide, in addition to the staging model previously described, a higher level of assessment of events. After testing an existing scale (in particular, the Wilson-Collmann Scale) on several biological events throughout the Pacific Rim, it was noticed that staging a biological event was useful for event evolution assessment and baselining local community social disruption, but was not as useful for triaging the volume of reports captured. The reason for this is, while detecting social collapse is important, the user community would want to be notified of an event and maintain awareness from the early piece of information to an event's ultimate outcome. Therefore, a higher level of assessment, akin to the National Weather Service's Warning, Watch, Advisory approach to storm tracking, was identified as a need and is used in the present invention.

One of the key research questions throughout the development of the present system has been, and continues to be, "what is actionable"? It was found, experientially, that if several members of a biosurveillance operations team at CDC, USDA, DHS, or DOD were posed this question, the response would involve different answers. It reflected no prior experience by these analysts with a codified operations approach to prioritize reporting requirements and understand how triaged information may drive response actions by their respective organizations.

The National Weather Service advisory system model was seen as the most relevant and appropriate one to use, however implementation was in a vacuum of federal guidance. Those involved in the present system initially tested various approaches of this model based primarily on social disruption, then later factoring other parameters as described later.

Still another object of the present invention includes providing a system and method for early biological event detection with high sensitivity of event tracking, which includes monitoring countermeasure efficacy and issuing actionable advisories.

It is another object of the present invention to detect agents that can compromise/collapse an Intensive Care Unit and therefore collapse an urban hospital and prompt a city-wide "medical blackout."

It is still another object of the present invention to monitor and assess an event site in terms of its connectivity to the U.S. by air flights and commerce trade.

It is another object of the present invention to facilitate coupling the detection and forecasting capabilities of the present system with the collection of ground truth evidence by others, such as end users. Biological event evolution is a process where the analyst is typically not responding to specific, explicit declarations of an outbreak of an expertly diagnosed disease as the first tip of information to start an event case file. The first piece of information may simply be a report of bird die-offs; the etiology of the die-offs may involve dozens of possibilities. If the analyst notes panic buying of herbal medicines in the same province, that may or may not be related to the report of bird die-offs. The analyst struggles throughout the process with uncertainty, and over time this uncertainty is resolved in the flow of local and multi-lingual reporting. Ultimately, it is hoped this information is clarified with independent, trusted third party ground truth.

It is still another object of the present invention to identify evidence indicating that containment of an event has been lost.

Another object of the present invention is to provide the capability to monitor thousands of validated sources providing coverage in all recognized countries or regions around the globe in multiple languages within an online information harvesting engine (including languages such as, but not limited to, English, Spanish, Portuguese, Italian, French, Japanese, Korean, Farsi, Dari, Arabic, Urdu, Indu, Georgian, Chinese (Mandarin and Cantonese), Mongolian, Czech, Russian, Macedonian, Serbo-Croat, Bulgarian, Slovak, Bahasa Indonesian, Malay, Tajik, Uzbek, Kyrgyz, Kazak, Hindi, Greek, Vietnamese, That, Romanian, German, Hebrew, and Turkish).

It is still another object of the present invention to provide a subsystem for verification of information. The inherent nature of biological event I&Ws means that more often than not, there is a significant degree of uncertainty until ground verification has been obtained. Time is critical, particularly when considering the discovery of a novel influenza virus such as H5N1, and whether or not it may be efficiently transmitting between humans. Ground verification must occur rapidly enough to enable decision making for rapid global response. This has direct implications for decisions regarding sharing of information with state and local authorities.

Another object of the present invention is to provide a system for communicating to end-users specific or summary local- and country-level reports along with assigned stratified social disruption stage and/or alert levels, which may be used by others for developing actionable decisions.

It is another object of the present invention to communicate information about biological events for biodefense purposes. Biodefense is the application of government and private resources to protect the nation against biological threats, including natural, intentional, and unintentional threats. Biodefense is important for at least the following reasons: (1) disease outbreaks are not tied to geographic or political boundaries; (2) bioevents may cause catastrophic harm; (3) real-time early detection may have a significant difference in outcomes; and (4) there is a perception that the U.S. does not have sufficient capabilities to provide early detection and respond with an adequate response to bioevents.

Another object of the present invention is to provide a scalable system that can be adapted to adding additional servers and interface programs to accommodate increasing amounts of documents collected from information sources, as well as to accommodate more analysts running more and more queries, and to allow increasing numbers of end users/customers with access to the system.

Other objects of the present invention include disseminating information to end users, providing a multi-lingual search engine, providing machine and manual translation support, providing an input to allow users to annotate collected articles, providing a routine to categorize collected articles, providing an integration platform that ties the above features together, and to allow for special data fees and collection methods on an ad hoc basis.

Still another object of the present invention is to apply the biosurveillance capabilities of the system for use by government, corporate, insurance, financial, commodities, and investment entities, as well as to provide situational awareness of the public and private markets in which those entities operate.

Briefly described, those and other objects and features of the present invention are accomplished, as embodied and fully described herein, by a method for communicating event information, which includes the steps of outputting over a communications network a first instruction to a client computer to display a graphic on a graphical user interface device, the graphic including at least a planar representation of a portion of the Earth's surface, and retrieving information stored in a first database concerning a first event, wherein the first event is identified from at least one parameter associated with a plurality of indications and warnings, and wherein the information comprises a first scale value describing a severity of the first event and a geographical location describing a location of the first event. The method also includes the steps of selecting from a plurality of indicia a first indicia representing the scale value of the first event, the first indicia including a link to additional information concerning the first event, providing to a memory of the client computer the additional information for display on the graphical user interface upon activation of the link; and outputting a second instruction to the client computer to display the first indicia on the displayed graphic at the geographical location if the geographical location is within the displayed graphic portion of the Earth's surface.

The objects and features of the present invention are also accomplished, as embodied and fully described herein, by a system a system for communicating event information, the system including an event server in data communications with a plurality of client computers used to monitor a plurality of pre-determined events; a software subsystem for outputting a first instruction from the server to display a graphic on a graphical user interface device of each of the plurality of client computers, the graphic including at least a planar representation of a portion of the Earth's surface; a first database in data communication with the event server comprising a plurality of records, each record comprising information about one of the plurality of pre-determined events, wherein each of the pre-determined events is identified from at least one parameter associated with a plurality of indications and warnings and wherein the information comprises a scale value describing a severity of the one of the plurality of pre-determined events and a geographical location describing a location of the one of the plurality of pre-determined events; and a plurality of indicia for use in representing the scale value, each of the plurality of indicia including a link for displaying on the graphic additional information concerning the events upon activation of the link; wherein the plurality of indicia are displayed on the graphic at the geographical location if the geographical location is within the displayed graphic portion of the Earth's surface.

The analytic subsystem involves, on the human side, regional teams of analysts divided among regions of the world to conduct and report on primary open-source analysis of avian influenza or other events, a Supervisory Analyst, if needed, for each region to supervise and assure quality of regional analysts' work, and a Chief Analyst, if needed, to oversee all collection and analysis activities. A Chief Analytic Cell (CAC), if needed, composed of the Chief Analyst and two Deputy Chiefs, oversees the overall analytical quality and issues daily situational awareness reports based on reports from the regional analytic teams. The regions may include, but are not limited to, Southeast Asia, East Asia, Central Asia/Caucuses, Middle East, Eastern Europe/Baltic States, Oceania, Western Europe, Africa and Central/South America.

Regional analysts collect global open source information in accordance with I&Ws training and current reporting requirements. They analyze raw media articles, monitor and analyze outputs from Bayesian models as well as evaluate and dispose of case file summaries. Senior Analysts provide quality assurance and guidance in collection, analysis and reporting of biological events of interest. In addition, Senior Analysts and CAC create and post stratified country alerts. Other methods of administering the human side of the system are also possible and would be equally effective as the embodiment described above.

Preferably, teams of from three to six analysts focus on each of nine global regions outside of the United States, each supervised by senior and chief analysts. These teams of analysts are tasked with using the technologies described below to review local, globally distributed reports and summarize relevant indications and warnings. Their summary reports are forwarded to senior analysts and are stored into a database to be subjected to mathematical modeling and utilized in longitudinal studies. The senior analysts bring to bear their expertise in medicine, public health, epidemiology, climate patterns and other fields and develop daily national assessments from the raw data gathered by the regional analysts. Findings are also checked against established baseline data. This represents a fundamental shift in global biosurveillance: these analysts are not only experts in identifying trends in disease but also in social behaviors associated with these events at the local level. This in-depth understanding enables the analysts to recognize unusual conditions prior to diagnostic confirmation of the biological agent involved.

In one embodiment of the invention, analysts begin their day with Morning Report, where all of the analysts gather to share critical indicators captured overnight or over the weekend. This is a synchronization point for the day, where the participants employ "swarm awareness" for the top tactical issues that everyone needs awareness. The reason for this approach is while an analyst may be responsible for a given region reporting an event of concern, it is more often the rule that the event will be reported by multiple languages from sources in multiple countries with economic, political, or general interest in the region of concern. Often this additional reporting brings valuable information to consider.

The system and method may access over a million pieces of information daily covering every country in the world, and may generate 200 reports per day. Through the system, country- or regional-level Warnings, Watches, and Advisories may be issued in accordance with guidelines agreed upon by research partners in the federal government. There may be multiple Advisories, Watches, and Warnings active on the information processing and analysis subsystem at any given time, with thousands of individual case files of socially disruptive biological events being maintained and monitored daily in over 170 countries (for example) involving 130 disease entities affecting humans or animals (for example). The system maximum load is approximately 3,300 individual case files that may be maintained and monitored, which no previous global biosurveillance system could achieve. Advisories may be shared with user communities through the reporting Watchboard reporting module described herein.

The analytic aspect of the invention leverages an online harvesting engine to move through a codified triage of information to information dissemination within the user community. Raw data is captured and processed. This is the first filter pass and is based on keyword clusters and Bayesian information retrieval models. The second filter step is country level junior analysts who speak the relevant native vernacular reviewing system outputs (and primary sources if it is a language not covered by the system, which covers 18 languages, whereas linguists cover 34 languages; this reflects industry limitations in machine translation). The junior analysts review a set of reporting requirements that are a combination of social disruption I&Ws and a prioritized disease list. This pass results in the creation of an event case file. The event case file is forwarded to the regional senior analyst who checks the report for quality control and then assesses the information from the perspective of the country advisory level reporting requirements. Thus, the user community sees country level advisories but also has the option of drilling into detailed case files with their associated update reports.

Because the system accesses information at a much greater granularity and volume than previously done in global biosurveillance, it may be used to report any and all socially disruptive biological events that are being monitored that may affect humans or other animals. This provides the foundation of a species-agnostic approach to biosurveillance that satisfies the tenets in HSPD-7, -9, -10; NSPD-33, and PL 100-53.

BRIEF DESCRIPTION OF THE SEVERAL VIEWS OF THE DRAWING

Those and other objects, advantages, and features of the invention, as well as the invention itself, will become more readily apparent from the following detailed description when read together with the following drawings, in which:

FIG. 9 is a user interface template for setting up a scheduled search according to the present invention;

FIG. 12 is a diagram of another feature of the user interface of the present invention;

FIG. 16 is a diagram of another feature of the basic reporting template of the present invention;

FIG. 20 is a diagram of an analyst worklist que according to the present invention;

FIG. 23 is a diagram showing another view of the event reporting template of FIG. 21 according to the present invention;

FIG. 25 is a screen-shot drawing showing a list of country- or regional-level event reports grouped by alert levels;

FIG. 26 is an example of a country-level event report for Algeria;

DETAILED DESCRIPTION OF THE INVENTION

Several preferred embodiments of the invention are described for illustrative purposes, it being understood that the invention may be embodied in other forms not specifically shown in any drawings submitted herewith or described below. The system and method of the present invention are illustrated using techniques for biosurveillance of biological events involving humans, animals, and plants; however, the invention is equally useful for other kinds of events that have social disruption potential and that can be detected using various I&Ws contained in open source (or other) documents. For example, the invention may be useful for, among other things, detecting and monitoring political, economic, industrial, and environmental events, as well as civil unrest such as dislocation, riots, violence against property or people; public opinion about any topic of interest including but not limited to political; public policy; religious or entertainment; natural disaster cause and aftermath; natural resource exploitation; and military activity.

I. System Architecture and Work Flow

Figure 1:
FIG. 1 is schematic showing an operational overview of the present invention.

Turning first to FIG. 1, shown therein is an operational overview of the present invention, which involves an information collection center 102, a communications infrastructure 106, and a plurality of information sources 104 around the world. The information collection center 102 may be a single facility within or outside the U.S., or multiple facilities scattered across or outside the U.S. operating together or independently and each operatively connected to each other via one or more communications networks (not shown).

The information collection center 102 receives and examines a continuous stream of information and/or data being generated over a communications infrastructure 106, which, as illustrated in FIG. 1, is represented by individual communications links between the information collection center 102 and the information sources 104. For purposes of this detailed description, the information and data are generally news articles in the form of web document files, such as XML, HTML, ASP, or other compatible file types (see discussion below concerning potentially incompatible file types). Essentially, any open source document, listserve, thread, email, database, etc., is a potential information sources 104.

The communications infrastructure 106 includes a communications network, such as a packet- or circuit-switched network, that is capable of transmitting information and data of any kind. The Internet is the preferred communications network for the present invention.

The information sources 104 shown in FIG. 1 are identified by reference to individual cities, countries, and/or regions where the data originate. There is no geographic or other restriction on where information sources 104 may be located, or where the information and data published or provided by those information sources 104 originate (the actual information and data may originate at the site of the information source 104, or remote from the information source 104). Although FIG. 1 suggests that information sources 104 are located at land surfaces, it is also possible that information sources 104 may be associated with aircraft and spacecraft platforms, as well as submarine platforms. Information sources 104 may be fixed or mobile. The information sources 104 may also be identified by reference to the source or type of information, such as news articles, web portals, really simple syndication (RSS) feeds, and blogs, to name a few.

To illustrate the relationship between the information sources 104 and the origin of information and data, assume the information and data originate at a hospital in Asia that is treating individuals that live proximate to the hospital. Reports of increased hospital visits are broadcast on a website published by a news reporting service in the same city as the hospital. The website is hosted by an Internet Service Provider (ISP) with web servers located in a city 100 miles from the city where the hospital is located. Under that scenario, the information source 104 is the news reporting service website (or, more accurately, the web server that stores the actual website files containing the reported information), although the origin of the information and data is the hospital.

The methodology for identifying information sources 104 includes targeting local, national, and international open source media within various categories, including public health, demographic, historical, socio-economic and social mobilization categories. The Public Health category emphasizes capturing public health websites, agricultural, community-based health-related internet-based sources, official medical, health, information dissemination or other agencies responsible for the provision of basic human and animal health services. The training emphasizes prioritizing collection of these sources in the first stage of examining an area of interest.

The Demographic category includes country-specific guidance on emerging demographic trends, including the appearance of new ethnic communities or "imagined communities" based on migration, economic self-identification, and other social mobilization networks.

The Historical category includes identification of zones of known biological activity, previous hot zones of conflict or social instability, as well as guidance on identifying existing physical infrastructure. Former or current reliance of a country on a specific foreign state or non-state entity, capable of establishing zone(s) of influence within a particular country, are targets for information sources.

The Socio-Economic category emphasizes micro-economic changes, which may influence the emergence or denial of service to new sources appearing within a community. Understanding major micro-economic players in the region presents an opportunity to examine the emergence of (1) physical infrastructure, such as sponsored hospitals, pharmacies, or traditional herbal clinics, and (2) new communities based on micro-loan giving in the area of interest.

The Cross-Reporting category trains analysts to identify cross-reporting trends due to economic, cultural, ethnic or other interests between countries. For example, the system has implemented area-wide regional cross-reporting due to significant ethnic migrant population in South East Asia, the Former Soviet Union and the Middle East, such as in Egypt and Israel.

The Alternative Source category includes Web 2.0 environment-generated blogs, public forums, semi-private forums and lists, which allow increased specificity in targeting a particular population or area of interest.

Example information sources include: NGOs: economic, humanitarian, medical; Companies, corporations in AOR, local offices from multi-lateral corporations; Government websites; Radio/TV sites; Travel blogs; Hospital websites; Game/Wildlife reserves, national parks; Medical blogs; Embedded personnel; Missionary websites, religious sites; Public health/Veterinary health websites; Interest group listserves and/or websites; Disease surveillance networks; Sports team sites; Research organizations (SATVI); Pharmaceutical companies, drug/vaccine producers; Universities, schools; Information systems: HIV/AIDS, TB, malaria, cholera, diarrhea; Water companies; Tribal, insurgent websites; and Ethnic group, tribal diaspora sites.

Example information sources for animal health surveillance include: The sources from which Project Argus retrieves animal reports include: main stream media—a section of the media specifically envisioned and designed to reach a very large audience through internet versions of traditional outlets of news, information and entertainment (i.e. newspapers, television, and radio stations); Public service websites—utilized by industry specific organizations and municipalities to disseminate information that is particularly relevant to a narrow field or location. Official websites, such as CDC, WHO, OIE, Ministries of Health etc, are considered public service websites; Citizen journalism (blogs and microblogs)—administered by an individual or groups of individuals with regular entries featuring commentary and/or descriptions of events or ideas. Most blogs focus on a particular topic of interest. Microblogging, which is usually supported by services like Twitter, disseminates short bursts of information (usually limited to 140 characters or less) through public posts or subscription lists.

Information sources may be identified as being related to specific trigger zones that represent regions where enviroclimatic markers, such as flooding, have historically led to infectious disease outbreaks of primarily water-borne and mosquito-borne diseases. These outbreaks are often associated with infrastructure strain as a result of the enviroclimatic event. Particular attention is paid to information sources that provide information and data about regions where Rift Valley Fever, anthrax and cholera have been reported.

The information and data in news articles or other formats are captured primarily from web sites, as described above, and then formatted into a common encoding representation (typically extensible markup language (XML) or other files), indexed for rapid query access, and stored in an article repository database, as described below.

Figure 2:
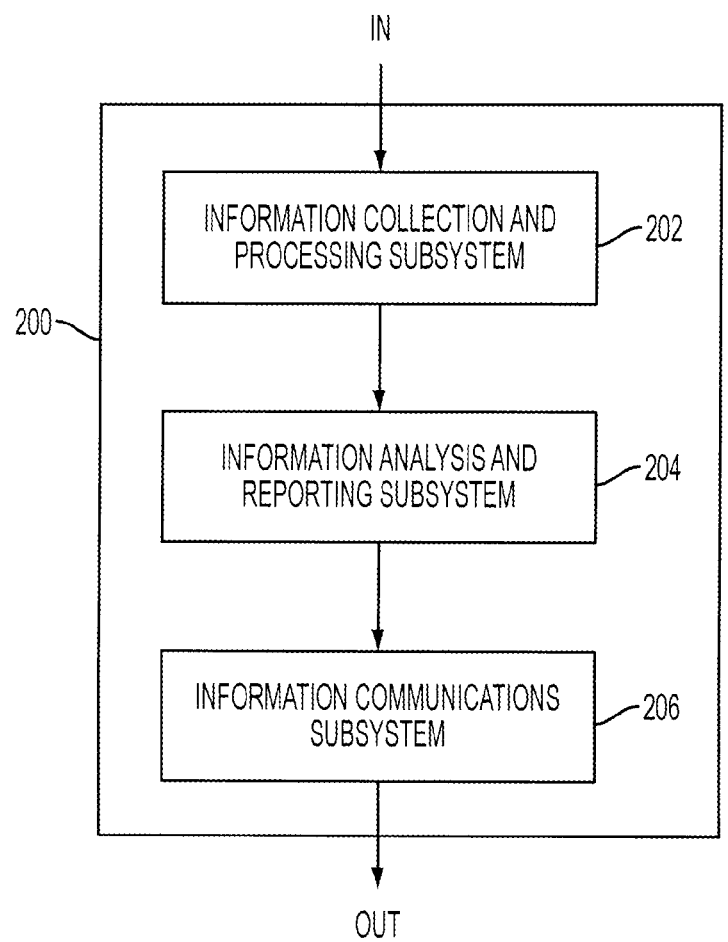
FIG. 2 is a schematic drawing of the basic components of the overall system according to the present invention.

Turning now to FIG. 2, shown therein is a schematic drawing of the basic components of the overall system 200, which includes an information collection and processing subsystem 202, an information analysis and reporting subsystem 204, and an information communications subsystem 206. The inputs to the system 200 are the information and data described above, which are pulled from information sources 104, as well as inputs from analysts that interface with the system 200 (described below). The outputs from the system 200 are various formatted reports communicating event-related information to end users, or simply raw or processed event-related information and data.

Figure 3A:
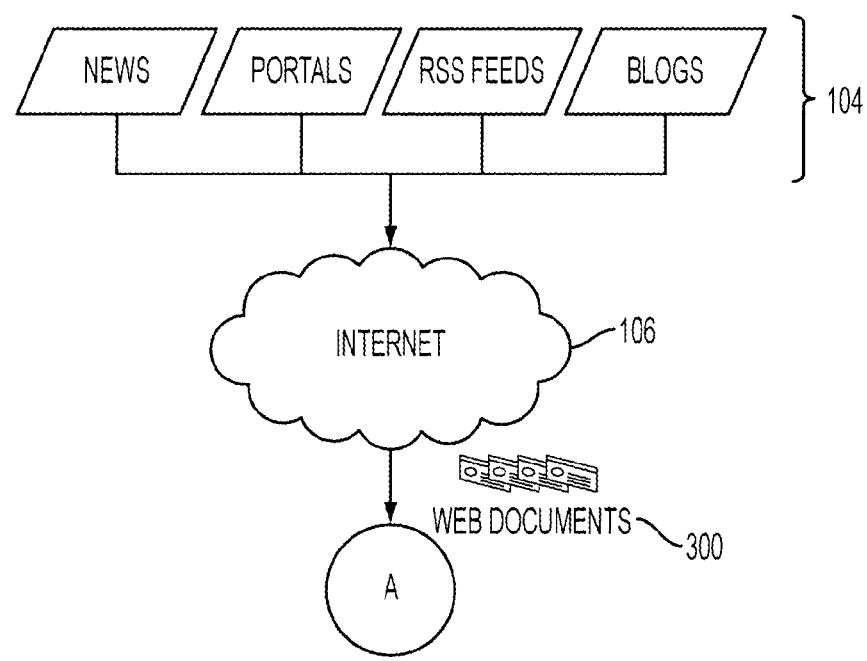
FIG. 3A is a schematic diagram showing the general workflow of information from collection to output according to the present invention.

FIGS. 3A through 3E will now be described. The figures are schematic diagrams showing the general workflow of information from collection to output. Turning first to FIG. 3A, shown therein are exemplary information sources 104 connected to communications infrastructure 106 (the Internet, in this case). The information sources 104 are shown as being sources of web documents 300, which may be any file capable of being transmitted in packets (i.e., in the case of using the Internet Protocol or other packet-switched network to transmit files). Web documents 300 could include hypertext markup language (HTML), XML, portable document format (PDF), text, image, audio, and other file types. A web crawling module (not shown) contains instructions to crawl each of the information sources 104 on a regular schedule to identify those file types. The frequency of the crawl is generally every approximately four hours, but the frequency could be increased to every hour or some other faster frequency if warranted by a particular situation. Those skilled in the art will appreciate that the information sources 104 may include not only web documents 300, but also files created from radio frequency signals intercepted through the air, sea, and space platforms that are translated, transcribed, and/or encoded.

Figure 3B:
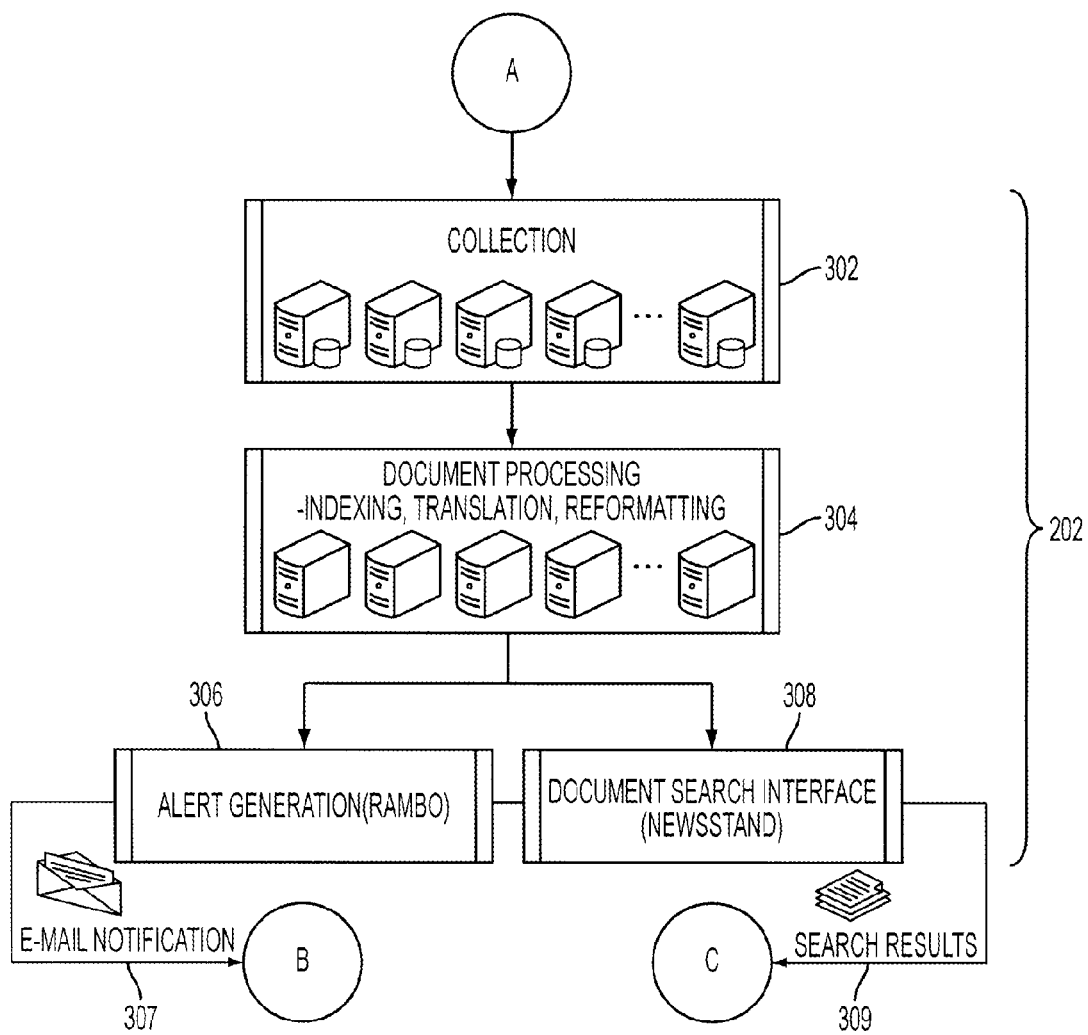
FIG. 3B is a continuation of the schematic workflow diagram of FIG. 3A, and shows the general workflow of information through the information collection and processing subsystem.

FIG. 3B is a continuation of the schematic workflow diagram of FIG. 3A and shows the general workflow of information through the information collection and processing subsystem 202. The subsystem 202 includes one or more document collection servers 302, one or more document processing servers 304, a "RAMBO" alert generation and modeling module 306, and a "Newsstand" document search and reporting interface module 308, which includes a language processing module for foreign language translation (described below).

The document collection servers 302 (also referred to as information source servers), store the data obtained from the information sources 104 after the web crawler identifies new information and data at the information sources 104 and the information and data are downloaded.

The document processing servers 304 perform several functions on the information and data after it has been downloaded from the information sources 104. One function is to translate the title of any documents that are downloaded (the body of the documents are not translated, but on-demand translation is available). Additional functions of the system 200 components will be described in more detail below.

Figure 3C:
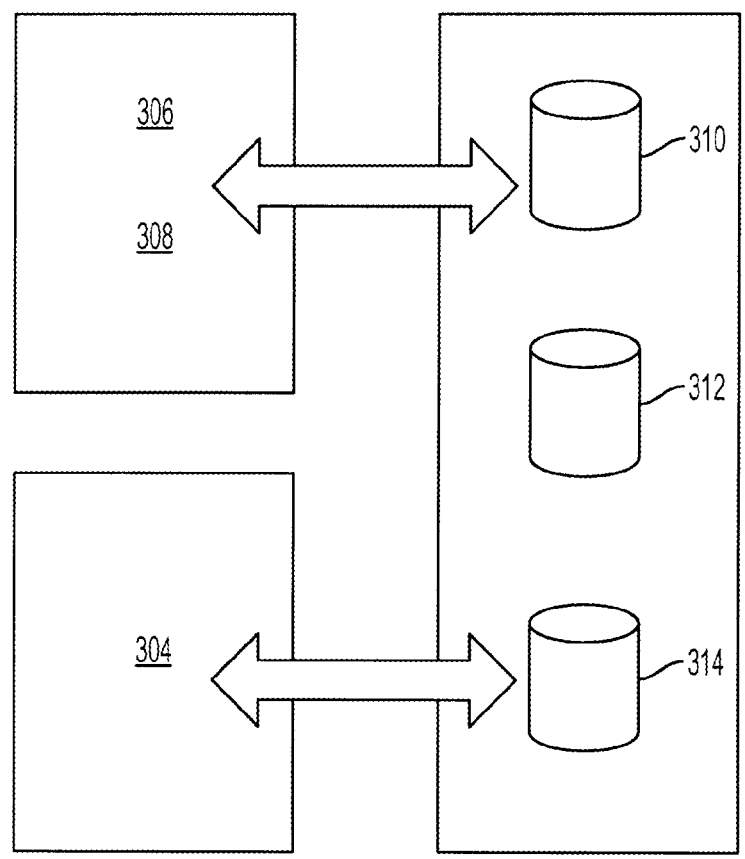
FIG. 3C is a schematic block diagram of the basic database architecture of the present system.

FIG. 3C is a schematic block diagram of the basic database architecture of the system 200. The top block shown on the left represents the aforementioned "RAMBO" alert generation and modeling module 306 and the "Newsstand" document search and reporting interface module 308. The bottom block on the left represents the aforementioned document processing servers 304. The block on the right shows three databases: the article repository database 310, the searchable document/article indexes database 312, and the MySQL relational database management system (RDBMS) database 314. The document search and reporting interface module 308 (i.e., Newsstand) is a Tomcat-based JSP/servlet web application running on a Linux platform using the document index 312 and MySQL database 314.

The article repository database 310 contains the downloaded web document files from the information sources 104, and it maintains records for each document collected from the information sources 104 (or that are generated elsewhere, i.e., a document generated from two or more separate downloaded web documents). As described previously, the actual documents are encoded into a common file format, such as an XML file, but various formats are also possible. Each record includes a document identification, the title, published data, and the "body" of the document. In order to avoid duplicates, as each information source 104 is crawled, the available URLs for downloading are compared to the URL records in a URL database associated with the article repository database 310 to check for duplicates.

The searchable document/article indexes database 312 contains an index of words. Lucene is used for this purpose because it provides, through an inverted index scheme, relatively fast search results. Each document or data stored in the article repository database 310 has one or more keywords of interest. Thus, by identifying keywords, one or more documents having those keywords may be located using the indexes. Currently, the indexes in the articles index database 312 point to over 132 million document files, of which more than about 36 million are stored as English-language documents, with the rest being, in order, Chinese-, Russian-, and then Spanish-language documents. The documents may be in one of 18 languages, or a combination of languages.

The SQL databases contain records of end users, saved searches (described later), the uniform resource locator (URL) associated with the information sources 104, and other records.

Overall, the system 200 involves using about 20 document collection servers 302, document processing servers 304, various web servers (not shown), and other computing devices of various levels of performance running Solaris, Linux, and Windows OS. Java servlets, which are Java classes, are used. The user interface is generated using a combination of HTML, Java server pages, and Java servlets. The Linux operating system runs the MySQL relational database 314. The Tomcat application is used for userid/password authentication (user information is stored in the database 314). Java Database Connectivity (JDBC) is used to communicate with MySQL. The Linux file system is used as the document repository. Apache Lucene is the search engine, but is limited to dealing with text.

Figure 3D:
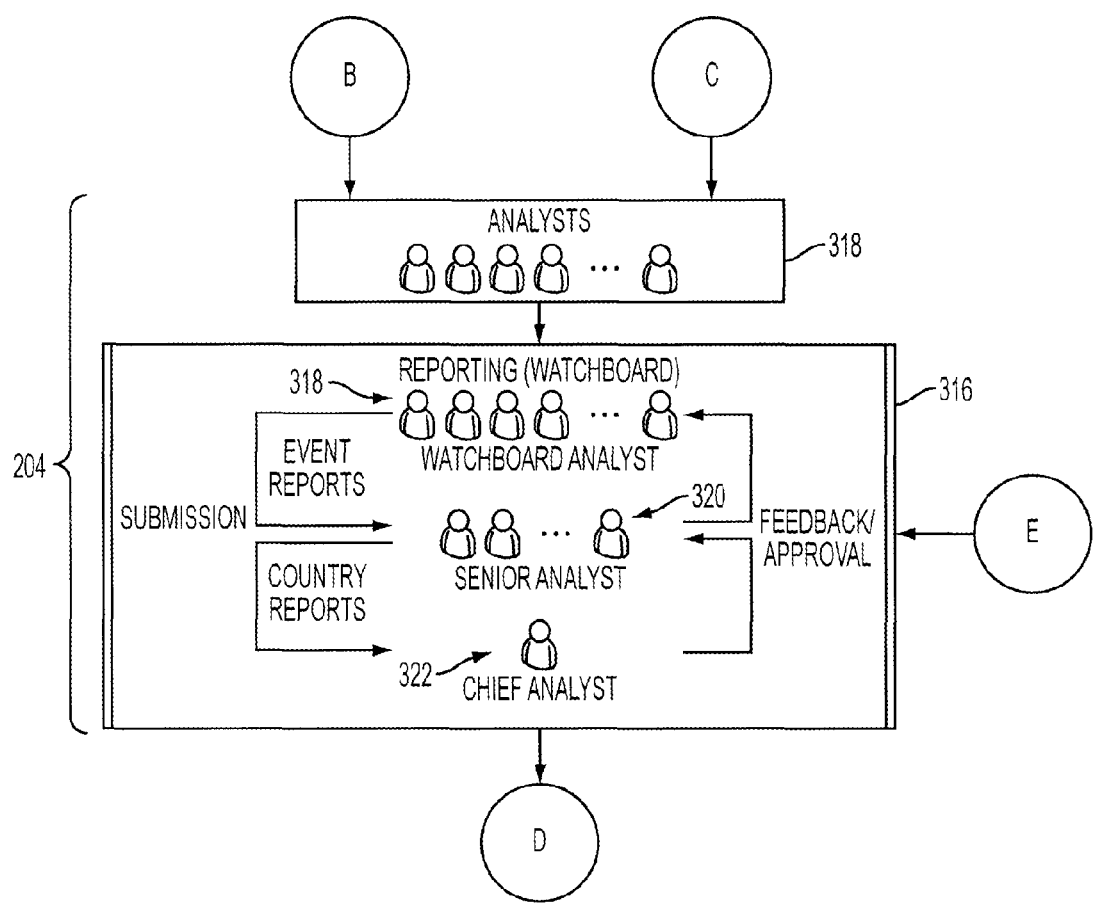
FIG. 3D is continuation of the schematic workflow diagram of FIG. 3B, and shows the general workflow of information through the information analysis and reporting subsystem.

FIG. 3D is continuation of the schematic workflow diagram of FIG. 3B, and shows the general workflow of information through the information analysis and reporting subsystem 204. This subsystem involves using the "Watchboard" search and reporting module 316 by one or more analysts 318, senior analysts 320, and chief analyst 322 (this administrative allocation is for illustrative purposes only). The functions of each of the components of the system 200 will be described with reference to the process flow diagrams below. The search and reporting module 316 (Watchboard) is an ASP.NET web application running on IIS Windows Server running the MS SQL database 314.

Figure 3E:
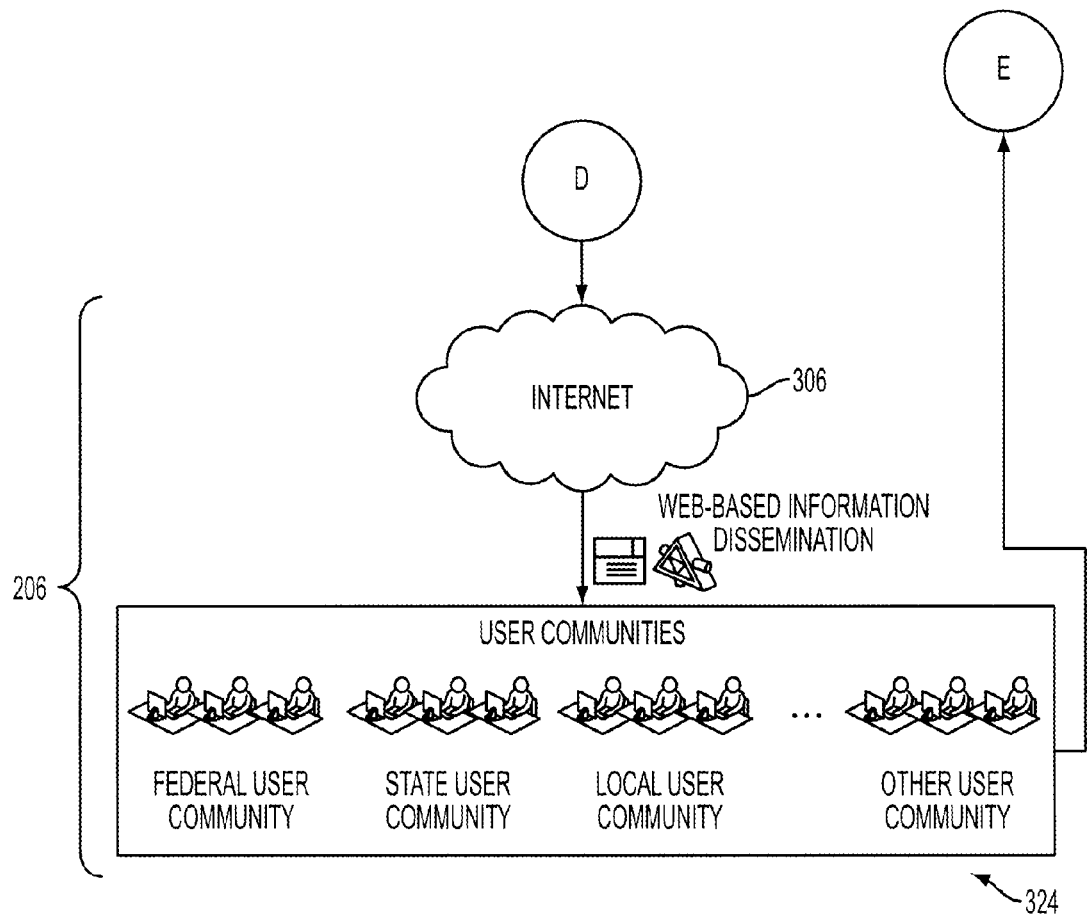
FIG. 3E is continuation of the schematic workflow diagram of FIG. 3D, and shows the general workflow of information through the information communications subsystem.

FIG. 3E is a continuation of the schematic workflow diagram of FIG. 3D, and shows the general workflow of information through the information communications subsystem 206. This subsystem involves end users 324 accessing the system 200 over communications infrastructure 106, such as the Internet, to download web documents, analyst's event reports, maps, geographical information system (GIS) data, and raw or processed event-related information and data.

Figure 4:
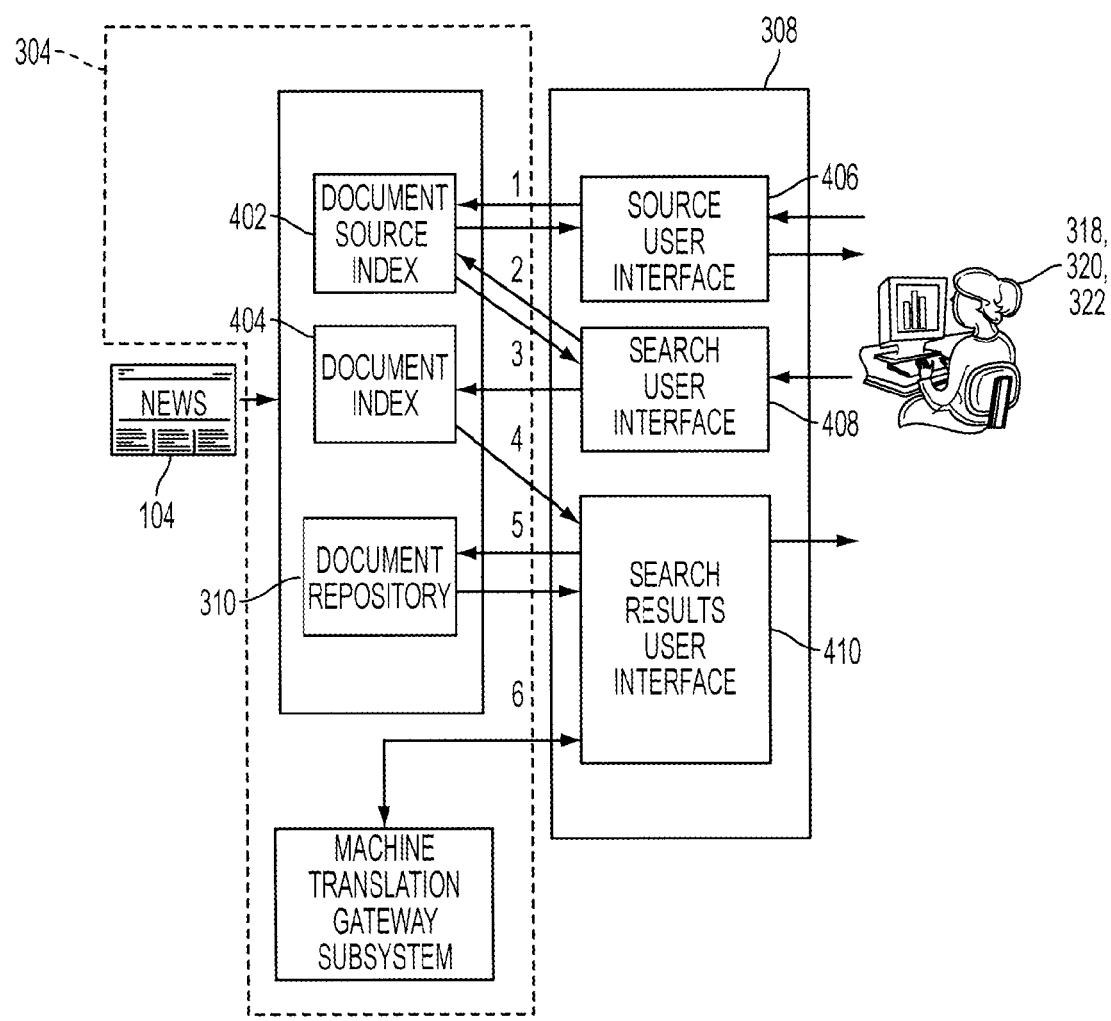
FIG. 4 is a schematic block diagram of the basic architecture of certain aspects of the present system.

FIG. 4 is a schematic block diagram of the basic architecture of certain aspects of the system 200. In particular, certain components of the document processing servers 304 and the "Newsstand" document search and reporting interface module 308 are shown.

The document processing servers 304 provide an enhanced information processing infrastructure with a parallelized architecture for document capturing, formatting, and indexing. It also provides a centralized mechanism for managing the document or article repository database 310 and the data access services. As described above, the document processing servers 304 include a document source index 402, which is an index of the various information sources 104 (generally indexed to their respective URLs), and a document index 404, which is an index relating keywords to document identification numbers for index keyword searching purposes.

The document source user interface 406 allows an analyst 318 (or senior analysts 320 or a chief analyst 322) to access the document source index 402. The analyst 318 runs searches using the document search user interface 408. A list of search hits is returned from the document indexes 404 to the search results user interface 410. The analyst 318 may retrieve the document corresponding to an item in the results list from the document collection servers 310. If document translation is available for the language of the document, the user can translate the document using the machine translation gateway subsystem.

II. System Operation

Figure 5:
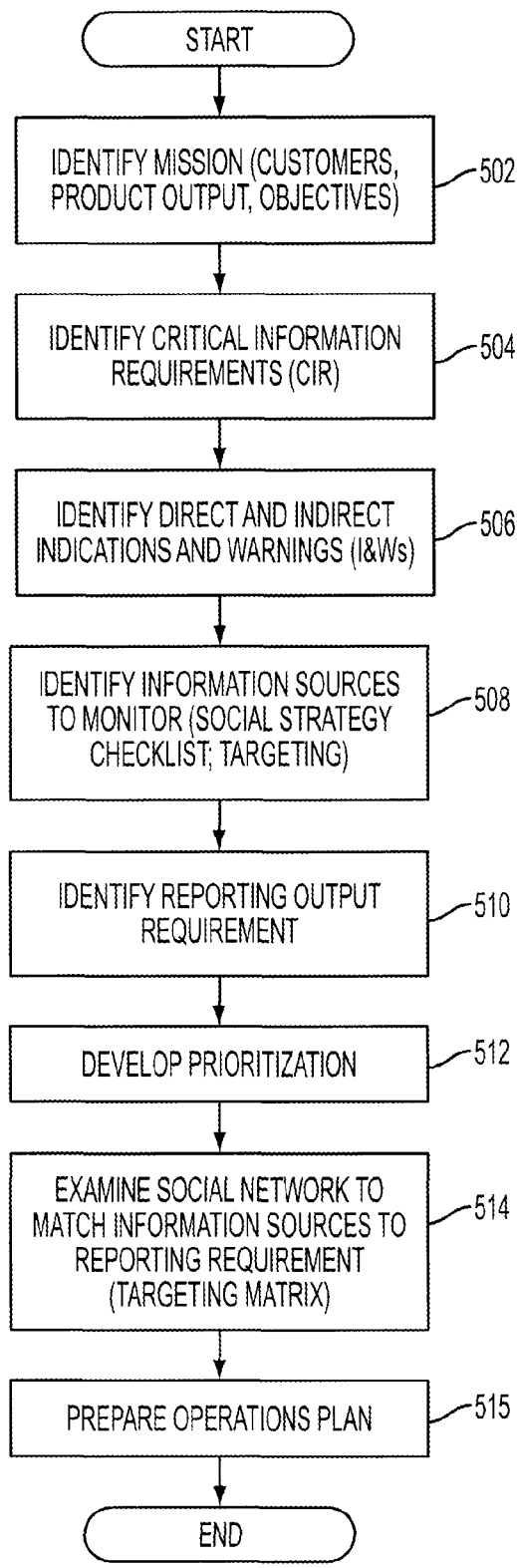
FIG. 5 is an information and workflow diagram of one aspect of the present invention.

The methods of using the system 200 will now be described in detail, beginning with reference to FIG. 5, which is an information and workflow diagram of one aspect of the present invention. Generally speaking, the system 200 collects global open source information and data in accordance with specific I&W training and current reporting requirements. The system is not entirely automated, but requires the expertise of human research analysts who analyze raw media articles, monitor and analyze outputs from Bayesian models as well as evaluate and dispose of case file summaries. More senior analysts provide quality assurance and guidance in collection, analysis, and reporting of events of interest. Still more senior analysts, or chief analysts, create and post stratified country alerts.

Step 502. The overall data collection effort according to the present invention is driven by a comprehensive targeting analysis, which stems from identifying a biosurveillance mission at the outset. The mission could be, for example, to monitor avian H5N1 influenza in Southeast Asia. Tables 1A, 1B, 1C, and 1D below show many of the types of diseases and other events for which the system 200 is or possibly could be used for surveillance purposes.

TABLE 1A

| Disease Events | | | |
|---|---|---|---|
| Priority 1 | Priority 2 | Priority 3 | Priority 4 |
| Pandemic Influenze/Avian influenza | Botulism Bovine Spongiform Encephalopathy | Abrin African horse sickness | Atrovirus *Campylobacter* *Clostridium* |

TABLE 1A-continued

Disease Events

| Priority 1 | Priority 2 | Priority 3 | Priority 4 |
|---|---|---|---|
| Respiratory Disease | (Mad Cow disease) | African swine fever | *perfringens* |
| Anthrax | CCHF | Akabane | Diphtheria |
| Ebola | Creutzfeldt-Jakob | Brucellosis | *E. coli* 0157:H7 |
| Marburg | disease | Chikungunya | Filariasis |
| Plague | Flexal virus | Cholera | Gastroenteritis |
| Rift Valley Fever | Foot-and-Mouth | Contagious bovine | *Giardia* |
| SARS | disease | pleuropneumonia | Hand, foot mouth |
| Smallpox | Guananrito | Contagious caprine | disease |
| Undiagnosed/Unknown | (Venezuelan | pleuropneumonia | Hepatitis |
| Disease | Hemorrhagic Fever) | Dengue | Legionellosis |
| VEE | Hog Cholera | EEE | Malaria |
| XDR-TB | Junin (Argentine | Far Eastern tick- | Measles |
|  | Hemorrhagic Fever) | borne rickettsiosis | Meniningococcal |
|  | Kuru | Glanders | menigitis |
|  | Lassa Fever | Hantavirus | Norovirus |
|  | Machupo (Bolivian | Hendra | *Pertussis* |
|  | Hemorrhagic Fever) | Japanese | Rabies |
|  | Newcastle disease | encephalitis | Ross River virus |
|  | Porcine Respiratory | Meliodosis | Rotavirus |
|  | & Reproductive | Nipah | *Salmonella* |
|  | Syndrome (PRRS) | Psittacosis | Sapovirus |
|  | Polio | Q fever | Shigellosis |
|  | Pox Viruses (except | Rickettsia | (Dysentery) |
|  | smallpox) | prowazekii | *Streptococcus* |
|  | Ricin | Rickettsia rickettsii | Tetanus |
|  | Rinderpest | Swine vesicular | West Nile virus |
|  | Sabia (Brazillian | disease |  |
|  | Hermorrhagic Fever) | Vesicular stomatitis |  |
|  | Tularemia | WEE |  |
|  |  | Yellow fever |  |

TABLE 1B

Other Events

| Priority 1 | Priority 2 | Priority 3 | Priority 4 |
|---|---|---|---|
| Any HS3 event | Complex mutli- | Earthquake (5.0 or | Cyclone/Hurricane/ |
| Any HS4 event | pathogen event | >) | Typhoon |
| Biological weapon use | Diagnostic confusion | Food poisoning | Drought |
| Bird die-off | Flooding (Trigger | Industrial accident | Volcano |
| First report of | Zone) | (chemical) - to Pete | Wild Fires |
| pathogen in new | Tsunami | Industrial Accident |  |
| region |  | (Nuclear) - to Pete |  |
| Healthcare prof./vets |  | Poison |  |
| anxiety or concern |  |  |  |
| Laboratory accident |  |  |  |
| Public panic due to bio |  |  |  |
| event |  |  |  |
| Ventilator depletion |  |  |  |
| Vaccine accident |  |  |  |
| Vaccine or therapeutic |  |  |  |
| failure or |  |  |  |
| compromised |  |  |  |

TABLE 1C

Animal Disease Events

| Priority 1 | Priority 2 | Priority 3 | Priority 4 |
|---|---|---|---|
| avian influenza | Crimean-Congo | African horse | gastroenteritis |
| respiratory disease | hemorrhagic fever | sickness | glanders |
| anthrax | (CCHF) | African swine fever | heartwater |
| Rift Valley fever (RVF) | Nipah virus | alphaviruses | infectious salmon |
| undifferentiated | pox disease | bluetongue | anemia |
| hemorrhagic virus | tularemia | brucellosis | leptospirosis |
| Venezuelan equine |  | bovine spongiform | rabies |
| encephalitis (VEE) |  | encephalopathy | salmonellosis |
|  |  | (BSE), chronic | (except *Salmonella*) |

TABLE 1C-continued

Animal Disease Events

| Priority 1 | Priority 2 | Priority 3 | Priority 4 |
|---|---|---|---|
| | | wasting disease, etc. | screwworm |
| | | classical swine fever (hog cholera) | spring viremia of carp |
| | | contagious bovine pleuropneumonia (CBPP) or contagious caprine pleuropneumonia (CCPP) | encephalitis - all forms |
| | | | tuberculosis |
| | | | West Nile virus |
| | | eastern equine encephalitis (EEE) | |
| | | foot-and-mouth disease (FMD) | |
| | | Japanese encephalitis | |
| | | Newcastle disease | |
| | | peste des petits ruminants (PPR) | |
| | | porcine reproductive and respiratory syndrome (PRRS) | |
| | | Q fever | |
| | | rinderpest | |
| | | swine vesicular disease | |
| | | vesicular stomatitis | |
| | | western equine encephalitis (WEE) | |

TABLE 1D

Plant Disease Events

| Priority 1 | Priority 2 | Priority 3 | Priority 4 |
|---|---|---|---|
| Plant pests/diseases that are new, unknown, mysterious | Pests of special interest to the US | Typical pest outbreaks - this pest often reaches these levels in this area | |
| Plant pests/diseases that are known, but new to a specific area | Pest infestations above normal for that area | Pest Prevention campaigns | |
| Indirect indicators of societal breakdown (food shortages, riots, etc.) | | Enabling conditions for pest outbreaks, e.g. floods, droughts | |
| Specific pests tracked per sponsor's request or users' request and sponsor's approval: Ug99 Plum Pox Virus Planthoppers | | Recovery from pest outbreak | |

The following categories of crops may include Grain, Fruit, Vegetables, Tubers, Nuts, Other food crops, Non-food crops.

Types of plant diseases and stresses include: Aflatoxin, Anthracnose, Ants, Aphids, Army Cutworms, Asian Longhorn Beetle, Bacteria, Bacterial Leaf Streak of rice (Rice Leaf Blight), Banana Mosaic Virus, Bark Beetles, Bees, Beetles, Biotechnology, Birds, Black Leg, Black Market—incl. Smuggling, Black Sigatoka, Blight, Borers, Botrytis, Brown planthopper [*Nilaparvata lugens*], Brown Rot of Stone Fruits, Brown stripe downy mildew of corn, Caterpillars, Cicada, Citrus Canker, Citrus greening, Citrus Variegated Chlorosis, Climate change, Coconut leaf beetle [*Brontispa longissima*], Coffee berry borer, Coffee berry disease, Coffee Rust, Cold, *Colletotricum capsici, Colletotricum* spp., Crop Contamination, Crop Preventative Measures, Downy Mildew, Drought, Emerald Ash Borer, Environmental contamination, Ethanol production, Excessive rain, Farmer protest, Farmer Suicide, Feed Shortage, Flies, Flooding, Food security, Food Shortage, Freeze, Fruit Fly, Fungi, *Fusarium* Spp., Genetically Modified (GM) Crops, Glassywinged Sharpshooter [*Homalodisca coagulata*], Heat, Insect, Kharpra beetle, Late blight, Leaf Roller, Locusts, Mealy bug, Mites, Mold, Moths, Mountain pine beetle, Multiple Crop Diseases/Pests, Mungbean Yellow Mosaic Virus (MYMV), na, Nematode, Other, Panama Banana Wilt, Parasitic Plant, Philippine downy mildew of corn, *Phytophthora* spp., *Phytoplasma oryzae*, Pierce's disease, Planthopper, Potato Cyst Nematode, Potato Wart or Canker, Powdery Mildew, *Ralstonia* spp., Red palm mite, Red Palm Weevil, Rice Grassy Stunt Virus (RSGV), Rice Ragged Stunt Virus (RRSV), Rodents, Root Rot, Rot, Rust, *Schlerotinia* spp. (White Mold), Slugs, Smut, Snails, Southern Wilt—*Ralstonia*, Soybean Rust, Spiders, Storm Damage, Thrips, Tomato leaf miner, Tomato yellow leaf curl virus (TYLCV), Undiagnosed Crop Disease/Pest, Unspecified Pest/Disease, *Verticillium* spp., Virus, Weed—incl. Seeds, Weevil, Wheat brown rust (*Puccinia triticinia*), Wheat leaf rust, Wheat Rust—Not UG99, Wheat Stem Rust UG 99, Wheat Streak Mosaic Virus, Wheat Take-all, White fly, White stem borer, Whitebacked planthopper [*Sogatella furcifera*], Wild Fires, Wilt, Worms.

Step 504. The targeting analysis enables identification of the key required Critical Information Requirements (CIRs) and what information sources 104 can provide such information in a timely and credible manner. The CIRs are typically a list of five to ten (preferably five) statements that define the key items that an end user 324 is primarily concerned about. An example of a CIR is any credible evidence of an act of intentional biological agent release.

Step 506. The targeting analysis also refers to defining the data collection requirements and implied social networks and information providers needed to obtain the data. This is accomplished by identifying I&Ws. I&Ws fall into two categories: direct and indirect. Direct I&Ws refer to explicit local reporting of disease in humans, animals, or plants that may describe epidemiological features of the event. It is important to monitor with a species-agnostic approach. Species tropism exhibited by diseases may give important initial clues as to the diagnosis. For example, prairie dog illness in Colorado is an important indicator of the possible presence (and imminent threat to human health) of plague.

Indirect I&Ws are further subdivided into additional categories such as official acknowledgement, official action, local perception of threat, business practice changes, and integrity of infrastructure. The indicators within these categories are numerous. They enable approximation, over time, of social functioning in the context of a biological event. The key objective in the use of indirect indicators is to provide an assessment of containment status and concurrent level of social disruption.

In a preferred embodiment of the invention, the information collection and processing subsystem 202 generally looks for the following three types of I&Ws in the data being collected from the information sources 104: (1) environmental conditions thought to be conducive to support outbreak triggering; (2) reports of disease outbreaks in humans or animals; and (3) markers of social disruption such as school closings or infrastructure overloads.

Table 2A below identifies typical I&Ws and associated parameters by category (Table 2B, which follows, provides more specific I&Ws related to plant disease events, and Table 2C provides specific I&Ws related to animal health):

TABLE 2A

| Category | Indication and Warning (I&Ws) and Parameters |
|---|---|
| Direct | Reports of human disease |

Diagnostic impression
       Known disease entity
       Unknown/unsure disease entity
    Epidemiological features
       Geography
       Uni-focal (city level and below)
          Building
          Public event
          City
       Multi-focal (beyond city level)
          "Hopping" or non-contiguous geographic involvement
          Multiple cities or regions involved
       Unique/strange clinical presentation
       High morbidity/mortality
       Unexpected appearance of disease in relation to season
       Discrete population involved
       Specific ethnic group
       Nosocomial setting
          Healthcare workers with unusual disease
          Clinical workers
          Lab workers
          Patients contracting unusual disease while in medical facility
    Specific age group
       Pediatric
       Adult
       Elderly
       Occupational TABLE 2A-continued

| Category | Indication and Warning (I&Ws) and Parameters |
|---|---|
| | Reports of animal disease |

Diagnostic impression
       Known disease entity
       Unknown/unsure disease entity
    Epidemiological features
       Unique/strange clinical presentation
       High morbidity/mortality
       Unexpected appearance of disease in relation to season
       Discrete population involved
       Specific species
       Nosocomial setting
          Animal care providers with unusual disease
       Specific age group
          Fetus
          Abortions
          Yearlings
          Adults
       Occupational
       Specific ownership of animals
          Rural
          Commercial
       Geography
       Uni-focal (city level and below)
          Building
          Public event
          City
       Multi-focal (beyond city level)
          "Hopping" or non-contiguous geographic involvement
          Multiple cities or regions involved

| Indirect | Official Acknowledgement |
|---|---|

Acceptance
       Source of reporting
       Low imperative
          Local officials reporting
       High imperative
          Regional/national officials reporting
          International reporting
       Type of reporting
       Acknowledgement of a biological event without explicit declaration of an official concern
       Declaration of outbreak or epidemic
       Declaration of "health alert" or emergency
       Call for international assistance
    Denial
Official Action Official investigation
       Low imperative
          Local civilian government involvement
       High imperative
          Military involvement
          National government involvement
          International organization involvement
    Implementation of countermeasures
       Agriculture countermeasures
       Animal culling
          Sheep
          Cattle
          Birds
          Swine
       Commerce and trade restrictions
          Animal movement/transportation restrictions
          Animal product sale restrictions
          Market closures
          Food kiosk or restaurant closures
       Vector control measures
          Mosquito spraying or fumigation
          Habitat elimination
       Pest control
          Rodent control
       Tick spraying or fumigation or cattle dipping
       Hygiene campaign
       Individuals
          Clothing TABLE 2A-continued

| Category | Indication and Warning (I&Ws) and Parameters |
|---|---|
| | Equipment |
| |   Farm |
| |   Medical |
| |   Industrial |
| | Areas of public congregation |
| |   Businesses |
| |   Schools or child daycare |
| |   Medical facilities |
| |   Public transit |
| |   Places of worship |
| | Official order for personal protection |
| |   Face masks |
| |   Gloves |
| |   Mosquito repellent or bed netting |
| |   Universal Precaution |
| | Activation of pharmaceutical (including vaccines) countermeasure program |
| | Vaccines |
| |   Humans |
| |     Standard vaccines |
| |     Experimental vaccines |
| |   Animals |
| |     Standard vaccines |
| |     Experimental vaccines |
| | Pharmaceutical recommendations |
| | Infrastructure closure |
| |   Individual business closures |
| |   School closures |
| |   Public transit closures |
| |   Farm closures |
| |   Festival closures |
| |   Individual medical facility closure |
| |   Stock market closure |
| |   Government facility closure |
| | Official order to quarantine |
| |   Low imperative |
| |     Individual patient plus contacts quarantine or "house arrest" |
| |     Single animal/single herd quarantine |
| |     Quarantine of an entire farm or commercial facility |
| |   High imperative |
| |     Military or police called in for enforcement |
| |     Quarantine of an entire medical facility |
| |     Quarantine of entire city or region |
| | Propaganda |
| |   Public awareness campaign |
| | Border and Port of Entry closings |
| |   Refusal to allow an aircraft or ship to disembark |
| |   Closure of country's borders |
| |   Military enforcement of border closure |
| | Activation of biosurveillance or screening |
| |   Patient screening and isolation |
| |   Businesses |
| |   Schools or child daycare |
| |   Medical facilities |
| |   Government facilities |
| |   Ports of entry |
| |     Airport screening |
| |     Road checkpoints |
| |     Ships |
| |   Animal and animal product screening |
| |     Farms |
| |     Festivals |
| |     Markets |
| |     Businesses |
| |     Ports of entry |
| |       Airport screening |
| |       Road checkpoints |
| |       Ships |
| | Information suppression |
| |   Closure/censure of media |
| |   Censure of healthcare workers |
| |   Censure of general populace |
| |   Shifts in modes of communication |
| | Prosecution |
| |   Scapegoating |
| |   Penalties against officials for mishandling event |
| |   Prosecution of citizens or industry for information dissemination |
| |   Creation of hotlines to report "rumor mongering" |
| |   Prosecution of citizens or industry for profiteering |
| |   Creation of hotlines to report profiteering or "price gouging" |
| |   Prosecution of citizens or industry for disregarding quarantine |
| Demand for Medical Services | |
| | Increased demand for medical care |
| |   Increased hospital visits or admissions |
| |   Demand for specialized or alternative care |
| |   Military medical care support called to assist civilian medical providers |
| |   Creation of special 'infectious disease wards' |
| |   Traditional healer |
| |     Shamanism |
| | Demand for medications or supplies |
| |   Increased purchasing or use |
| |   Pharmaceuticals including vaccines |
| |   Medical supplies (e.g., face masks, gloves, gowns, disinfectants, ventilators for healthcare provider use) |
| |   Stockpile depletion |
| |   Seeking behavior (e.g., individuals travel to additional areas to purchase medications and medical supplies) |
| |   Innovative behavior (e.g., using bras as face masks) |
| | Mobilization of medical resources |
| |   Mobilization of pharmaceuticals, including vaccines |
| |   Mobilization of medical supplies (e.g., face masks, gowns, ventilators) |
| Local Perception of Threat | |
| | Public "concern" or "anxiety" noted |
| |   Increased use of telecommunication or Internet |
| |   Divestment of pets |
| |   Heightened depression or apocalyptic feelings |
| |   Creation of psychological support centers |
| |   Reports of suicide |
| |     Reports of animal care provider suicide |
| |     Reports of farmer suicide |
| | Hoarding and self preservation behavior |
| |   Changes in consumer behavior |
| |   Increased purchase of staples (i.e., hoarding behavior) |
| |     "Panic buying" |
| |   Pharmaceuticals, herbal medicines or home remedies |
| |     "Panic buying" |
| |   Increased purchase or use of medical supplies for personal use (i.e., public wearing face masks) |
| |   "Panic selling" of livestock |
| |   Avoidance of purchasing animal products |
| |   Avoidance of public places |
| |   Decrease in tourism |
| |   Work and school absenteeism |
| |   Decrease in public transit use |
| |     Shifts in mode of transportation (e.g., from trains and buses to bicycles) |
| |   Decrease in public presence in stores, festivals, and religious sites |
| |   Voluntary evacuation |
| | Public dissent |
| |   Public demonstrations |
| |   Public rioting |
| |   Appearance of newspaper editorials criticizing official response |
| |   Appearance of blogs and chat rooms |
| |   Refusal to comply with government orders |
| Business practice changes | |
| | Changes in pricing |
| | Changes in product advertising campaigns |
| | Black market formation |

TABLE 2A-continued

| Category | Indication and Warning (I&Ws) and Parameters |
|---|---|
| | Integrity of Infrastructure |
| |   Compromise |
| |     Individual business closures |
| |     School closures |
| |     Public transit closures |
| |     Farm closures |
| |     Festival closures |
| |     Pre-emptive stock market closure |
| |     Individual medical facility closure or refusal to see patients |
| |     Medical infrastructure "strain" or at full capacity |
| |   Collapse |
| |     Multiple medical facility closure or refusal to see patients |
| |     Industry-wide closures |
| |     Wide scale economic crisis with gross stock market changes |
| |     Loss of access to basic staples, medications, or medical supplies |
| |     Martial law declared |
| |     Complete social crisis declared |
| |     Complete dependence on international support |
| Enviro-Climatic | Temperature changes |
| |   Increased temperature implying enhanced vector transmission competency |
| |   Decreased temperature (e.g., influenza-like illness) |
| | Precipitation changes |
| |   Increased |
| |     Flooding |
| |     Official Acknowledgement |
| |       Acceptance |
| |         Source of reporting |
| |           Low imperative |
| |           Local officials reporting |
| |           High imperative |
| |           Regional/national officials reporting |
| |           International reporting |
| |         Type of reporting |
| |           Declaration of emergency |
| |           Call for international assistance |
| |       Denial |
| |     Official Action |
| |       Evidence of countermeasures against flooding |
| |       Sandbagging |
| |       Drain cleaning |
| |       Mobilization of resources |
| |         Food and water supply |
| |         Water sanitation and sewage control |
| |         Sandbags |
| |         Personnel |
| |         Medical relief |
| |       Fortification of infrastructure |
| |         Buildings |
| |         Roads |
| |     Response |
| |       Refugee camp formation |
| |       Mobilization of resources |
| |         Food and water supply |
| |         Sandbags |
| |         Personnel |
| |         Water sanitation and sewage control |
| |       Call for international assistance |
| |         International organization on the ground assisting |
| |         Use of military or mercenaries to secure supplies and maintain civil security |
| |     Integrity of Infrastructure |
| |       Compromise |
| |         Business closures |
| |         School closures |
| |         Public transit closures |
| |           Roads |
| |           Railways |
| |           Bridges |
| |           Airports |
| |       Agricultural loss |
| |         Livestock killed |
| |         Crop destruction |
| |       Governmental facility closure |
| |       Medical infrastructure compromised |
| |         Loss of access to safe water |
| |         Work absenteeism |
| |         Shortage of medical supplies |
| |       Utilities |
| |         Electricity |
| |         Blackouts |
| |         Water works |
| |         Access to safe drinking water |
| |         Sewage system failure |
| |     Collapse |
| |       Loss of access to basic staples, medications, or medical supplies |
| |         Famine |
| |       Agricultural loss |
| |         Livestock killed |
| |         Famine |
| |         Crop destruction |
| |         Famine |
| |       Martial law declared |
| |       Complete social crisis declared |
| |       Complete dependence on international support |
| |   Vector population changes (i.e., mosquitoes) |
| |   Decreased |
| |     Drought (e.g., meningococcal outbreaks) |
| |     Official Acknowledgement |
| |       Acceptance |
| |         Source of reporting |
| |           Low imperative |
| |           Local officials reporting |
| |           High imperative |
| |           Regional/national officials reporting |
| |           International reporting |
| |         Type of reporting |
| |           Declaration of emergency |
| |           Call for international assistance |
| |       Denial |
| |     Official Action |
| |       Countermeasures |
| |       Mobilization of resources |
| |         Food and water supply |
| |         Water sanitation and sewage control |
| |         Sandbags |
| |         Personnel |
| |       Control of resources |
| |         Food and water rationing |
| |         Movement of livestock |
| |     Response |
| |       Mobilization of resources |
| |         Food and water supply |
| |         Personnel |
| |         Medical relief |
| |       Call for international assistance |
| |         International organization on the ground assisting |
| |         Use of military or mercenaries to secure supplies and maintain civil security |
| |     Integrity of Infrastructure |
| |       Compromise |
| |         School closures |
| |       Agricultural loss |
| |         Livestock migration |
| |         Livestock killed |
| |         Crop destruction |
| |       Medical infrastructure compromised |
| |         Loss of access to water |
| |         Work absenteeism |
| |         Shortage of medical supplies |
| |       Utilities |
| |         Water works |
| |         Access to water |

TABLE 2A-continued

| Category | Indication and Warning (I&Ws) and Parameters |
|---|---|
| | Collapse |
| | Loss of access to basic staples, medications, or medical supplies |
| |   Famine |
| | Agricultural loss |
| |   Livestock killed |
| |   Famine |
| |   Crop destruction |
| |   Famine |
| | Martial law declared |
| | Complete social crisis declared |
| | Complete dependence on international support |

TABLE 2B

| Category | Indication and Warning (I&Ws) and Parameters |
|---|---|
| Direct | Direct indicators include the traditional epidemiological alerts and markers. Examples of direct indicators include declarations of confirmed diagnostic results; specific, and/or unique or unexpected symptoms; geography; host susceptibility, season of onset; incidence, severity, crop mortality or yield loss measurements. |
| Indirect | Official Acknowledgement: |
| | Official Acknowledgement indicators involve an indigenous government communicating threat information to its citizens and trade partners (commerce). Communications may include acceptance or declaration of an event; denial or no response; and may include a recommendation for a control strategy; or a call for outside assistance |
| | Official Action |
| | Official Action indicators refer to an indigenous government's response to a plant health threat. Possible actions include official investigations; implementation of countermeasures; activation of biosurveillance, survey or screening; information suppression; prosecution of individuals, organizations or companies relating to activities in black markets, crop price gouging, pesticide profiteering, or failure of a government official to handle an event properly. |
| | Demand for Control and Countermeasures |
| | Demand for Control and Countermeasures indicators refer to shifts in supply and demand; mobilization of resources; and economic hardship resulting in farmers unable to pay for supplies and services. This category includes requests for military assistance to control pests; seeking behavior as stockpiles deplete (e.g. traveling to acquire food, seed, or pesticides); innovative mitigation behaviors (e.g. use of vinegar or bleach instead of pesticides); and calls to neighboring regions for assistance. |
| | Local perception of threat |
| | Local perception of threat indicators refer to an increase in anxiety; farmer pleas for assistance; increased suicide rates (common in India), hoarding, panic buying; loss of confidence in government; news editorials, protests, or rioting; and migration to more stable communities. |
| | Changes in business practices |
| | Changes in business practices indicators include changes in import/export patterns; changes in choice of crops grown; business closures; profiteering, black market development; new technology introductions; price increases; and changes in advertising. |
| | Integrity of infrastructure |
| | Integrity of infrastructure refers to market closures; empty store shelves; diminished pesticide, seed or other critical supplies or delays in distribution; riots; establishment of martial law; open rejection by farmers of recommended practices; widespread bankruptcy or starvation; heavy dependence on national or international support. |

TABLE 2C

| Category | Indication and Warning (I&Ws) and Parameters |
|---|---|
| Direct | Reports of animal disease |
| | Diagnostic impression |
| |   Known disease entity |
| |   Unknown/unsure disease entity |
| | Epidemiological features |
| |   Unique/strange clinical presentation |
| |     High morbidity/mortality |
| |     Unexpected appearance of disease in relation to season |
| |   Discrete population involved |
| |     Specific species |
| |     Species jumping |
| |   Nosocomial setting |
| |     Animal care providers with unusual disease |
| |   Specific age group |
| |     Fetus |
| |     Abortions |
| |     Juvenile |
| |     Adults |
| |   Occupational |
| |   Specific ownership of animals |
| |     Backyard |
| |     Commercial |
| |   Geography |
| |     Uni-focal |
| |       One farm involved |
| |       Isolated incidence |
| |     Multi-focal (beyond city level) |
| |       "Hopping" or non-contiguous geographic involvement |
| |       Multiple farms or regions involved |
| Indirect | Official Acknowledgement |
| | Acceptance |
| |   Source of reporting |
| |     Low imperative |
| |       Local officials reporting |
| |     High imperative |
| |       Regional/national officials reporting |
| |       International reporting |
| |   Type of reporting |
| |     Acknowledgement of a biological event without explicit declaration of an official concern |
| |     Declaration of outbreak or epidemic |
| |     Declaration of "health alert" or emergency |
| |     Call for international assistance |
| | Denial |
| | Official Action |
| | Official investigation |
| |   Low imperative |
| |     Local civilian government involvement |
| |   High imperative |
| |     Military involvement |
| |     National government involvement |
| |     International organization involvement |
| | Implementation of countermeasures |
| |   Agriculture countermeasures |
| |     Animal culling |
| |       Sheep |
| |       Cattle |
| |       Birds |
| |       Swine |
| |       Goat |
| |     Indemnity Program |
| |   Commerce and trade restrictions |
| |     Animal movement/transportation restrictions |
| |     Animal product sale restrictions |
| |     Market closures |
| |     Food kiosk or restaurant closures |

TABLE 2C-continued

| Category | Indication and Warning (I&Ws) and Parameters |
|---|---|
| | Vector control measures |
| |   Mosquito spraying or fumigation |
| |   Habitat elimination |
| |   Pest control |
| |     Rodent control |
| |     Tick spraying or fumigation or cattle dipping |
| | Hygiene campaign |
| |   Individuals |
| |     Clothing |
| |   Equipment |
| |     Farm |
| |     Medical |
| |     Industrial |
| | Official order for personal protection |
| |   Face masks |
| |   Gloves |
| |   Mosquito repellent or bed netting |
| |   Universal Precaution |
| | Activation of pharmaceutical (including vaccines) countermeasure program |
| |   Vaccines |
| |     Animals |
| |       Standard vaccines |
| |       Experimental vaccines |
| |   Pharmaceutical recommendations |
| | Infrastructure closure |
| |   Farm closures |
| | Official order to quarantine |
| |   Low imperative |
| |     Single animal/single herd quarantine |
| |     Quarantine of an entire farm or commercial facility |
| |   High imperative |
| |     Military or police called in for enforcement |
| |     Quarantine of entire city or region |
| | Propaganda |
| |   Public awareness campaign |
| | Border and Port of Entry closings |
| |   Refusal to allow an aircraft or ship to disembark |
| |   Closure of country's borders |
| |   Military enforcement of border closure |
| | Activation of biosurveillance or screening |
| |   Animal and animal product screening |
| |     Farms |
| |     Festivals |
| |     Markets |
| |     Businesses |
| |   Ports of entry |
| |     Airport screening |
| |     Road checkpoints |
| |     Ships |
| | Information suppression |
| |   Closure/censure of media |
| |   Censure of veterinarians |
| |   Censure of general populace |
| |   Shifts in modes of communication |
| | Prosecution |
| |   Scapegoating |
| |     Penalties against officials for mishandling event |
| |   Prosecution of citizens or industry for information dissemination |
| |     Creation of hotlines to report "rumor mongering" |
| |   Prosecution of citizens or industry for profiteering |
| |     Creation of hotlines to report profiteering or "price gouging" |
| |   Prosecution of citizens or industry for disregarding quarantine |
| | Demand for Medical Services |
| |   Increased demand for veterinary care |
| |   Demand for medications or supplies |
| |   Increased purchasing or use |
| |     Pharmaceuticals including vaccines |
| |     Medical supplies (e.g., face masks, gloves, gowns, disinfectants, ventilators for veterinarian use) |
| |     Stockpile depletion |
| |   Mobilization of medical resources |
| |     Mobilization of pharmaceuticals, including vaccines |
| |     Mobilization of medical supplies (e.g., face masks, gowns, ventilators) |
| | Local Perception of Threat |
| | Public "concern" or "anxiety" noted |
| |   Increased use of telecommunication or Internet |
| |   Divestment of pets |
| |   Heightened depression or apocalyptic feelings |
| |     Creation of psychological support centers |
| |     Reports of suicide |
| |       Reports of animal care provider suicide |
| |       Reports of farmer suicide |
| | Hoarding and self preservation behavior |
| |   "Panic selling" of livestock |
| |   Avoidance of purchasing animal products |
| |   Avoidance of public places |
| |     Decrease in tourism |
| |     Decrease in public presence in stores, festivals, and religious sites |
| |     Voluntary evacuation |
| | Public dissent |
| |   Public demonstrations |
| |   Public rioting |
| |   Appearance of newspaper editorials criticizing official response |
| |   Appearance of blogs and chat rooms |
| |   Refusal to comply with government orders |
| | Business practice changes |
| | Changes in pricing |
| | Changes in product advertising campaigns |
| | Black market formation |
| | Illegal movement (smuggling) |
| | Integrity of Infrastructure |
| | Compromise |
| |   Farm closures |
| | Collapse |
| |   Industry-wide closures |
| |   Wide scale economic crisis with gross stock market changes |
| |   Loss of access to basic staples, medications, or medical supplies |
| |   Martial law declared |
| |   Complete social crisis declared |
| |   Complete dependence on international support |
| Enviro-climatic | Temperature changes |
| | Increased temperature implying enhanced vector transmission competency |
| | Decreased temperature (e.g., weather-related animal deaths) |
| | Precipitation changes |
| | Increased |
| |   Flooding |
| |   Vector population changes (i.e., mosquitoes) |
| | Decreased |
| |   Drought |

Direct I&Ws are used in traditional international disease reporting by organizations such as GOARN and ProMED that follow the standard epidemiological practice of initial surveillance followed by event verification. Direct I&Ws include diagnostic impression, which refers to whether the causative pathogen has been reported to be known and well understood or unknown. Diagnostic impressions are often ambiguous, particularly when an indigenous society is confronting a pathogen that is either an unrecognized or unexpected agent or is identified initially as well understood, but defies countermeasures thought to have been effective in the past.

Direct I&Ws also encompass epidemiological features. Specific parameters for this marker include unique clinical presentation, geography, high morbidity or mortality, unexpected appearance of disease in relation to season, and discreet population involved. Geography refers to whether an outbreak of disease is unifocal (described in patients or animals located at a single facility) or multifocal (described at multiple facilities or present at a regional level). It also includes descriptions of expected or unexpected propagation patterns, such as the presence of multiple foci when previous experience with a disease dictates a single-point origin for an outbreak or epidemic. Discreet population refers to a high incidence of disease observed in a specific group, such as children or health care workers. As discussed below, the presence of a disease that is multifocal and is directly incapacitating health care workers may point to a compromised medical infrastructure.

Substantial differences between direct markers of biological events affecting animals and direct markers of such events affecting humans have not been observed, except that animals tended to experience disease on farms and were cared for by veterinarians, whereas humans tended to experience disease in hospitals and were cared for by medical workers.

As summarized in Table 2 above, indirect I&Ws include official acknowledgment, official action, demand for medical services, local perception of threat, changes in business practice, and integrity of infrastructure.

Official acknowledgment refers to the behavior of an indigenous government when communicating threat information to its citizens. Three basic messages that governments send have been observed: (1) acceptance or declaration of an event, (2) denial, or (3) no response. It has been observed that public announcements by local officials indicate a unifocal biological event, while those by national officials suggest an epidemic spreading throughout a region. Types of announcements may include explicit declarations of the occurrence of an outbreak, a health alert or declaration of a public health emergency, and calls for international assistance. When a biological event has defied all local countermeasures, announcements become more emphatic and culminate in one or more requests for international assistance.

Official action refers to an indigenous government's response to a biological event. It includes official investigation, implementation of countermeasures, activation of biosurveillance or screening, information suppression, and prosecution:

Local official investigation implies a lower level of official concern regarding a biological event than investigation conducted by national officials or international organizations called in for assistance, such as WHO.

Implementation of countermeasures covers a wide variety of actions, such as vector control measures (like mosquito spraying campaigns), hygiene campaigns (like official orders to disinfect elementary school classrooms), pharmaceutical deployment (like vaccination campaigns), preemptive infrastructure closure (like closure of sites of public congregation, such as festivals, to prevent disease transmission), official orders to quarantine infected individuals, propaganda or public awareness campaigns, and closure of borders and ports of entry to prevent the international spread of disease.

Activation of biosurveillance or screening, such as screening passengers at airports for disease, reveals a shift from passive to active surveillance.

Information suppression is a frequent behavior, irrespective of the country involved. An indigenous government's attempts to deny the presence of a biological threat may stem from concerns about inciting public panic, from the threat's perceived effects on the economy and tourism, and from a lack of official understanding of the threat.

Prosecution of individuals, organizations, and companies occurs for a variety of reasons, including failure of a government official to handle an event properly, unauthorized dissemination of information, profiteering, and disregard of orders to quarantine.

Demand for medical services encompasses parameters that reveal shifts in supply and demand, such as increased demand for medical care, pharmaceuticals, and supplies and mobilization of those resources:

Increased demand for medical care is indicated by a rise in patient presentations at hospitals; demand for specialized care, such as intensive care unit support; and calls for military assistance to support civilian care providers.

Demand for pharmaceuticals and supplies includes increased purchase or use of medications, vaccines, face masks, and gloves. As a biological event progresses to fully defy local countermeasures, depletion of pharmaceutical and medical supply stockpiles is seen. If the public is aware of this stockpile depletion, both seeking behaviors (such as travel to other areas to find medicine) and innovative behaviors (such as using bras as face masks) may be observed. Stockpile depletion will often prompt calls to neighboring regions and countries for assistance and mobilization of resources.

Local perception of threat denotes public awareness of a change in the local status quo of disease incidence. For example, social anxiety is noted when a disease appears abruptly and the public is aware that it may be defying countermeasures. Anxiety is also indicated by increased telephone and Internet use. Heightened incidence of depression or apocalyptic feelings is observed and may prompt special psychiatric intervention, such as the creation of suicide hotlines or psychological support centers. As the media's references to anxiety turn into references to panic, hoarding and self-preservation behaviors are noted, including changes in purchasing behavior (such as panic buying of staples or home remedies) and avoidance of sites of public congregation (such as subway stations, stores, and festivals). As a biological event becomes harder and harder to contain, mass voluntary evacuations are observed. The public's loss of confidence in the government's ability to mount countermeasures against the disease leads to expressions of dissent in newspaper editorials, public demonstrations, and eventual rioting.

Changes in business practice are observed when demand outstrips supply and certain items are at a premium. Changes in prices of staples and medicine are observed, as well as profiteering, changes in advertising, and formation of black markets.

Integrity of infrastructure denotes the progressive strain that occurs when a disease defies countermeasures. Compromised infrastructure is observed when hospitals are reported to be overburdened or inundated with patients, often to the point of creating new disease wards or placing patients in hallways because of a lack of space Infrastructure collapse is observed when hospitals must close or turn patients away because an overwhelming number of patients are presenting, because resources are depleted, and/or because health care workers have been incapacitated by the disease. As an indigenous medical infrastructure progresses from compromise to collapse, a combination of multiple social disruption parameters is observed, indicating a full social crisis: declaration of martial law to preserve basic government functions, open conflict between citizens and government officials, widespread economic damage, and heavy dependence on international support. These parameters indicate maximal social disruption and a loss of ability to control or contain the disease.

It has been recognized that, over time, the identity and characteristics of particular I&Ws may vary with the disease involved and the social routines of the affected culture. Determining what constitutes an I&W thus may depend on understanding local disease baselines and social conditions. Expanded capture media reports from indigenous local sources provide valuable information because these sources reflect timely and qualitative local knowledge of typical and atypical phenomena. This kind of knowledge could be obtained by relying solely on regional news reports.

Step 508. Next, targeting analysis defines the data collection requirements, implied social networks, and information sources 104 needed to obtain the information and data of interest.

Step 510. Output reporting requirements are next identified to satisfy needs of the end users 324 (this step may also be done earlier in the process, after the mission is established, or during subsequent steps).

Step 512. Once the disease-specific and I&W reporting requirements have been established, the next step involves prioritization. For example, a report of diarrhea in a daycare center may take lower precedence than reports the primary trauma care hospital for the city is reporting a sudden inundation of its infrastructure with an unidentified influenza-like illness. Such prioritization is designed to categorize reporting requirements into classes that are easily understood by the end users 324, such as "Warning", "Watch", and "Advisory". Prioritization is dependent upon, and partly defined by the end users 324, whether for internal monitoring purposes or to provide reporting to the healthcare community or the general public. Prioritized reporting requirements drive the operations tempo, where "Warning" implies a tactical, near real time reaction by the analyst versus an "Advisory" that may be monitored over the course of a week. In other words, this categorization is an easy way to impart the severity and importance of the report to the user community.

Step 514. Once prioritized reporting requirements have been established, an examination of social networking may need to be conducted to cross-match the requirements to specific information and data sources. The product of this analysis is referred to as a targeting matrix. For example, if a key direct indicator is reports of disease in rodents, then one may need to consider building a network of reporting that includes the local sanitation authority. If a key indirect indicator is local depletion of ventilator supplies, then one may need to build a relationship with the local distributor of ventilators as well as medical facilities that use ventilators.

Step 515. The next step, developing an operations plan, draws together all of the aforementioned steps into a document that defines precisely how the mission will be executed, from mission statement, to CIRs, prioritized reporting requirements, operation tempo modes, communication channels that include the social network of reporting, and so on. While the document itself eventually becomes a desk reference for the biosurveillance analyst, it is a "living" document that is modified to reflect changes in operational requirements and refinements in the analytic process over time.

Figure 6A:
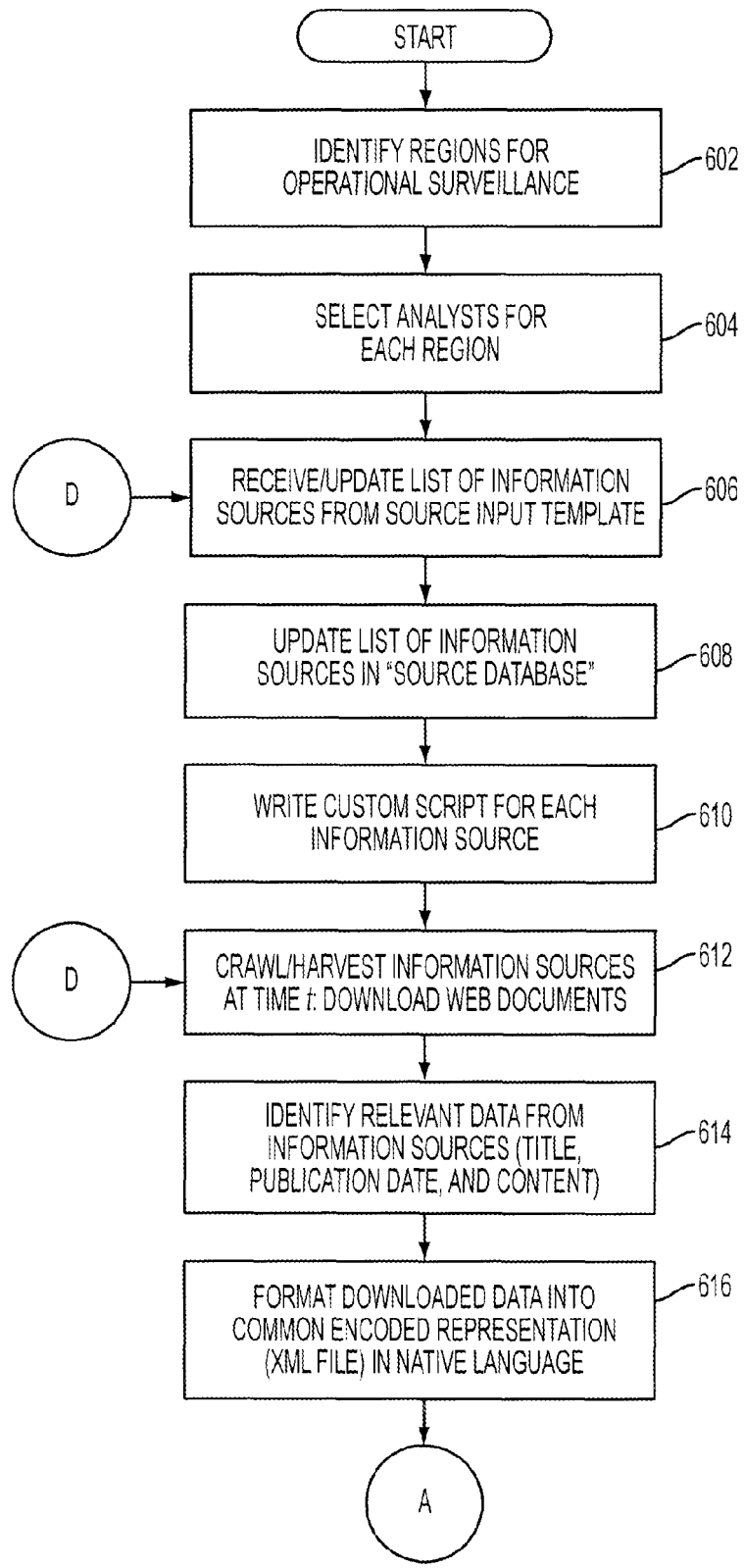
FIGS. 6A and 6B are information and workflow diagrams of another aspect of the present invention.
Figure 6B:
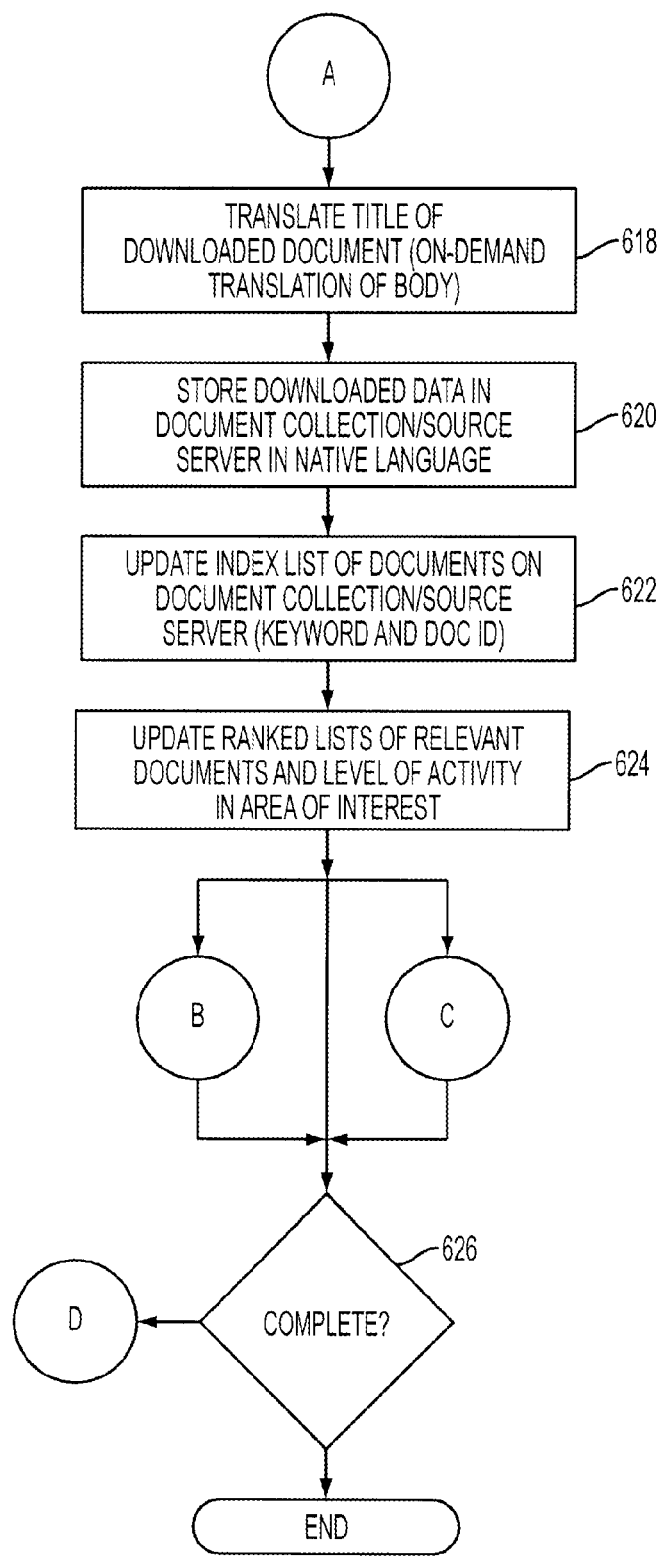

Turning now to FIGS. 6A and 6B, shown therein is an information and workflow diagram that illustrates the steps in the process after those described immediately above.

Step 602. The system 200 currently targets local, national, and international open source media information sources 104. Because those information sources 104 may be defined geographically, the world is broken into countries and regions for operational surveillance purposes: Southeast Asia, East Asia, Central Asia/Caucuses, Middle East, Eastern Europe/Baltic States, Oceania, Western Europe, Africa and Central/South America (a tenth region, North America, is currently not under biosurveillance). The system 200 includes, in one embodiment, nine regional teams consisting of thirty-six analysts 318, that conduct and report on disease occurrences worldwide. There are nine senior analysts 320 for each region, which supervise and assure quality of the analysts' 318 work. A chief analyst 322 oversees the overall analytical quality. If necessary, a daily situational awareness report based on reports from the nine regional analytic teams may be generated.

Step 604. It is important to select analysts 318 who have an understanding of the specific countries or geographical regions in which biosurveillance is to be conducted, because cultures within those countries and regions have unique languages, customs, political structures, communications infrastructures, and other unique properties and factors that may not be apparent to analysts 318 who are less familiar with the specific countries/regions under surveillance.

Step 606. A checklist for identifying information sources 314 may be used once a mission has been identified. The checklist may include categories defined by public health, demographic, historical, socio-economic and social mobilization parameters, as follows:

The public health category emphasizes capturing public health websites, agricultural, community-based health-related internet-based sources, official medical, health, information dissemination or other agencies responsible for the provision of basic human and animal health services. Collection of information from these information sources 314 is the first stage of examining an area of interest;

The demographic category includes country-specific guidance on emerging demographic trends, including the appearance of new ethnic communities or "imagined communities" based on migration, economic self-identification, and other social mobilization networks;

The historical category includes identification of zones of known biological activity, previous hot zones of conflict or social instability, as well as guidance on identifying existing physical infrastructure. In addition, former or current reliance of a country on a specific foreign state or non-state entity, capable of establishing zone(s) of influence within a particular country is provided. Internet sourcing related to social mobilization networks and zones of historical, demographic, and socio-economic activity will be most active during an ongoing event and in the post-event response;

The socio-economic category emphasizes micro-economic changes, which may influence the emergence or denial of service to new sources appearing within a community. Understanding major micro-economic players in the region presents an opportunity to examine the emergence of (1) physical infrastructure, such as sponsored hospitals, pharmacies, or traditional herbal clinics, and (2) new communities based on micro-loan giving in the area of interest.

The cross-reporting category identifies cross-reporting trends due to economic, cultural, ethnic or other interests between countries. For example, Russian cross-reporting due to significant Russian ethnic migrant population in South East Asia, the Former Soviet Union and the Middle East, specifically in Egypt and Israel, is provided;

The alternative source category includes web 2.0 environment-generated blogs, public forums, semi-private forums and lists, which allow increased specificity in targeting a particular population or area of interest.

An analyst 318 may suggest an information source 104 to be included on the document source index 402 by entering the URL of the information source 104 into a template (described later). The template is an intake form that is used by programmers to develop scripts to capture information and data from the proposed new information source 104.

Step 608. The list of information sources 104 to be crawled is updated and stored in the appropriate database.

Step 610. In order to easily search all of the documents downloaded from the information sources 104, the documents are preferably encoded to a common format. Thus, once an information source 104 is identified, a unique script is written for that information source 104 that captures the title, publication date, and "body" of the published files that are available from the information source 104. If the web document is an HTML file, it is relatively easy to locate the title, date, and body from the metadata associated with the file.

Step 612. For some information sources 104, all of the new/updated information and data that are available may be downloaded and then searched at a later time. For example, if an RSS feed is used, the feed provides all the new/updated information added to a website, regardless of whether it is relevant to the specific I&Ws/parameters. In the case of a website without RSS, the site is crawled according to a pre-determined schedule, as previously described.

Step 614. The unique script associated with a particular information source 104 is executed to extract the relevant data for subsequent analysis purposes.

Step 616. The extracted data are then encoded into a new format and saved to a new file. The encoded file format is preferably UTF-8 encoding. It is contemplated that other encoding formats could also be used, such as a markup language, or it could be unformatted text, or other format. The original language of the document is preserved; thus, if the downloaded information or data is in Spanish, the encoded file will also be in Spanish.

The extracted data may also be used to develop and train a model for classifying the text associated with downloaded information and data, using the text in the title and the body of the extracted data. A training corpus consisting of many articles in the application field (e.g., 1,000 or more online articles) that have been manually categorized into one of the predefined classes (e.g., "relevant" and "irrelevant" in terms of the biosurveillance goal) is used to for a machine learning model for automatically classifying newly published articles. This is accomplished as follows:

First, convert each article into a feature vector to apply machine learning algorithms (e.g., support vector machine):

a. Text in title or body is tokenized into words, where the white space or other selected symbols (e.g., period, comma, quotation, etc.) are used to delineate text. If text is in language without explicit word boundaries, e.g., Chinese, Japanese, and Korean, instead of words, we use character n-grams (consecutive n characters in text) for all n≤N selected empirically for each language. If applicable, words/n-grams may be normalized, e.g., English words are represented in lower-case. Resulting words/n-grams with a label to indicate section (title or body) are considered as feature candidates, e.g., "title:death" and "body:infected";

b. Among feature candidates in each article, ones in the body section are filtered based on their positions. Specifically, only those that can be found within the first k words (or characters for character n-grams) in body are kept for further processing, where k is empirically selected. (Alternatively, features from body may be supplemented with positional information, and all kept for further processing, e.g., "body:k<=100:infected" and "body:k<=500:infected");

c. After processing all articles in the training corpus and acquiring document frequency (DF) for each feature candidate, information gain (IG) is calculated and ones with high IG values are recognized as features. The number of features to be selected is determined empirically;

d. Each of the selected features is uniquely assigned with a position number, e.g., "disease" at the position 1, "death" at the position "2", etc. Then, each article is represented as a feature vector, where the presence of a feature in the article is coded as a weighted frequency of the feature at the corresponding position in the feature vector.

2. Build a machine learning model:

a. Provided with a set of training instances consisting of feature vectors, a machine learning algorithm is applied to derive an article classification model. There can be many algorithms applicable to this task, but Perceptron with margin, support vector machines (SVM), and multinomial naïve Bayes, regularized logistic regression have been tested.

Step 618. If the original information and data are in a language other than English, the title of the downloaded web document is automatically machine translated into English if machine translation service is available for the particular language. It is contemplated that manual translation may also be used.

Step 620. The encoded file is then saved in the article repository database 310.

Step 622. Once a new XML file is added to the article repository database 310, the document index 404 is updated to include the words associated with the subject and body elements of the new XML file, making subsequent searches of the keywords within the new XML file possible.

Other sources of information may be accessed manually, and include, but are not limited to, websites available from ProMED, GIDEON, WHO, CDC, and OIE, to name a few.

Step 624. If a particular country or region is under surveillance, a ranked list of relevant documents may be updated for analysts to easily identify the level of activity in an area of interest.

Step 626. The next sequence of processes in FIG. 6B, identified as connector nodes B and C, are conducted in parallel or in series, and will be described below. Once those sequences are complete, the process returns to a decision step, in which the system 200 determines whether additional steps are required to be executed. If not, the system 200 is terminated. If additional steps are warranted, the system 200 branches back to one of several earlier steps as indicated by connector node D in FIG. 6A.

Figure 7A:
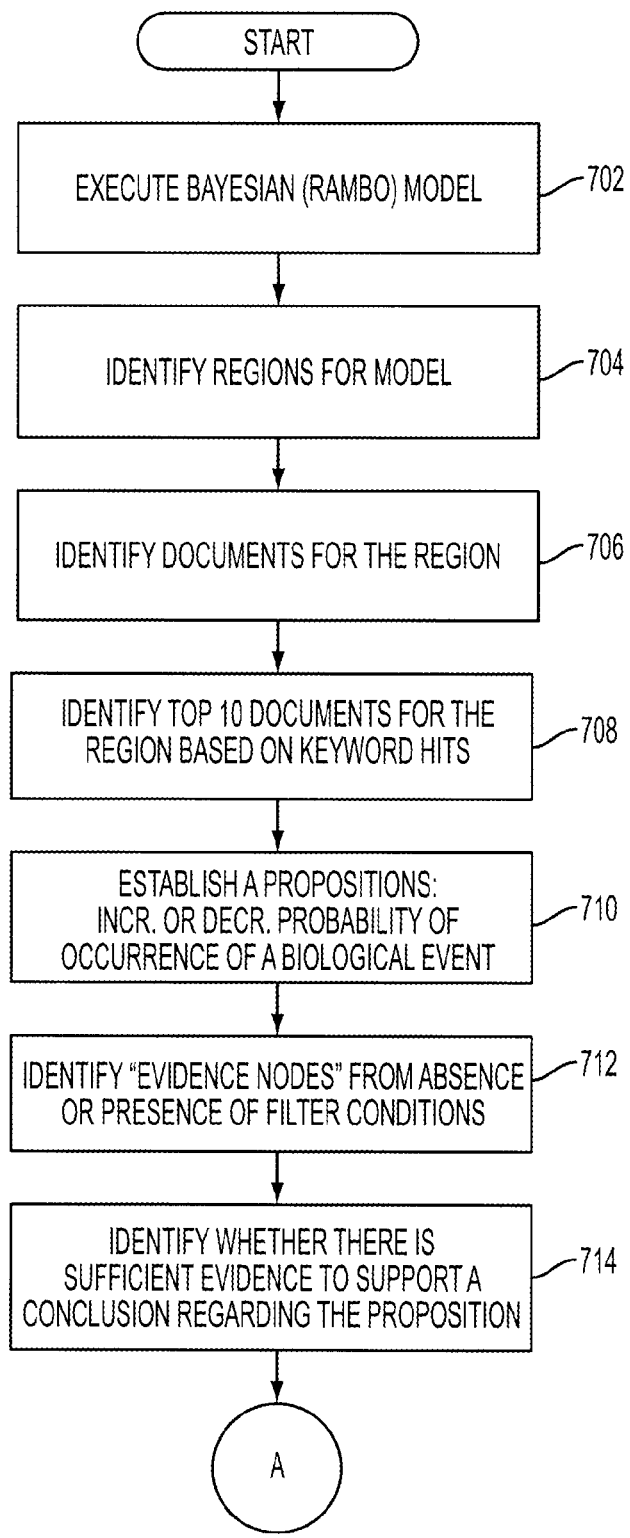
FIGS. 7A and 7B information and workflow diagrams for the connector node B shown in FIGS. 6A and 6B.
Figure 7B:
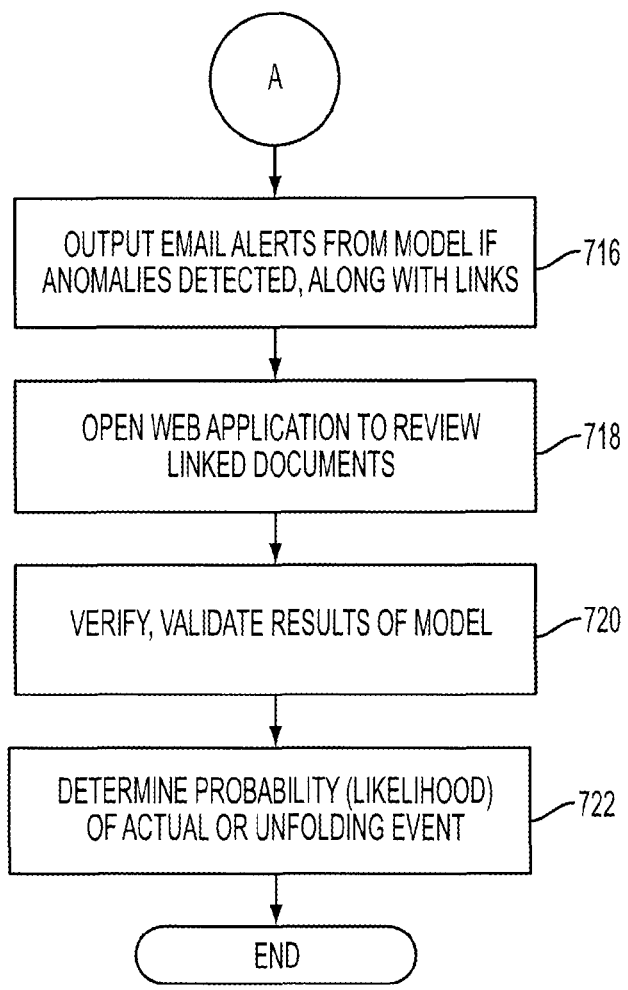

FIGS. 7A and 7B are an information and workflow diagram for connector node B shown in FIG. 6B.

Step 702. The system 200 automatically executes the RAMBO alert generation and modeling module 306. No manual intervention is required, except to input modeling parameters and model initial conditions, as necessary. The alert generation and modeling module 306 analyzes the information and data in the article repository database 310, and outputs one or more ranked lists of articles of potential interest.

Step 704. The module 306 may be set up to analyze a particular event, city, region, country, or other geographical limit. The module 306 was developed using Bayesian casual models as an information retrieval mechanism for events associated with complex keyword clustering. The module 306 provides a "back-stop" mechanism whereby analysts 318 who are busy searching at the more sensitive, individual keyword level (described above and below) do not fail to notice a larger, more complex evolving event. This is an operational safety mechanism to ensure that "Stage 4" biological events of possible transnational threat potential are not overlooked.

Step 706. The module 306 scans all encoded files that have been downloaded from the information sources 104, and identifies those that are relevant to a particular event, city, region, country, or other geographical limit provided for in the previous step. This is an automatic routine that may be executed as soon as new data are downloaded from the information sources 104.

Step 708. The module 306 maintains an index of the top ten (or more or fewer) downloaded documents for a particular area of interest based on keyword hits. The module 306 issues an email notice 307 to the analysts 318, which includes links to the top documents so that the analysts 318 may open the files and review them.

Step 710. The module 306 is based on Bayesian probability, which interprets "probability" as "the degree of belief (or strength of belief) an individual has in the truth of a proposition." The analysts 318 establish a new proposition, i.e., the probability of occurrence of a biological event at any given moment based on the most recent data being downloaded from identified information sources 104. The propositions may be of the form of increasing or decreasing degrees of belief in the occurrence of a biological event such as a plant, animal, or human disease outbreak. The modeling makes use of custom software developed by The MITRE Corporation to implement the Bayesian modeling, and some tool-specific data management and configuration services. Currently, the system 200 includes several Bayesian models in multiple languages running in parallel or in series.

Step 712. The Bayesian model uses data obtained from queries of the documents to drive "evidence nodes" in the model, which are used to detect the presence or absence of certain conditions reported in the news articles.

Step 714. If certain evidence is found, that drives a "decision node" to conclude that there is or is not sufficient evidence to support an intermediate or final conclusion regarding the aforementioned proposition.

Step 716. The module 306 outputs email alerts if anomalies are detected for a given location being monitored based on the data obtained from the information sources 104 relevant to that location. Those email alerts may be separate or part of the aforementioned email notices 307. An anomaly may be detected based on simple rules, e.g., an increase in the number of keywords found in relevant documents obtained from information sources 104 above a threshold value, or percentage increase above an established baseline.

Step 718. When an analyst 318 clicks on one of the email links, a web application is opened which provides an interface for the analyst 318 to view the actual web documents containing the keywords of interest for the model found to be relevant to the aforementioned proposition.

Step 720. The results of the model are verified and validated by reviewing the top web documents identified by the model as suggesting whether a new or developing event is actually unfolding or not. Usually, this initial filtering step forms part of the daily event reporting by the analysts 318.

Step 722. If the model does identify web documents that suggest that a new or developing event is unfolding, the analyst 318 may estimate a probability of such occurrence based on experience and historical information about the area of interest. Thus, the analyst 318 may conclude that there is a high probability of an unfolding event based on his or her review of the top ten documents.

Figure 8:
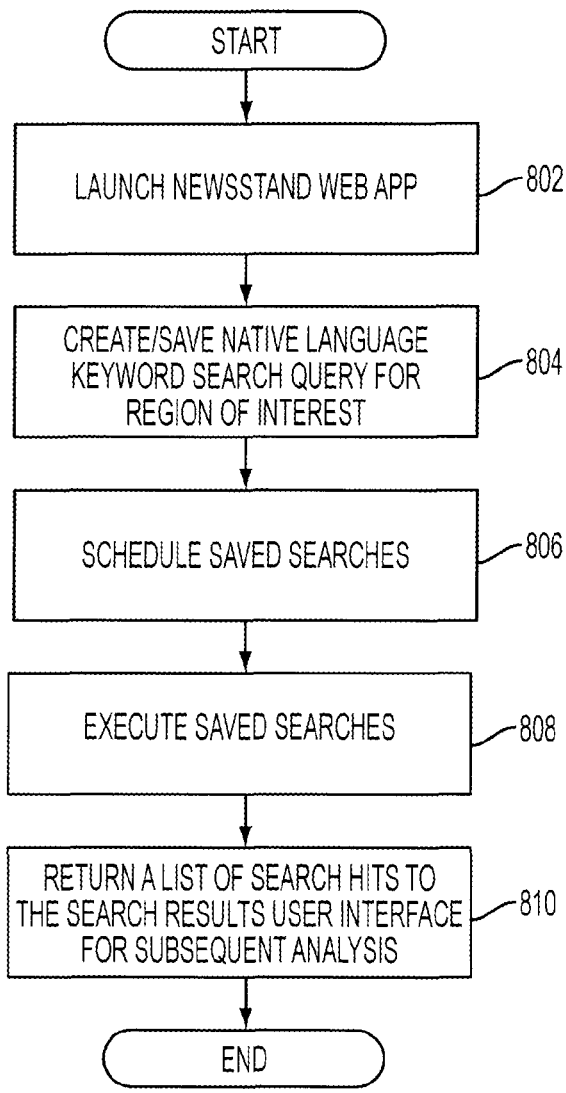
FIG. 8 is an information and workflow diagram for the connector node C shown in FIGS. 6A and 6B.

Turning now to FIG. 8, shown therein is an information and workflow diagram for connector node C shown in FIG. 6B. After analysts 318 refer to the Bayesian model outputs that prioritize articles for review, the analysts 318 use the "Newsstand" document search and reporting interface module 308 as a second filtering step to identify relevant event-related information.

Step 802. If the "Newsstand" document search and reporting interface module 308 is used, the web application is first launched.

Step 804. The "Newsstand" document search and reporting interface module 308 can execute pre-established saved searches automatically, or manually. New searches may also be created and saved. The searches target both direct indicators, such as disease names or words like "outbreak," and indirect indicators, such as "panic", "shortage", or "black market." For example, a search for information and data relating to avian influenza might use the following query, either entered as a new search or saved as a previous search that is re-run:

H5 OR H7 OR HPAI OR "avian influenza" OR "bird flu" OR "avian flu" OR influenza OR flu OR "H5N1" OR "dead bird" OR "bird die-off" OR pandemic OR "influenza-lie" OR "avian flu" OR pathogenicity OR "human-to-human" OR person-to-person" OR tameflu OR pneumonia OR oseltamivir Other common searches may be saved for the following events: "laboratory accident", "biological weapon use", "ventilator depletion", "disease/healthcare workers", "unknown disease", "flooding", "natural disasters", "industrial accident", and for the following I&Ws: "quarantine", "animal die off", "declared event", "disease symptoms", "official acknowledgement", etc. (see Tables 1 and 2 for I&Ws that may identify parameters, or more specifically keywords, for use in searches).

Figure 9:
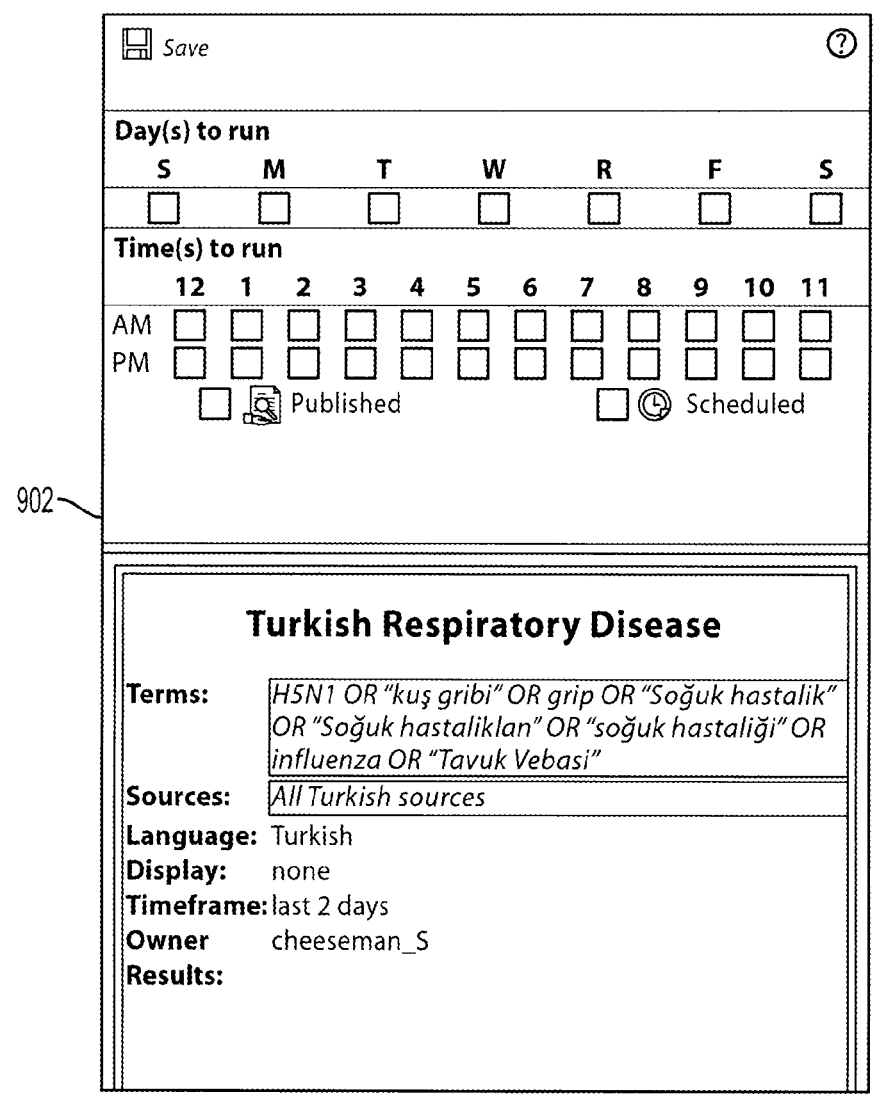

Step 806. Keyword searches may be scheduled to be execute on any frequency established by the analysts 318. Scheduled saved searches are run by Moab, a job-scheduling and management package targeted at a cluster environment. The trigger for a scheduled saved search is an event in the EVENT_SCHEDULE table that corresponds to a saved search. The scheduled saved search is run at the scheduled time and date on one of the cluster nodes, and results are saved in the database for the user. Log files are kept for each run. Only the last two results are saved. FIG. 9 shows an interface template 902 for setting up the scheduled search. The template 902 includes fields for search day, time of day, search terms (Boolean or otherwise), sources to be searched, language, display, timeframe for documents, and userid.

Step 808. Saved and scheduled searches are executed according to the EVENT_SCHEDULE table criteria.

Step 810. The web application then returns a list of search hits to the search results user interface 410.

Figure 10A:
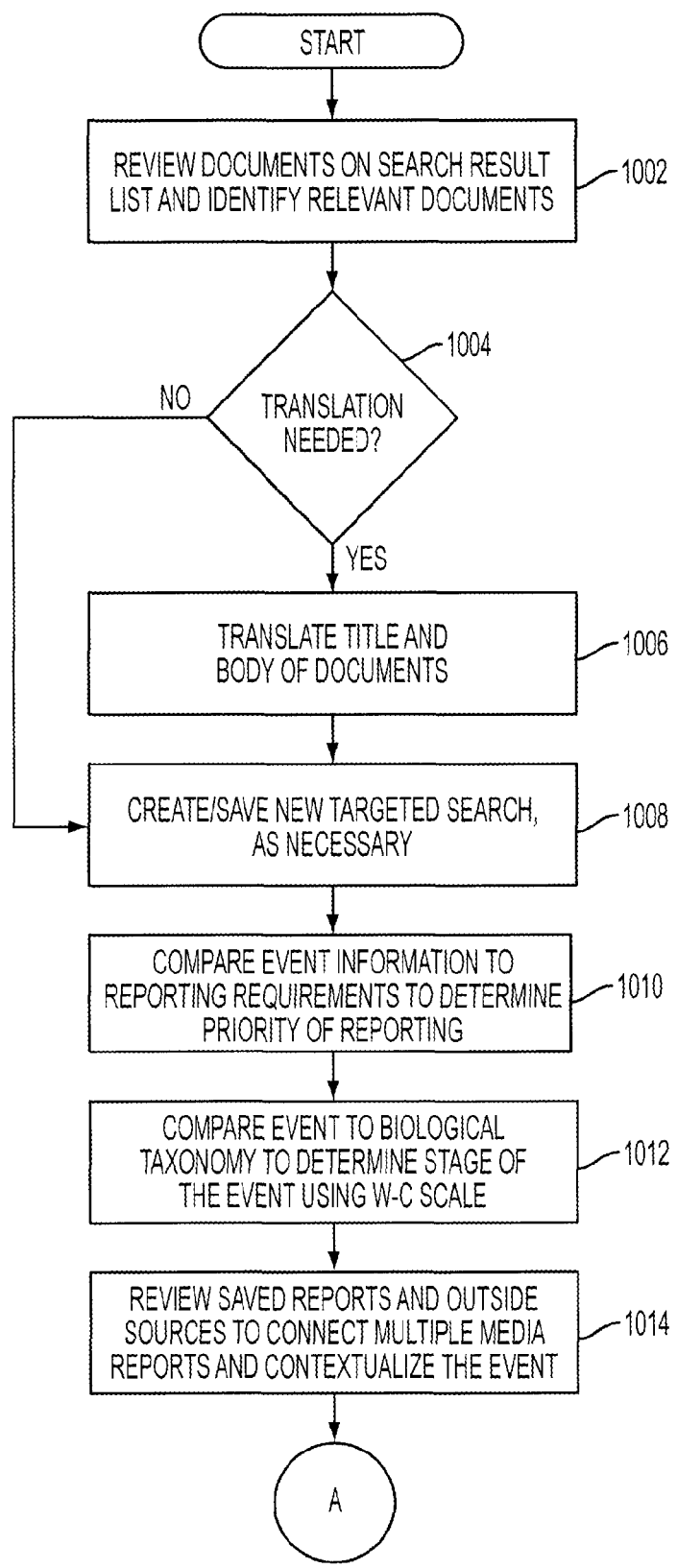
FIGS. 10A, 10B, and 10C are information and workflow diagrams of another aspect of the present invention.
Figure 10B:
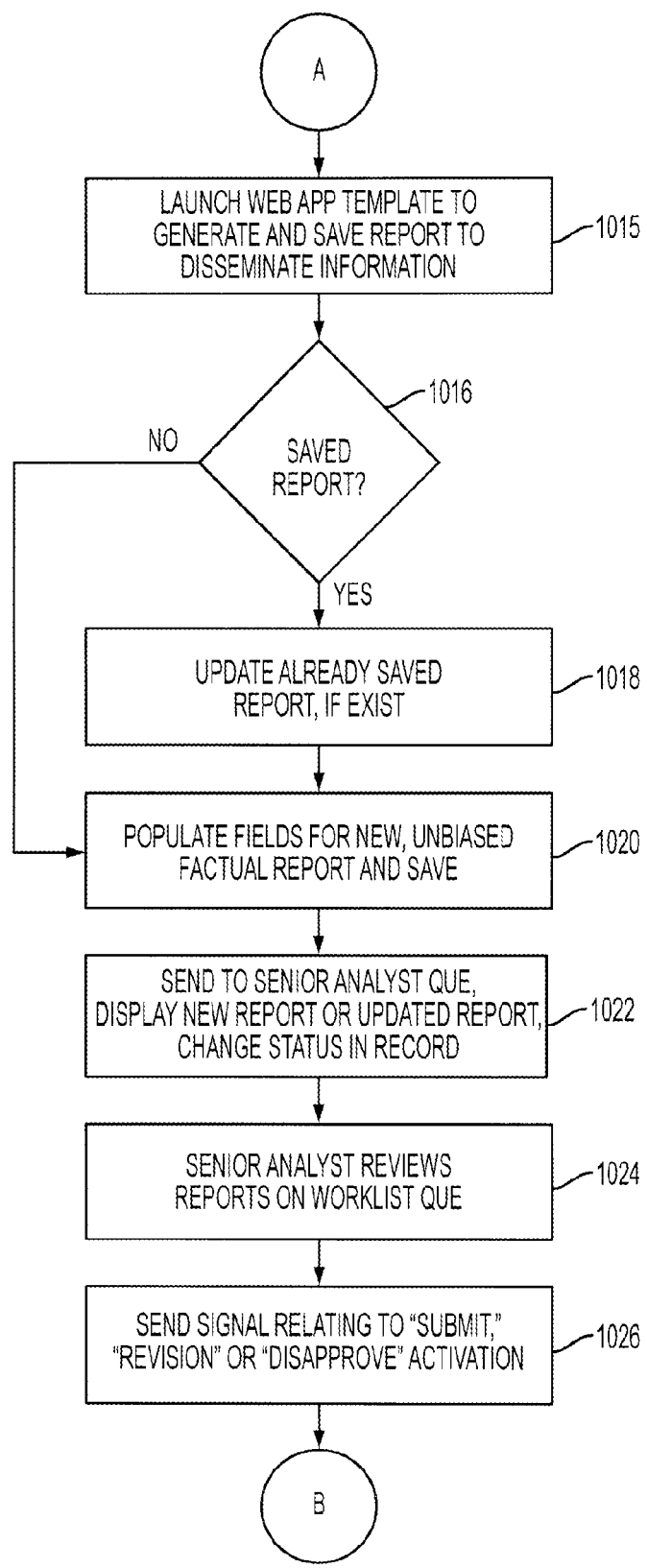
Figure 10C:
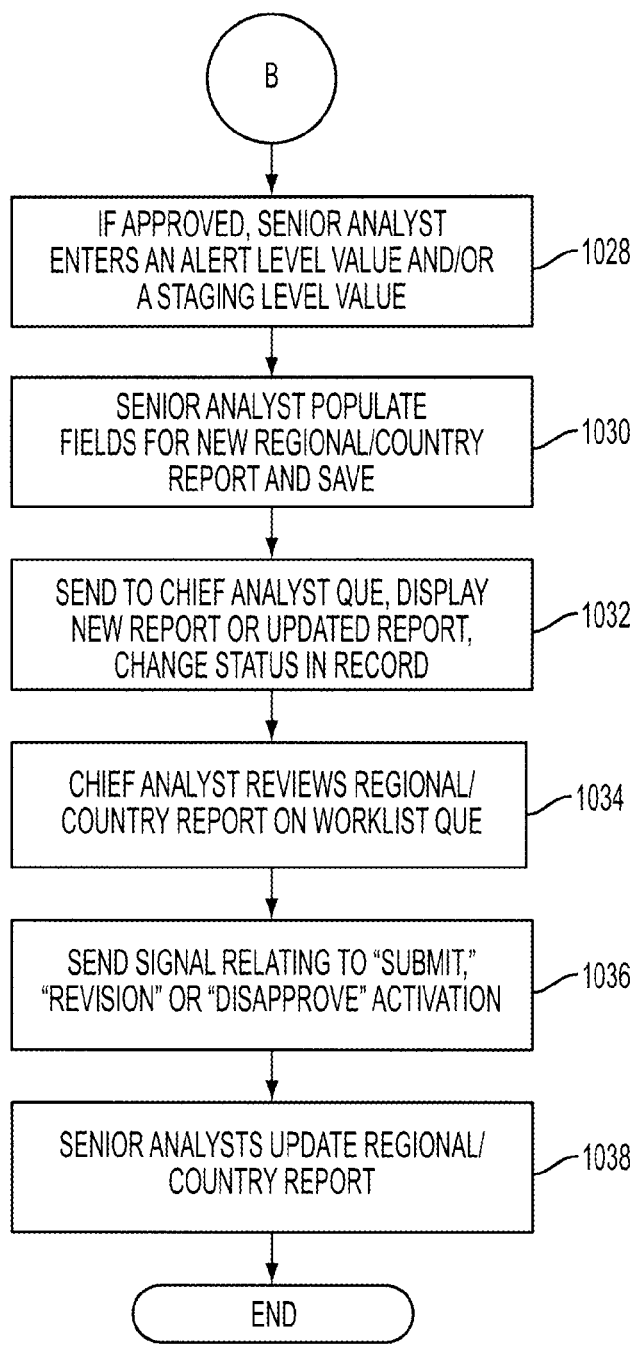
Figure 11:
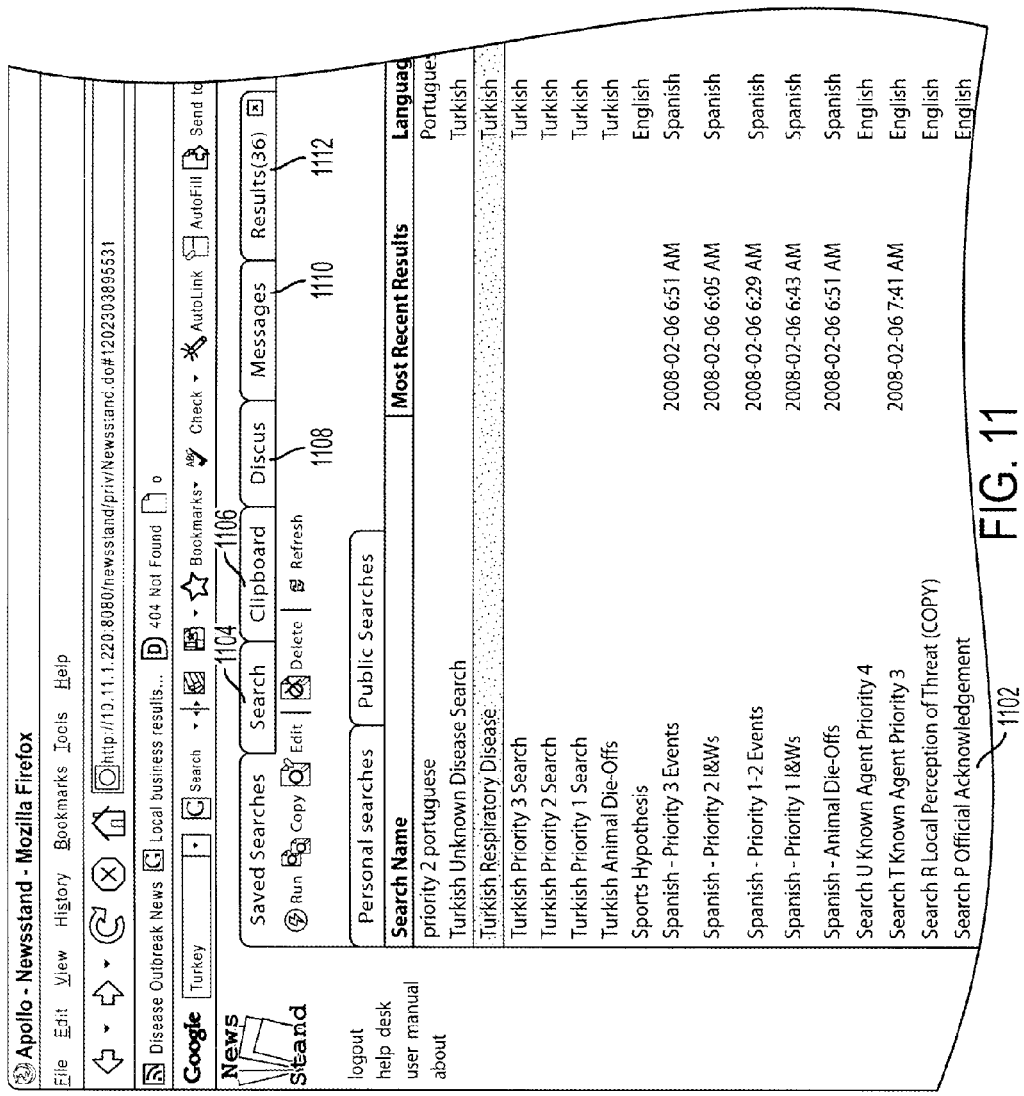
FIG. 11 is a diagram of one feature of the user interface of the present invention.

FIGS. 10A through 10C are an information and workflow diagram that illustrates the steps in the process after those described in FIG. 8. The series of steps begin with the "Newsstand" document search and reporting interface module 308 running. The module 308 includes a search user interface 408 and a search results user interface 410. The search user interface 408 is shown in FIG. 11, and includes a "Saved Searches" tab 1102, a "Search" tab 1104, a "Clipboard" tab 1106, a "Discus" tab 1108, a "Messages" tab 1110, and a "Results" tab 1112. The "Saved Searches" tab 1102 displays all the searches that the analyst 318 has run.

The search user interface 408 allows analysts 318 to form ad hoc search queries separate and apart from the automated searches and models described above and shown in FIG. 8. Queries allow an analyst 318 to search stored documents for keywords and more complex search terms, e.g., concatenations of keywords. An analyst 318 can specify which language to search as well as date ranges for the search and geographical areas for the sources of the document. An analyst 318 can also specify certain document sources to search or one or more countries on which to target the search. In addition, the "Search" tab 1104 allows an analyst 318 to specify the number of results to return, and it provides a graph of documents (typically news articles) over time as well as a comma-separated-value spreadsheet (not shown). An analyst 318 can also save a search to be run at other times, as described previously. Search term translation is provided for certain languages.

The entire system 200 depends upon (1) the validity of the taxonomy and (2) the ability of individual analysts 318 to continuously examine a very large body of media-produced web documents from the information sources 104 to accurately identify events of interest. Because an inherent limit exists on the number of documents in the article repository database 310 that a human can process accurately in a given period of time, the detection of events is limited by the number of analysts 318 working on a particular region. Although analysts 318 may accurately, precisely and consistently identify events, the events so identified will probably contain events that are mundane (i.e., "normal") and not of immediate interest. In addition, analysts may miss some "abnormal" events of high immediate interest in the "Clipboard" tab The "Clipboard" tab 1106 allows an analyst 318 to save particular documents from a search across research sessions.

Step 1002. The "Results" tab 1112 allows an analyst 318 to retrieve documents corresponding to an item in a results list from the article/document repository database 310. An analyst 318 may access the document source information by language, country, area, region, and alphabetical order. The URL of the information source 104, captured frequency information, and other information are provided. FIG. 12 shows a portion of the "Results" tab 1112 for a particular search involving the query 1202. The search results are displayed with links to documents along with date, source name, and source country.

Figure 13:
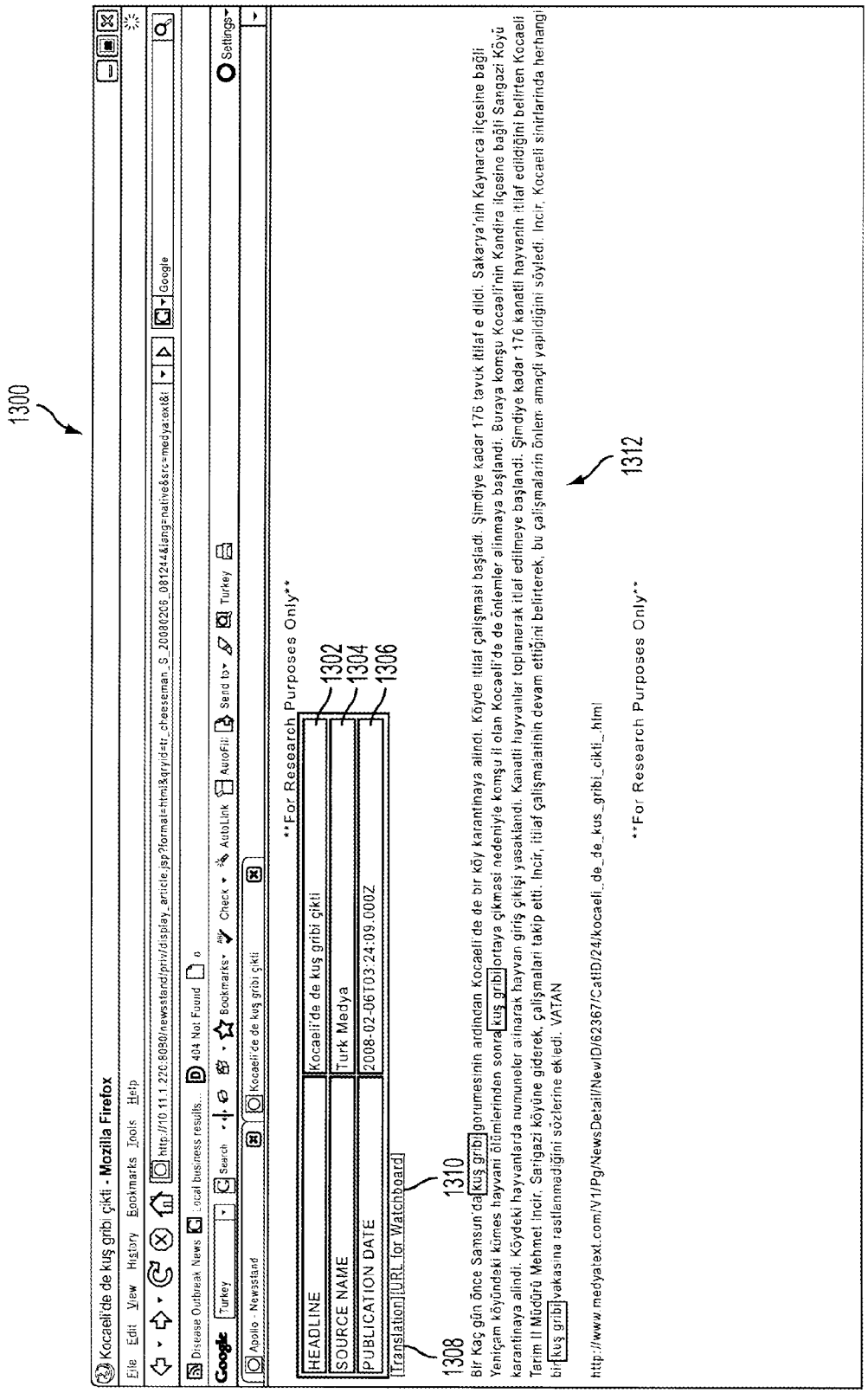
FIG. 13 is a diagram of one stored document in the article repository database according to the present invention.

Clicking on a document link retrieves the document from the article repository database 310 and displays it in another window 1300 as shown in FIG. 13. The displayed information will include the title ("Headline") 1302, source name 1304, publication date 1306, a translation link 1308, a URL link 1310, and the main body 1312 of the web document. Clicking on a header will sort the data using that column's data entries as the sort key.

Step 1004. The translation link 1308 is available for each stored web document if translation into English is available for the language of the document.

Step 1006. If translation is needed and available, it may be demanded by an analyst 318 (translations may also be done automatically). This translation is a front-end access to the machine translation gateway (MTG) subsystem, which is part of the "Newsstand" document search and reporting interface module 308. The MTG is designed as a gateway, offering a standardized interface for users and applications that masks the complexities of one or more off-the-shelf machine translation engines well known in the art. An analyst 318 makes use of translation services using a standard protocol, and is not required to know the specific configurations of various supporting translation technologies. The requesting application submits information to be translated to the MTG subsystem, which then forwards the request to a Translation Control and Scheduling component (not shown) of the MTG subsystem. This component is responsible for determining which of the translation resources is most appropriate for the request, and also for maintaining the schedule and status of the various translation engines. Once the appropriate engine has been selected, a request is sent to the engine for translation service. When the translation is complete, the Translation Control and Scheduling component prepares the response message and forwards it to the MTG interface. The interface prepares and sends the response to the calling application.

Figure 14:
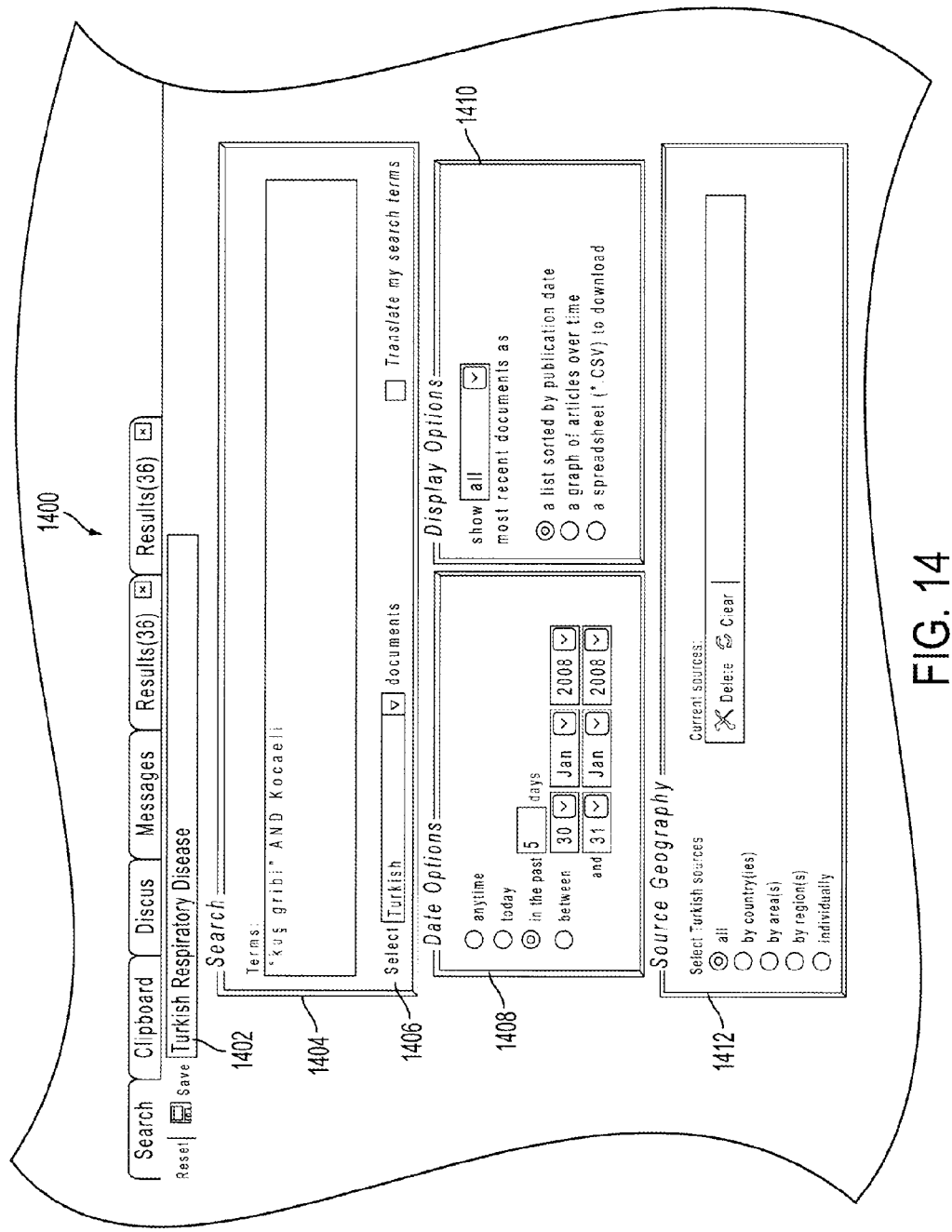
FIG. 14 is a diagram of yet another feature of the user interface of the present invention.

Step 1008. Based on the results shown in the "Results" tab 1112, an analyst 318 may want to create and save additional searches to better clarify existing event-related information. FIG. 14 shows a template 1400 under the "Search" tab 1102 that allows an analyst 318 to enter the parameters for the new search. The template 1400 includes fields for entering a search description/title 1402, search query terms 1404, documents to be searched 1406, date limiters 1408, display options 1410, and source geography limiters 1412. Analysts 318 scan hundreds, possibly thousands, of web document article titles and text daily. Analysts 318 may search by region, country, or specific information source 104. Display options 1410 display a list of titles, or as a graph of hit counts over time. Search query terms 1404 may follow normal Boolean syntax.

The analysts 318 consider whether the information and data from an information source 104 accurately reflect the original website article, whether the event was expected, whether the event is important, and what is the tone/quality of the information and data. Analysis is done with the following premises in mind: 1) any major emerging biological event will disrupt everyday social life of individuals, communities, and institutions in affected areas, and 2) types of description linked to outbreaks of disease are similar across countries/cultures.

Step 1010. Based on event information, and the reporting requirements previously identified for a particular mission, an analyst 318 viewing the search results will determine the priority of reporting. Typically, this will involve identifying whether event reporting will be designated under one of the "Advisory," "Warning," and "Watch" prioritization categories (or they may be the colors yellow, orange, or red, or some other color, pattern, or indicia). An Alert value may be assigned to the country level (although other geographical or political levels may also be used).

An example of the types of events and their respective alert levels are shown in the table below.

TABLE 8

| | Events | Alert Category | | |
|---|---|---|---|---|
| | | WARNING | WATCH | ADVISORY |
| | Indications and Warnings of Biological Events Involving Humans OR Animals | | | |
| 1 | Any indication of intentional use of any biological agent or a biowarfare attack | X | | |
| 2 | Any indication of public health system failure or social collapse associated with a biological event involving humans or animals (i.e., Stage 4 conditions) | X | | |
| 3 | A Stage 3 biological event prompted by illness and associated absenteeism among response staff [except nosocomial infections] | X | | |
| 4 | Public panic documented by local media in context with an active biological event (includes mass evacuations and conflict with officials) | X | | |
| 5 | Social disruption occurring out of expected context for reported pathogen | X | | |
| 6 | Laboratory accident involving exposure of personnel to an unidentified infectious agent with community exposures | X | | |
| 7 | Unique naming of a pathogen | X | | |
| 8 | Any depletion of ventilator supply or compromised ICU support due to demand | | X | |
| 9 | Laboratory accident involving exposure of personnel to an unidentified infectious agent | | X | |
| 10 | Vaccine accident triggering a biological event (i.e. a person falls ill with measles after receiving the measles vaccine) | | X | |
| 11 | Any indication of activation of local emergency response plans related to an unidentified biological or health related event | | X | |
| 12 | First-time reports of a pathogen in a given region/country or in a given species | | | X |
| 13 | Any increased demand for ventilator or ICU support | | | X |
| 14 | Vaccine or therapeutic failure or compromise | | | X |
| 15 | Any incident of unexplained illness requiring additional response or assistance, especially of healthcare, veterinary, or laboratory workers (i.e., Stage 3 conditions) Does NOT have to be a cluster of >3 | | | X |
| 16 | Perceived changes in epidemiology (symptoms, severity, CFR, rates, urban/rural, pop'n affected - ethnicity AND age) | | | X |
| 17 | Any acute cluster (3+) of unexplained illness or deaths in humans or animals | | | X |
| 18 | Anxiety or concern expressed about an active biological event in local media, especially by healthcare or veterinary professionals | | | X |
| 19 | Publicly expressed diagnostic confusion where healthcare professionals and veterinarians are openly debating biological event etiology | | | X |
| 20 | Complex, multi-pathogen event (often associated with environmental perturbation, such as RVF/cholera in East Africa triggered by El Nino). Must contain potential for misdiagnosis. The diseases should therefore be related and not seasonal. | | | X |
| | Known Agents include unusual/risk-promoting practices when morbidity is present | | | |
| 21 | Smallpox (Variola major) | X | | |
| 22 | FMD reported in country from which US imports susceptible animals or animal products | X | | |
| 23 | Newcastle disease reported in country from which US imports susceptible animals | X | | |
| 24 | SARS | X | | |
| 25 | Rift Valley fever virus | | X | |
| 26 | Venezuelan equine encephalitis | | X | |
| 27 | Monkeypox or any other pox virus infection in humans | | | X |
| 29 | Polio | | | X |

TABLE 8-continued

| | | Alert Category | | |
|---|---|---|---|---|
| | Events | WARNING | WATCH | ADVISORY |
| 30 | Plague (Yersinia pestis) | | | X |
| 31 | Filoviruses [e.g., Ebola, Marburg] | | | X |
| 32 | XDR-TB | | | X |
| | Respiratory Disease include unusual/risk-promoting practices when morbidity is present | | | |
| 33 | Healthcare workers ill | X | | |
| 34 | Healthcare worker absenteeism | X | | |
| 35 | Healthcare workers panicking | X | | |
| 36 | Work absenteeism affecting industrial production or normal societal function | X | | |
| 37 | Influenza vaccine not providing protection | X | | |
| 38 | Stage 4 conditions/Public panic | X | | |
| 39 | Major increase in cases over previous years | | X | |
| 40 | Etiological agent or subtype described as unknown | | X | |
| 41 | Stage 3 conditions | | | X |
| 42 | Healthcare worker vacations cancelled or postponed | | | X |
| 43 | Doctors or health workers expressing concern | | | X |
| | High Pathogenic Avian Influenza (H5, H7) include unusual/risk-promoting practices when morbidity is present | | | |
| 44 | Suspected or confirmed H5N1 exhibiting human-to-human transmission | X | | |
| 45 | Suspected or confirmed H5N1 exhibiting transmission to new animal species | X | | |
| 46 | Suspected or confirmed H5N1 human case | | X | |
| 47 | Suspected or confirmed H5N1 mammalian case | | X | |
| 48 | Suspected or confirmed H5N1 avian case | | | X |

Other information sources 104 are available to the analysts 318, such as Google® Alerts, which allow a user to request alerts that can be sent to a user's email address. This application is available for many countries and languages, and may be set up for frequent alerting ("as-published" or "daily"). Still other open source information sources 104 are also available and are checked frequently in a manual fashion because they are not set up in a way that allows the system to automatically download information and data. These information sources include the Ministries of Health and Agriculture, Flu Trackers, ProMED, OIE, Crop Protection Compendium, FAOSTAT, The Cereal Knowledge bank, and others.

Step 1012. Next, an analyst 318 will compare the event information to the biological taxonomy for the particular mission to determine the stage of the event using a heuristic scale or staging model. The present heuristic scale describes the state of biological events according to a heuristic model as described below. The basic framework for the system 200 is that it follows a biological event as it evolves from unifocal, to multifocal, to uncontained, and finally to a state that induces social collapse. On the whole, the model's first two stages (1 and 2) are reminiscent of public health definitions of biological events, whereas the final two stages (3 and 4) are based on sociological definitions. The following descriptions focus first on I&W stages for biological events that affect humans, and then present caveats for biological events that affect animals and plants. Obviously, I&Ws for the former diseases impact medical services and those for the latter diseases affect veterinary services. For zoonotic pathogens (those that affect both animals and humans), I&Ws exist that affect both types of service.

Stage 0 (Environmental Risk Conditions Present or Potential Antecedent to a Biological Event). Stage 0, indicative of a potential increased risk for disease, is a pre-event condition that applies to specific mosquito-vectored and waterborne diseases in certain areas of the world, such as RVF in Kenya, VEE in Venezuela, and diarrheal illness in India and Bangladesh. It has been found that in most of these cases, local public and government officials appeared to respond to a history of disease following both expected and unexpected large-scale seasonal floods. This response included public awareness campaigns, active disease surveillance, and mosquito spraying.

One important feature of the Stage 0 condition is the impact of excessive flooding on medical infrastructure and the ability of the indigenous community to respond to the subsequent emergence of disease. This impact was observed during the 1995 epidemic of VEE in Venezuela, and the 1997-1998 epidemic of RVF in East Africa. It has been observed that if the local infrastructure was already compromised prior to the appearance of a rapidly transmissible disease, the associated social disruption might proceed at a much faster pace.

It has been proposed that Stage 0 is relevant for Kenya, Venezuela, India, and Bangladesh. Stage 0 is likely to be relevant for other areas of the world as well; however, analyses to date have been limited to case studies.

Stage 1 (Unifocal Biological Event). This stage represents the beginning of an identified biological event, when human cases of a disease have presented to a single medical facility and the event has therefore appeared as a unifocal phenomenon. This condition is analogous to the epidemiological term "outbreak," which denotes the unusual appearance of a disease, above baseline but limited in scope. The present model simplifies this definition to mean the appearance of cases at a single medical facility, and thus reflects the uncertainty of dealing with media sources rather than information vetted by the public health community.

Direct I&Ws include reports of human disease that describe clinical impression and epidemiological features of the event. Indirect I&Ws, which are not substantial in Stage 1, fall into two categories: official acknowledgment and official action. Official action is limited and typically includes official investigation and low-level countermeasures, such as vector control campaigns (like mosquito spraying).

For biological events that affect animals, the basic description is the same except that explicit reporting originates in official and unofficial communities linked to veterinary medicine, agriculture, industry, field biology, and forestry, as expressed to local media. Locations where such events occur include veterinary, research, agricultural, and industrial facilities; park lands; and local communities. The staging of such events is similar to that for human disease, with the event being reported to occur at one such facility. A key difference, however, is the implementation of countermeasures. An official order to quarantine the involved animal or animal herd may be reported. If a pathogen with serious economic repercussions, such as foot and mouth disease in cattle or H5N1 avian influenza, is suspected to be present, mass culling of animals may be mandated for both the involved facility and surrounding areas. For the current situation with A/H5N1, this stage may include military support for mass culling of animals in developing nations.

In summary, Stage 1 represents a unifocal biological event with limited countermeasures, minimal demand for medical services, and minimal local perception of threat. As an example, on Oct. 18, 2005, Bashkirstotan village in Russia reported a human case of anthrax. A 67-year-old female resident of Kovarda village in the Gafur region was hospitalized with the cutaneous form of the disease. This report is a single case and thus represents a Stage 1 event.

Stage 2 (Multifocal Biological Event). In Stage 2, disease is present in multiple facilities, and is analogous to the public health definition of an "epidemic." Stage 2 therefore describes a phenomenon that is multifocal but contained (as perceived by the indigenous society). Early I&Ws in this stage include reports of increased demand for pharmaceuticals and medical supplies.

As the biological event progresses, direct I&Ws may include more epidemiological details. However, it is at this point that concern is expressed publicly about whether the initial clinical impression was correct. This step takes place if the pathogen in question is a well-known one that is now displaying new transmission characteristics, or if the initial clinical impression was wrong, and a newly emergent pathogen is present.

Indirect I&Ws include elevated official acknowledgment, with national in addition to local officials making statements regarding the event. Official action progresses to include activation of biosurveillance or screening of individuals and attempts to isolate those infected. Under the category of official action, official investigation progresses to involve national and occasionally international organizations. Countermeasures expand to include disinfection campaigns, vaccine deployment, and official treatment recommendations, reflecting a reactionary posture by the indigenous government to exert control over the situation. Increased demand for medical care, pharmaceuticals, and supplies also appears. Stage 2 sees the first documentation of local perception of threat, with the public reported as being "anxious" or "concerned" about the disease.

When animal populations are involved, a "multifocal" event occurs in more than one of the locations described for Stage 1, above. A key epidemiological feature for Stage 2 events involving animals is documentation of which animal species are involved. This information is important for determining the possible identity of the pathogen. If the event involves a suspected pathogen of economic consequence, more aggressive and widespread animal culling is observed, frequently with military support. Additionally, domestic and international trade restrictions may be implemented by both the host nation and other countries. An official order to quarantine an entire affected facility may be issued. Active screening of animals and animal products at farms, festivals, markets, businesses, and ports of entry is also seen. Disinfection of individuals, equipment, and transportation vehicles is observed, along with roadblocks and checkpoints.

As an example of a Stage 2 event, a biological event of H5N1 avian influenza in poultry was confirmed at three farms in Huainan, a city in Anhui province, People's Republic of China, according to China Central Television (CCTV). The biological event was first reported on November 6, when 800 domestic poultry died. Approximately 126,000 poultry within 3 kilometers (2 miles) of the affected area were slaughtered as a precaution, CCTV reported. Five days later, China confirmed 21 avian influenza biological events in nine provinces, autonomous regions, and municipalities, as reported by Yin Chengjie, Vice Minister of Agriculture, in a news conference in Beijing. Yin said that the avian influenza biological events had killed 144,624 poultry, while a further 21,184,200 had been culled. He also warned that the H5N1 situation in the country was "severe." This series of reports depicts a multifocal biological event with heightened government countermeasures, characteristic of a Stage 2 event.

Stage 3 (Uncontained Multifocal Biological Event or Infrastructure Strain). Stage 3 denotes an uncontained multifocal event that affects the medical infrastructure to the point of strain. Key I&Ws include declaration of the inability to contain or control the disease in question, depletion of vaccine and drug stockpiles and medical supplies, and concerns about whether medical facilities can continue to handle patients. If the disease entity continues unabated, social collapse is imminent.

Direct I&Ws escalate to include health care workers becoming infected, which may occur with such pathogens as influenza or SARS. This marker is an ominous sign, as it indicates a serious potential threat to the continued functioning of medical facilities.

Further diversification of indirect I&Ws is noted in Stage 3. Official acknowledgment includes declaration of a health emergency and requests for international assistance. Official action is increasingly aggressive, with international organizations featuring more prominently in official investigations. Such action includes preemptive infrastructure closures (of schools, festivals, and public transit, among others), official orders to quarantine, initiation of propaganda campaigns, and border and port-of-entry closings; information suppression and prosecution of citizens and organizations appear as well.

Also in Stage 3, demand for medical services diversifies. There is increased demand for specialized, innovative, or alternative medical care. Demand for pharmaceuticals and medical supplies progresses to the point of stockpile depletion and subsequent mobilization of resources from neighboring regions. Local perception of threat evolves and leads to new behaviors, such as hoarding and self-preservation (like panic buying of staples); avoidance of sites of public congregation; and expressions of dissent toward officials whom the public now deems incompetent in their handling of the event. Changes in business practice reflect market responses to a severe shift in the supply-and-demand ratio, as local medical resources become depleted. Price gouging and formation of black markets are seen. Integrity of infrastructure is observed to be compromised, with medical facilities reporting "strain" or seeing patients at "full capacity," implying few reserves left to treat the public. Multiple schools and businesses close on account of widespread illness—not because of an official mandate to control its spread, but rather because the disease is directly affecting these institutions. These parameters are signs of severely compromised social functioning.

In Stage 3 events involving animals and/or the military's participation in countermeasures is more widespread and common. Preemptive infrastructure closures include individual businesses, farms, festivals, and the stock market. Local perception of threat is manifested in panic selling of farm animals at risk of exposure to the disease, panic buying of animal products in anticipation of a market restriction, and avoidance of public places. Public dissent may be observed as both the disease itself and official countermeasures, such as animal culling, begin to have a severe effect on the livelihood of the agricultural community. A compromise in the integrity of infrastructure is noted with the closure of individual businesses, farms, and festivals; these closures are not preemptive, but rather stem directly from the pathogen itself, from attendant countermeasures, and from social anxiety. Severe economic damage for the host nation is imminent.

As an example of a Stage 3 event, multiple reports in Indonesia reflected a strained veterinary infrastructure that can no longer respond effectively to an avian influenza crisis starting in January 2004. For example, "A senior official at the Jakarta Animal Husbandry, Fisheries, and Maritime Affairs Agency, Adnan Ahmad, said it was impossible to respond immediately to every report because local animal husbandry agencies had only three to four veterinarians to cover the entire regency. He did acknowledge, however, that several officials at local animal husbandry agencies in Greater Jakarta had failed to make avian influenza their top priority since the national campaign to eradicate the disease was launched by President Susilo Bambang Yudhoyono in September." Additional reporting revealed the magnitude of the animal epidemic: "Mathur Riyadi, Director General of Veterinary services stated that the avian influenza biological event has affected 21 out of 30 provinces in Indonesia with the number of chickens killed by the virus totaling 9.53 million. Avian influenza has been found in at least 132 regencies and cities across Indonesia. Additional investigation also indicated preliminary attack of avian influenza in four other provinces, namely South Sulawesi, Jambi, East Kalimantan and North Sumatra, he said on the sidelines of a hearing with legislators at the parliament compound." This is a multifocal biological event with strained veterinary infrastructure, and is indicative of a Stage 3 event.

Stage 4 (Maximally Disruptive Biological Event or Infrastructure Collapse). Stage 4 is the regional- or national-level end point for a socially disruptive biological event, when social collapse results from the disease's sustained defiance of countermeasures and maximal social disruption occurs. Key I&Ws of a Stage 4 event include conflict due to public outcry over the handling of the event, mass evacuations, and refusal of the medical infrastructure to see patients.

Stage 4 is defined principally by indirect I&Ws. Official action is maximally aggressive, with preemptive infrastructure closures occurring systematically across multiple sectors (such as schools, festivals, and public transit). Systematic closures and redirection involving the entire local medical infrastructure are noted, with medical facilities becoming wholly devoted to treating those with the disease. Mass quarantines of thousands of people may be seen. Information suppression and prosecution of citizens and organizations escalate to arrests and threats of capital punishment if control measures such as quarantine are violated. Medical facilities may also be punished for refusing to see patients.

Demand for medical care results in a total depletion of pharmaceuticals and medical supplies; military transport of materiel on a national level, with mobilization of internationally acquired supplies, may be observed. Absenteeism is observed among health care workers and first responders due to disease, fear, or both. Consequently, dependence upon military medical support reaches maximum levels.

Local perception of threat appears as an abject lack of public confidence in the government's ability to handle the situation. This lack of confidence takes such forms as open defiance of official mandates, like quarantine or curfew; rioting; and open conflict between civilians and law enforcement or military personnel. Psychological impact may be observed, with signs of mass depression, anxiety, and apocalyptic and suicidal ideation. Counseling hotlines and support services may be inundated with requests for assistance. People thought to have the disease may be ostracized. Patients may avoid medical facilities for fear of receiving inadequate care, being placed in isolation or quarantine, or becoming infected by the pathogen. Conversely, medical facilities may be at the point of requiring systematic security, both to hold back the panicked public and to prevent health care workers from leaving.

Business practices evolve to the limit of tolerable price gouging. Emergency price controls on pharmaceuticals and basic staples may be broadly implemented.

Integrity of infrastructure reaches the point of collapse at the societal level, with martial law having become the mechanism for maintaining order. Important social functions, such as weddings, are canceled. Incoming and outgoing international air traffic is terminated, as are diplomatic visits by representatives of other countries, and nonessential foreign diplomatic personnel evacuate. Indeed, it is at this level that ostracisms of the affected country by the rest of the international community may be observed.

During Stage 4 biological events involving animals, extreme measures may be taken to assist with animal culling, such as having prisoners perform this task. An entire city or region may be officially ordered into quarantine, with military or police enforcement. Prosecution of citizens or businesses for unauthorized dissemination of information, profiteering, or disregarding a quarantine may be observed. Maximal local perception of threat is reflected in public demonstrations, rioting, and refusal to comply with official orders. Broad, sector-wide, systematic collapse of infrastructure occurs, including industry-wide closures, widespread economic collapse with gross stock market changes, loss of access to basic staples, declaration of martial law, declaration of a complete social crisis, and total dependence on international support.

Because a disease that is focused primarily in animals generates less social anxiety than one that is actively incapacitating and killing humans, a Stage 4 biological event involving animals tends to generate less social disruption than one involving humans. For example, mass evacuation and panic are typically not seen in a Stage 4 event that involves animals.

In summary, a Stage 4 biological event entails maximal regional- or national-level social disruption and a complete loss of containment. An example of a Stage 4 event is the SARS outbreak in Guangdong, People's Republic of China, 2003. In April 2003, official acknowledgment no longer involved denying the presence of SARS in Guangdong; rather, its presence in areas previously rumored to be infected was confirmed. Official action involved maximal enforcement of countermeasures and criminal prosecution for hoarding, speculation, and illegal manufacturing of medical supplies, antiviral medications, and general staples. In addition, official action sought to provide sustained medical relief for SARS patients. The government prosecuted health care workers and medical facilities for refusing to treat SARS patients and prevented medical staff from leaving hospitals by posting guards at hospital entrances and exits. In some cases, the police arrested runaway SARS patients and mandated home confinement of all people who came in contact with patients confirmed to have the disease. Demand for medical services was indicated by reports of army medics mobilizing to fight SARS in Beijing, and of airlifts bringing medical supplies to stockpile-depleted areas. These reports also focused on heightened local perception of threat, noting multifocal rioting and voluntary evacuation, worker protests, discrimination against workers with SARS, various efforts at self-preservation, and innovative behaviors. Finally, reports of hospital closures in SARS-affected areas and temporary closures and work suspensions at national financial and historical institutions suggested infrastructure collapse. Additionally, temporary suspension of marriage licenses in Beijing demonstrated that SARS was gradually eroding the very fabric of social life in China.

Stage P (Preparatory Posture). Countries often assume a preparatory posture in anticipation of a biological event. Sometimes, this posture implied the presence of an event when there was none; other times, this posture anticipated the presence of an event that was confirmed once active surveillance measures were implemented. It was found that, particularly in closed societies, a declared preparatory posture for a biological event was a possible mechanism for disinformation, to explain the abrupt appearance of countermeasures and social disruption related to the actual presence of a disease. Therefore, Stage P is proposed to represent a preparatory posture that reflects anticipation of a biological event. Stage P indications and warnings fall solely in the indirect category because presumably no biological event is actually present yet. However, if an actual event occurs during the course of preparation and is later reported by the host nation, Stage P may be changed to Stage 1 or 2.

Indirect I&Ws during Stage P include official acknowledgment, official action, demand for medical services, and local perception of threat. Official acknowledgment typically takes the form of an explicit official announcement that preparatory measures are required because of concern about an imminent biological threat. Official action includes official investigation, implementation of countermeasures, and activation of biosurveillance or screening. Prophylactic countermeasures include vector control measures; hygiene campaigns; activation of pharmaceutical programs, such as vaccine delivery; preemptive infrastructure closures; quarantine of inbound international flights and ships from affected areas; public awareness campaigns; and closings of borders and ports of entry. Demand for medical services reflects anticipation versus actual demand, and includes restructuring of the medical infrastructure to accommodate a potential influx of patients requiring specialized care, as well as mobilization of pharmaceuticals and supplies. Local perception of threat is indicated by public concern or anxiety, with dissent occasionally being reflected in media articles that criticize the lack of an appropriate state of preparedness.

With regard to animal disease, prophylactic countermeasures include animal culling in locations where a pathogen may be introduced from a neighboring country. Commerce and trade restrictions may be implemented to prevent pathogen introduction. Preemptive infrastructure closures may include farms. Quarantine may be implemented for a farm or facility, for freight transport, or for inbound international air flights or ships, to enable screening. Demand for veterinary services is observed as an anticipatory condition similar to the preparatory posture for human disease. Local perception of threat regarding animal disease appears as changes in consumer behavior, specifically avoidance of the purchase of animal products.

An example of a Stage P event is avian influenza in the Democratic People's Republic of Korea (DPRK), April-November 2005. In early April, a report surfaced that South Korean officials had intensified preventive measures against avian influenza in the Demilitarized Zone (DMZ) on the border with North Korea. The same report also noted that South Korean officials were stepping up their monitoring of avian influenza at a tourism site in North Korea's scenic Mount Geumgang resort, which attracts South Korean tourists. In September 2005, the official DPRK news agency reported that, despite the State Emergency Veterinary and Anti-epizootic Committee's assurance on July 5 that avian influenza had been eradicated, the government continued to implement avian influenza prevention efforts, such as surveillance of migrant movements, a reporting network, and the development of a vaccine. Finally, in mid-November 2005, a report surfaced that quarantine efforts on the border and in other terminals of the DPRK had been intensified to prevent avian influenza. The report noted that people and goods coming from or via H5N1-affected regions and countries were subject to special measures: those with symptoms of disease were being quarantined, and imports of poultry goods from those areas were strictly banned. These reports indicate that preparatory measures were being taken in response to avian influenza. Since there were no reports of actual disease, the event can be designated as Stage P.

Stage R (Recovery). This event stage is used to characterize societal actions related to recovery from an event.

Table 3A below summarizes the heuristic staging model scale that is described in detail above (Table 3B summarizes the heuristic staging model scale related to plant disease events, and Table 3C summarizes the heuristic staging model scale related to animal disease events).

TABLE 3A

| Stage | Condition |
|---|---|
| P | Preparatory posture |
| 0 or A | "Potential Antecedent to a Biological Event" Environmental conditions favorable to support the appearance of a biological event (for specific diseases and locations only-see text) |
| 1 | Unifocal biological event |
| 2 | Multifocal biological event |
| 3 | "Infrastructure Strain" Severe infrastructure strain, depletion of local response capacity |
| 4 | "Infrastructure Collapse" Social collapse at the regional or national level |
| R | Recovery |

TABLE 3B

| Stage | Condition |
|---|---|
| A | Potential Antecedent to Plant Event<br>Crop or forest loss NOT Reported, even if pest is present;<br>Ex: public awareness campaigns, import bans, measures to prevent pest entry or outbreaks, pest interceptions at the border, crop loss not reported but anticipated due to drought, forecasts of reduced crop production |
| 1 | Unifocal plant event<br>Crop or forest loss reported in a single village<br>Ex: pest outbreak destroys crops on several farms in a single village, drought affecting crops in a single village. |
| 2 | Multifocal plant event<br>Crop or forest loss reported in multiple villages, or a political division that can reasonably be expected to contain multiple villages.<br>Ex: pest outbreak update, official response to multifocal outbreaks, a plant disease affects a third of the crops in a valley known to contain numerous villages, a drought affecting multiple villages and crop loss due to drought is reported. |
| 3 | Uncontained plant event<br>Crop loss reported and there are indications of social strain due to the crop loss<br>Ex: food shortage, food aid requested, or food aid sent because a pest outbreak, drought, or flood has destroyed crops |
| 4 | Maximally Disruptive Plant Event<br>Crop loss reported, leading to social disorder<br>Ex: industry-wide business closure, financial collapse, mass migration, food riots, looting of grain stores, collapse of government |
| R | Recovery<br>Past Crop loss may be reported, along with report of recovery from effects of previous crop loss<br>Ex: official statement of recovery, reports about crop disease events after they have occurred and their impact has ended, report of people returning to farm land after a massive outbreak has ended and the food supply has been restored |

Note,
Stage A replaces and merges Stage 0 and Stage P.

TABLE 3C

| Disease/Pest/Condition | Pathogen | Host [Species] | Detail | Disease Priority |
|---|---|---|---|---|
| African horse sickness | Virus | Equine | Self-explanatory, Also called: peste équine. perdesiekte, pestis equorum, peste equine Africana | 3 |
| African swine fever | Virus | Swine | Self-explanatory, Notable outbreaks in Georgia, Armenia, Azerbaijan during 2007-2008. Also called: pesti porcine Africaine, maladie de Montgomery, warthog disease | 3 |
| Akabane | Virus | Multiple | Also called: Congenital arthrogryposis-hydranencephaly syndrome, A-H syndrome, congential bovine epizootic A-H syndrome, acorncalves, sillycalves, curly lamb disease, curly calf disease, dummy calf disease | 3 |
| alphaviruses | Virus | Multiple | Chikungunya, Ross River Fever, Venezuelan Equine Encephalitis. Other members of this family include: Sindbis virus, Mayaro virus, and many others | 3 |
| anthrax | Bacteria | Multiple | Also called: woolsorters' disease, Cumberland disease, maladi charbon, malignant pustule, malignant carbuncle, milzbrand, splenic fever | 1 |
| arenaviruses | Virus | Rodent | Arenaviruses include: Lassa, Flexal, Guanarito, Junin, Machupo, and Sabia | 2 |
| Argentine hemorrhagic fever (Junin) | Virus | Rodent | Arenavirus. Vector is drylands vesper mouse. Found in Argentina. | 2 |
| astrovirus | Virus | Multiple | Infects mammals and birds. Cause of gastroenteritis. | 4 |
| avian influenza | Virus (subtypes H5 and H7) | Avian | Use for both highly pathogenic avian influenza (HPAI) and low pathogenic avian influenza (LPAI). Also called: fowl plague, grippe aviaire. | 1 |
| bluetongue | Virus | Multiple | Bluetongue is an infectious, noncontagious arthropodborne viral disease primarily of domestic and wild ruminants, almost exclusively sheep. Also called: sore muzzle, psedo foot-and-mouth disease, muzzle disease | 3 |

TABLE 3C-continued

| Disease/Pest/ Condition | Pathogen | Host [Species] | Detail | Disease Priority |
|---|---|---|---|---|
| Bolivian hemorrhagic fever (Machupo) | Virus | Rodent | Arenavirus. Vector is large vesper mouse. Found in Bolivia. | 2 |
| botulism | Bacteria Toxin | Multiple | Seven different types - Type B is found in horses, Type C is most common in animals, Type D is found in cattle and dogs, Type A and E is in mink and birds. | 2 |
| bovine spongiform encephalopathy | Prion | Cattle | Mad cow disease, variant Creutzfeld-Jakob disease (vCJD), scrapie, chronic wasting disease, kuru | 3 |
| Brazilian hemorrhagic fever (Sabia) | Virus | Rodent | Arenavirus. Vector unknown, but most likely infects rodents. Found in Brazil. | 2 |
| brucellosis | Bacteria | Multiple | Also called Bang's disease, Gibraltar fever, Malta fever, Maltese fever, Mediterranean fever, rock fever, or undulant fever | 3 |
| campylobacter | Bacteria | Ruminants | *C. fetus* is a cause of spontaneous abortions in cattle and sheep. Also called: campylobacter enteritis, vibrionic enteritis, vibriosis. | 4 |
| chikungunya | Virus | Primates | Main virus reservoirs are primates. Spread by mosquitoes. | 3 |
| cholera | Bacteria | Aquatic Species | Infected shellfish and zooplankton can spread cholera. | 3 |
| classical swine fever | Virus | Swine | Self-explanatory. Note that this is often referred to as hog cholera, swine fever, or pig plague (in many languages) | 3 |
| *clostridium difficile* or *clostridium perfringens* | Bacteria | Multiple | Can infect horses, dogs, and pigs. Causes diarrhea and intestinal disease. | 4 |
| contagious bovine pleuropneumonia | Bacteria | Cattle | (CBPP) self-explanatory | 3 |
| contagious caprine pleuropneumonia | Bacteria | Sheep and goat | (CCPP) self-explanatory | 3 |
| Crimean-Congo hemorrhagic fever | Virus | Multiple | Self-explanatory. Also called: Congo fever, Central Asian hemorrhagic fever | 2 |
| dengue | Virus | Primates | Dengue reservoir is primates. | 3 |
| *E. Coli* O157:H7 | Bacteria Toxin | Multiple | Major reservoir is cattle. | 4 |
| Eastern equine encephalitis | Virus | Multiple | (EEE) self-explanatory. Also called: sleeping sickness, Eastern equine encephalomyelitis | 3 |
| ebola | Virus | Multiple | Previous reports of ebola in animals such as gorillas, chimpanzees, and duikers (antelope). | 1 |
| encephalitis | Unknown | Multiple | Encephalitis is a symptom (swelling of the brain) and may result from viral or bacterial infections - influenza, RVF, HFMD, and many other organisms can cause encephalitis. Post tick-borne encephalitis under appropriate categories (Central European, Siberian, or Far Eastern) | 4 |
| filariasis | Parasite | Multiple | Infects cattle, horses, and dogs. Also called: verminous haemorrhagic dermatitis (bovine), intradermal onchocercosis of cattle (bovine), stenofilaria assamensis (bovine), summer bleeding (equine), heart filariasis (canine). | 4 |

TABLE 3C-continued

| Disease/Pest/Condition | Pathogen | Host [Species] | Detail | Disease Priority |
|---|---|---|---|---|
| Flexal virus | Virus | Rodent | Arenavirus. Rice rat is vector. Found in Brazil | 2 |
| foot-and-mouth disease | Virus | Multiple | Self-explanatory. | 3 |
| gastroenteritis | Virus | Multiple | Diseases reportable to OIE include: transmissible gastroenteritis and bovine viral diarrhea. | 4 |
| glanders | Bacteria | Equine | Potential BW agent. Naturally occurs primarily in horses, mules, and donkeys. Also called: farcy, malleus, droes | 4 |
| hantavirus | Virus | Rodent | Rodents are the carriers of hantavirus. Also called: hemorrhagic fever with renal syndrome (HFRS), hantavirus pulmonary syndrome (HPS), hemorrhagic nephrosonephritis, epidemic hemorrhagic fever, Korean hemorrhagic fever, nephropathia epidemica (NE) | 3 |
| heartwater | Bacteria | Multiple | A rickettsial disease of ruminants. Also called: cowdriosis | 4 |
| Hendra virus | Virus | Equine | Self-explanatory. Also called: equine morbillivirus pneumonia, acute equine respiratory syndrome | 2 |
| hepatitis | Multiple | Multiple | Viral hepatitis includes: yellow fever, hepatitis E (pigs are carriers). Bacterial hepatitis includes: Q fever, rocky mountain spotted fever. Use hepatitis when specific disease is not mentioned. | 4 |
| infectious salmon anemia | Virus | Fish | Disease of salmon caused by orthomyxovirus | 4 |
| Japanese encephalitis | Virus | Multiple | Self-explanatory. Also called: Japanese B encephalitis, arbovirus B, mosquito-borne encephalitis virus | 3 |
| Lassa fever | Virus | Rodent | Arenavirus. Vector is natal multimammate mouse. Found in West Africa. | 2 |
| legionellosis | Bacteria | Multiple | Horses and cattle have been known to be infected with *L. pneumophila*. | 4 |
| leptospirosis | Bacteria | Multiple | Leptospirosis is a worldwide zoonotic disease of domestic animals and wildlife. Synonyms: Andaman hemorrhagic fever, Canefield fever, Canicola fever, Field fever, Fish handler's disease, Fort Bragg fever, Japanese autumnal fever, Mud fever, Pre-tibial fever, Rice field fever, Swamp fever, Swineherd disease, Weil's disease | 4 |
| malaria | Parasite | Multiple | Natural host is monkeys. Different forms of malaria affect different species and usually do not pass between species. | 4 |
| malignant catarrhal fever (alcelaphine) | Virus | Multiple | Also called: malignant catarrh, malignant head catarrh, gangrenous coryza, catarrhal fever, snotskiekte | 4 |
| Marburg | Virus | Multiple | Infections reported in primates, reservoir suspected to be bats. | 1 |
| melioidosis | Bacteria | Equine | Self-explanatory. Melioidosis is clinically and pathologically similar to glanders disease, but the ecology and epidemiology of melioidosis are different from glanders. Also called: pseudoglanders, Whitmore disease | 4 |

TABLE 3C-continued

| Disease/Pest/ Condition | Pathogen | Host [Species] | Detail | Disease Priority |
|---|---|---|---|---|
| menangle | Virus | Swine | Cases mummified and stillborn piglets, reduced litter size, and abortions. Also called: menangle virus. | 4 |
| meningitis: viral and bacterial | Multiple | Multiple | Inflammation of the meninges - often seen in conjunction with inflammation of the brain (encephalitis). Causes fever, rigidity, and spasms. | 4 |
| Newcastle disease | Virus | Avian | Self-explanatory. Also called: avian paramyxovirus-1 infection, goose paramyxovirus infection | 3 |
| Nipah virus | Virus | Swine | Self-explanatory. Also called: porcine respiratory and encephalitis syndrome, porcine respiratory and neurologic syndrome, barking pig syndrome | 2 |
| norovirus | Virus | Multiple | Strains detected in swine and cattle. Possible transmission through animal products. | 4 |
| other | Unknown | Multiple | Use as follows: the disease/health risk being reported is not associated a single disease (ie: hospital strain) factors that could contribute to social disruption later (hospital strikes, shortages, etc.) | 4 |
| pandemic influenza | Virus | Multiple | Use only when a specific subtype is not specified or when a pandemic strain emerges. Report human-to-animal and animal-to-human transmission or infection of a novel species. | 1 |
| peste des petits ruminants | Virus | Sheep and goat | (PPR) is an acute or subacute viral disease of goats and sheep characterized by fever, necrotic stomatitis, gastroenteritis, and pneumonia. It is also known as pseudorinderpest of small ruminants, pest of small ruminants, pest of sheep and goats, Kata, stomatitis-pneumoenteritis syndrome, contagious pustular stomatitis, and pneumoenteritis complex. Sheep are less susceptible than goats; cattle are only subclinically infected. Humans are not at risk. | 3 |
| Plague | Bacteria | Multiple | Plague can infect rodents and cats, but mostly animals are carriers of the infected flea. | 1 |
| porcine reproductive and respiratory syndrome | Virus | Swine | (PRRS) self-explanatory. | 3 |
| pox disease | Virus | Multiple | Sheep pox, horse pox, rabbit pox, fowl pox, mouse pox, cowpox, lumpy skin disease | 2 |
| psittacosis | Bacteria | Avian | Self-explanatory. Also known as "parrot fever", Chlamydiosis, and Ornithosis. Acutely ill birds may not mount an antibody response, also yielding false-negative results. Nonspecific signs may include ocular, nasal, or conjunctival irritation and discharge; anorexia; dyspnea; depression; dehydration; polyuria; biliverdinuria; and diarrhea. | 3 |
| Q fever | Bacteria | Multiple | Self-explanatory, affects humans. Synonyms: Balkan grippe, Coxiella burnetii, Febbre australiana, Febre Q, Nine Mile fever, Q-Fieber, Q-koorts, Query fever, Red River fever. | 3 |

TABLE 3C-continued

| Disease/Pest/ Condition | Pathogen | Host [Species] | Detail | Disease Priority |
|---|---|---|---|---|
| rabies | Virus | Multiple | Reservoirs: Cattle, Sheep, Goat, Bird, Fish, Rodent, Rabbit, Tick, Bandicoot, Marsupial, Dog, Cat Self-explanatory. Also called: hydrophobia, Lyssa | 4 |
| respiratory disease | Unknown | Multiple | Use for animal influenza outbreaks - equine influenza, canine influenza, etc. | 1 |
| ricin | Poison | Multiple | Insects are poisoned after feeding on plant leaves. Castor beans are used in animal feed, but toxicity may remain even after heat treatment. Horses and ducks are particularly susceptible. | 2 |
| Rickettsial disease | Bacteria | Multiple | includes Q fever. Use when specific agent is not mentioned | 4 |
| *Rickettsia prowazekii* | Bacteria | Other | infections spread by squirrel lice | 4 |
| *Rickettsia rickettsii* | Bacteria | Other | Bacterium causing Rocky Mountain spotted fever | 4 |
| Rift Valley fever | Virus | Multiple | Self-explanatory. Also called: infectious enzootic hepatitis of sheep and cattle | 1 |
| rinderpest | Virus | Multiple | Self-explanatory. Also known as "cattle plague" or "steppe murrain." NOTE: An eradication effort is underway for Rinderpest; it is now extremely limited in spread, so consider this a high priority disease | 3 |
| Ross River virus | Virus | Multiple | (RRV) self-explanatory; Also referred to as epidemic polyarthritis | 4 |
| rotavirus | Virus | Multiple | Can infect livestock. Causes severe diarrhea. | 4 |
| salmonellosis (non-typhoid) | Bacteria | Sheep and goat | Use for all Salmonella infections, except typhoid fever | 4 |
| screwworm | Parasite | Multiple | Larvae of a certain fly species that feed on living tissues of animals | 4 |
| severe acute respiratory syndrome (SARS) | Virus | Multiple | Likely that SARS originated from animals such as civet cat, raccoon dog, and badgers. | 1 |
| shigella (except shigellosis) | Bacteria | Primates | Only causes disease in primates, not other animals. Typically causes dysentery. | 4 |
| spring viremia of carp | Virus | Fish | Contagious viral disease mainly seen in farmed carp. Also called: infectious dropsy of carp, infectious ascites, hydrops, red contagious disease, rubella, hemorrhagic septicemia | 4 |
| streptococcus suis | Bacteria | Swine | This refers ONLY to a porcine disease. | 4 |
| swine vesicular disease | Virus | Swine | Self-explanatory. Also called: porcine enterovirus infection | 3 |
| tetanus | Bacteria | Multiple | Birds are resistant, but horses are most susceptible. Also called: lockjaw | 4 |
| tuberculosis | Bacteria | Multiple | Avian TB is also called PDD syndrome. Paratuberculosis is also called Johne's Disease. Bovine TB is reportable. | 4 |
| tularemia | Bacteria | Multiple | Also called Pahvant Valley plague, rabbit fever, deer fly fever, Ohara's fever | 2 |
| undiagnosed animal disease | Unknown | Multiple | Use when reporting clearly suggests that disease is the cause of symptoms. When the cause of an animal die-off is undetermined and non-disease | 1 |

TABLE 3C-continued

| Disease/Pest/ Condition | Pathogen | Host [Species] | Detail | Disease Priority |
|---|---|---|---|---|
| | | | factors are suggested (feed, trauma, etc), post under Unexplained Animal Deaths | |
| undifferentiated hemorrhagic virus | Virus | Multiple | OIE reportable diseases include: epizootic hemorrhagic disease, rabbit hemorrhagic disease, viral hemorrhagic septicemia. | 1 |
| undifferentiated viral fever | Virus | Multiple | Reports of viral fever in animals without specifications as to the type. | 2 |
| Venezuelan equine encephalitis | Virus | Equine | (VEE) self-explanatory. Also called: Venezuelan equine encephalomyelitis, sleeping sickness | 1 |
| Venezuelan hemorrhagic fever (Guanarito) | Virus | Rodent | Arenavirus. Vector is short-tailed cane mouse. Found in Venezuela. | 2 |
| vesicular stomatitis | Virus | Multiple | Self-explanatory. Also called: sore mouth of cattle and horses, Indiana fever | 3 |
| West Nile virus | Virus | Multiple | Self-explanatory. Synonyms: West Nile fever, Lourdige, Near Eastern equine encephalitis, Ntaya, Usutu | 4 |
| Western equine encephalitis | Virus | Equine | (WEE) self-explanatory. Also called: sleeping sickness, western equine encephalomyelitis | 3 |
| yellow fever | Virus | Multiple | Known to infect primates and small mammals through bite of infected mosquito. | 1 |

Applying the above model, it has been found that several pathogens (e.g., plague, SARS, RVF, and VEE) tended to generate high levels of social disruption in certain countries. In a prospective analyses for May 1-Jul. 15, 2005, influenza-like illness was the most common event detected. It generated widespread social disruption, consistently reaching Stage 3 across multiple countries with medical infrastructures of varying sophistication. It was found that 14 percent of the events involving influenza-like illness progressed from Stage 1 to 2, and 60 percent from Stage 2 to 3. Of a total of 50 biological events detected for the Pacific Rim (involving 12 diseases in 15 countries), 58 percent were detected at Stage 1, 26 percent at Stage 2, 16 percent at Stage 3, and none at Stage 4. The retrospective analyses detected a variety of biological events, several of which had reached an advanced stage (3 or 4), as shown in Table 4 below.

TABLE 4

| Disease | Maximum Stage Level Reached |
|---|---|
| Brucellosis | 1 |
| Avian influenza (human disease) | 2 |
| Japanese encephalitis | 2 |
| Typhoid | 2 |
| Dengue fever | 3 |
| Diarrheal disease | 3 |
| Influenza-like illness | 3 |
| Malaria | 3 |
| Meningococcal meningitis | 3 |
| Polio | 3 |
| "Swine Flu" Influenza A/H1N1 | 3 |
| Plague | 4 |
| SARS | 4 |
| Rift Valley fever | 4 |
| Venezuelan equine encephalitis | 4 |

Certain I&Ws are cause for particular concern. It is believed that they should be among the most important targets for surveillance, given that they may indicate the presence of a biological agent that is novel, is highly transmissible, causes high morbidity or mortality, and/or is defying countermeasures. Consequently, it has been proposed that the following parameters of critical I&Ws require rapid verification:

| Parameter | Implied Stage | Example |
|---|---|---|
| Illness or death among health care or veterinary workers | 1-4 | SARS, influenza, emerging zoonotic disease |
| Military medical or veterinary support | 1-4 | SARS, influenza, emerging zoonotic disease |
| Depletion of stockpiles of pharmaceuticals or medical supplies | 3 | SARS, influenza, VEE, RVF |
| Regional or national mobilization of medical resources | 3 | SARS, influenza, VEE, RVF |
| Mass evacuation and panic | 4 | Plague, Ebola hemorrhagic fever |
| Rioting and martial law | 4 | SARS, pandemic influenza |

The heuristic staging model and numeric scale above is suggested for use when conducting biosurveillance missions; however, other scales may be more useful for biosurveillance and other types of event monitoring. The United States National Weather Service has used various models to describe the disruptive and destructive potential of storm systems. For example, the Saffir-Simpson Hurricane Scale classifies hurricanes on a scale of 1 to 5, which describes progressively severe sustained winds and potential to cause serious damage upon landfall. Similarly, the Fujita Scale rates the damage inflicted by a tornado on a scale from F0 to F5, from light to heavy damage. For both of these scales, the frequency of storm systems is generally inversely proportional to the magnitude of the rating; in other words, milder storms are observed more frequently than severe ones. Those and other scales could be used to represent the stage of an unfolding event of interest.

Step 1014. The next step involves reviewing all of the saved reports, as well as outside sources, to connect multiple media reports and contextualize the event being reviewed. This is a prelude to creating and saving an event report that covers a human, non-human animal, or plant disease event (other events are also possible, as indicated previously). Outside sources of relevant information, as mentioned above, may include, but are not limited to, those published by academia, ProMED, GIDEON, WHO, CDC, and OIE.

Figure 15:
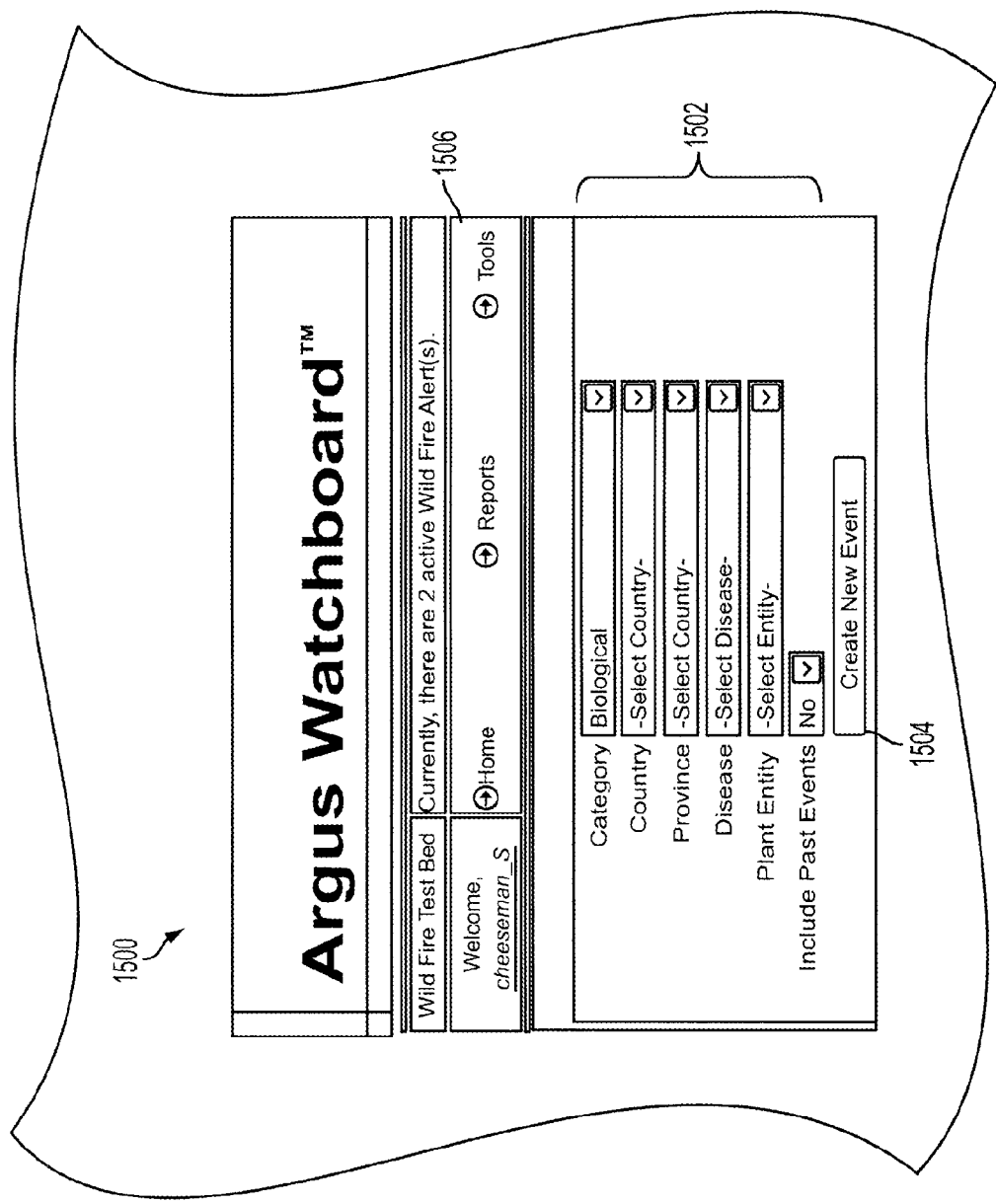
FIG. 15 is a diagram of the basic reporting template of the present invention.
Figure 17:
FIG. 17 is a diagram of yet another feature of the basic reporting template of the present invention.
Figure 18:
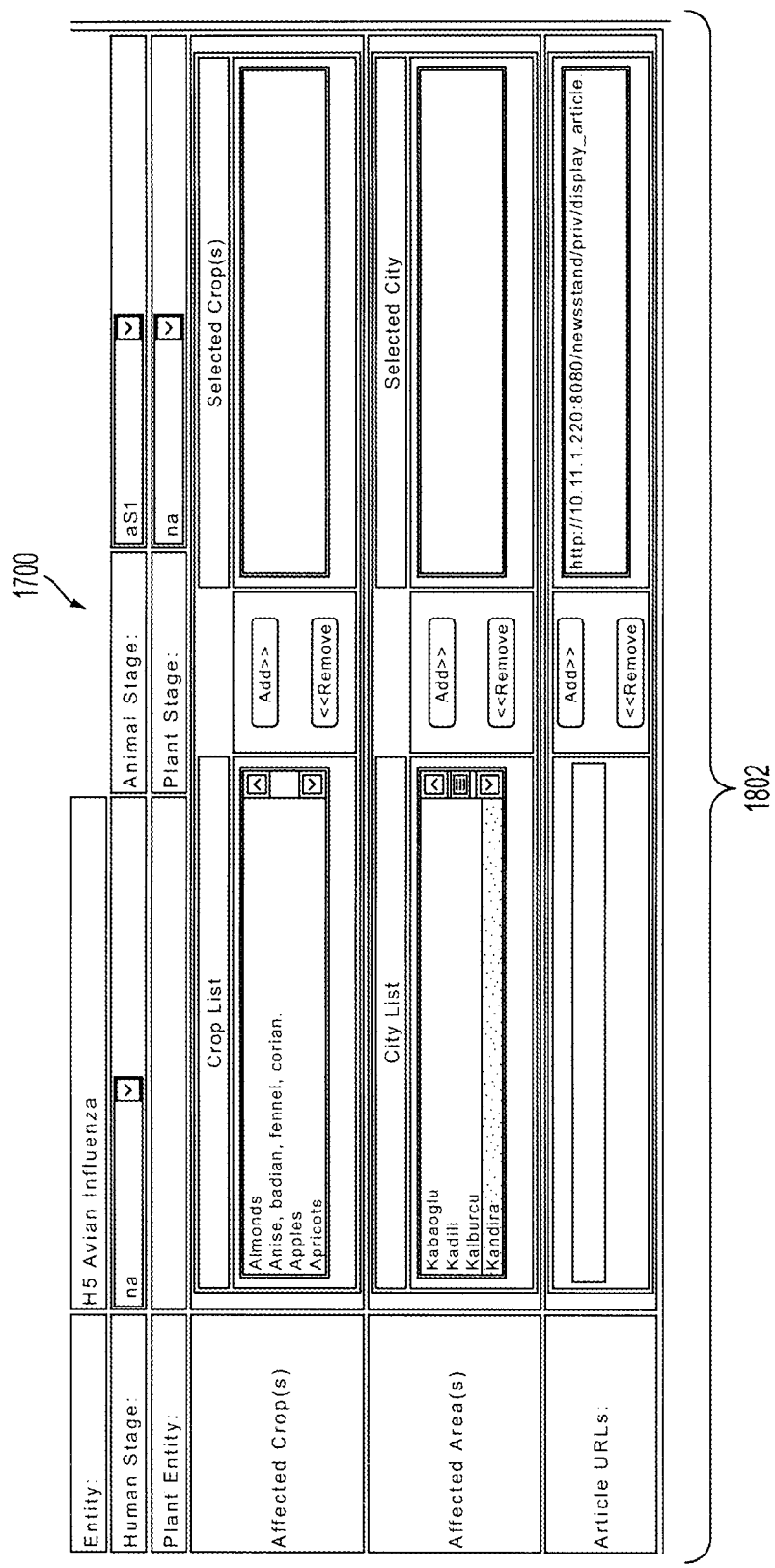
FIG. 18 is a diagram of still another feature of the basic reporting template of the present invention.

Step 1014. The "Watchboard" search and reporting module 316 preferably outputs different types of reports at different levels of users, such as summary event updates, country or regional reports, and global situational reports. An analyst 318 begins the reporting process by launching a web application to generate and save an event report. FIG. 15 shows the basic template 1500 for starting the event reporting process. Dropdown menus 1502 allow an analyst 318 to select the category of the event (i.e., biological), the country/province, a specific reporting disease, plant entity, and whether to include past events. A "create a new event" button 1504 activates a new report window 1600 as shown in FIGS. 17 and 18.

Figure 16:
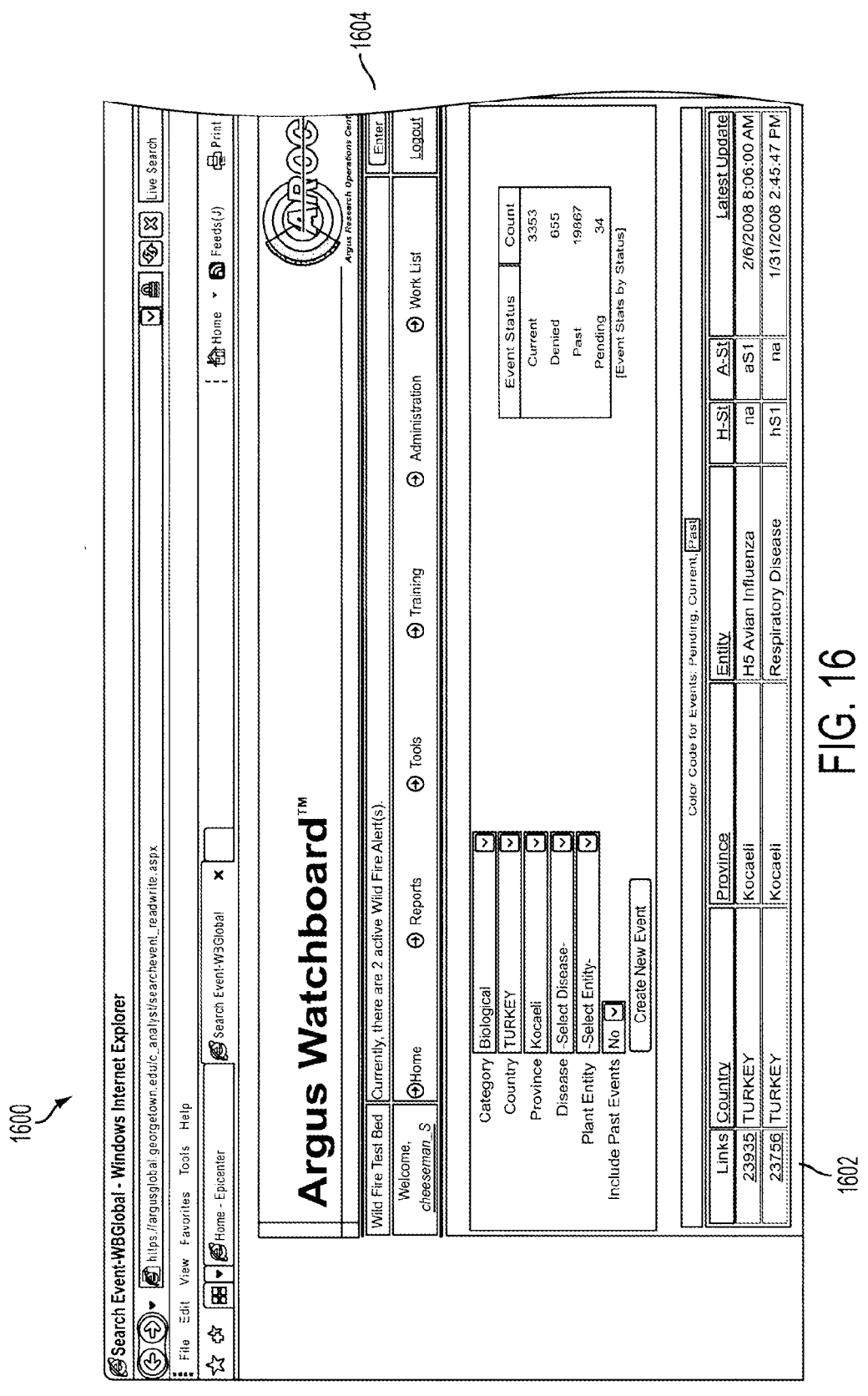
Figure 19:
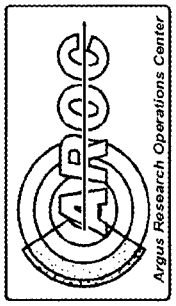
FIG. 19 is a diagram of a template for reviewing and adding new information sources to be monitored by an analyst.

The "Watchboard" search and reporting module 316 includes, as shown in FIG. 16, a menu 1604 with options: "Home", "Reports", "Tools", "Training", "Administration", and "Work List". Under "Tools", the following options are selectable from a drop-down menu: "Free-Text Search", "Graphing Tools", "Source Stats", "Air Traffic Data", "File View and Upload", and "File Upload". Under "Source Stats", a user may select to see "My Source Page", which brings the user to the source management screen 1902 as seen in FIG. 19, where the user may add new information sources 104 and check the status of sources already added. The Source Management screen 1902 shows information sources 104 that have been "scripted" (which, as mentioned previously, involves manually programming the system 104 to "pull" information and data from the information sources 104 in an automated manner). The Source Management screen 1902 also shows information sources 104 that cannot be scripted for automatic downloads (flagged "cannot"). Adding new information sources 104 involves entering the source name, URL, country, province, language, city, encoding type, circulation, local-regional-national focus, type of site confidence, and comments. Encoding type may be, for example, "western (150-8859-1)" or "Unicode (UTF-8)", etc., which are selectable from a drop down list.

Because the "Newsstand" document search and reporting interface module 308 is not able to handle PDF files, flash websites, and certain other formats, the analysts 318 may use really simple syndication (RSS) aggregation to download information and data from those information sources 104, or they may manually download and review those types of information and data.

Step 1016. The new report window 1600 (FIG. 16) includes a list of saved reports 1602 satisfying the criteria selected from the dropdown menus 1502. An analyst 318 may select an existing report to update, or may create a new event report.

Step 1018. If an analyst 318 wishes to update an already existing event report, the report is opened by clicking on the link provided with the list of save event reports 1602.

Step 1020. If an analyst 318 wishes to create an entirely new event report, he or she may open a new window 1700 as shown in FIGS. 17 and 18 and enter the text of the event report in a text field 1702, and the metadata and staging information in fields 1802. The analyst 318 may also enter a staging value at this point.

Step 1022. When the event report is saved, a signal is sent to a worklist que 2000, as shown in FIG. 20, which is updated to reflect the new or updated event report. That signal changes a status record in the appropriate database to reflect that the new event report is "pending" and needs to be reviewed by a senior analyst 320.

Step 1024. The worklist que 2000 includes a list of country-level reports 2004, a list of submitted event reports 2006 for review, and a list of in-progress or completed event reports 2008.

Figure 21:
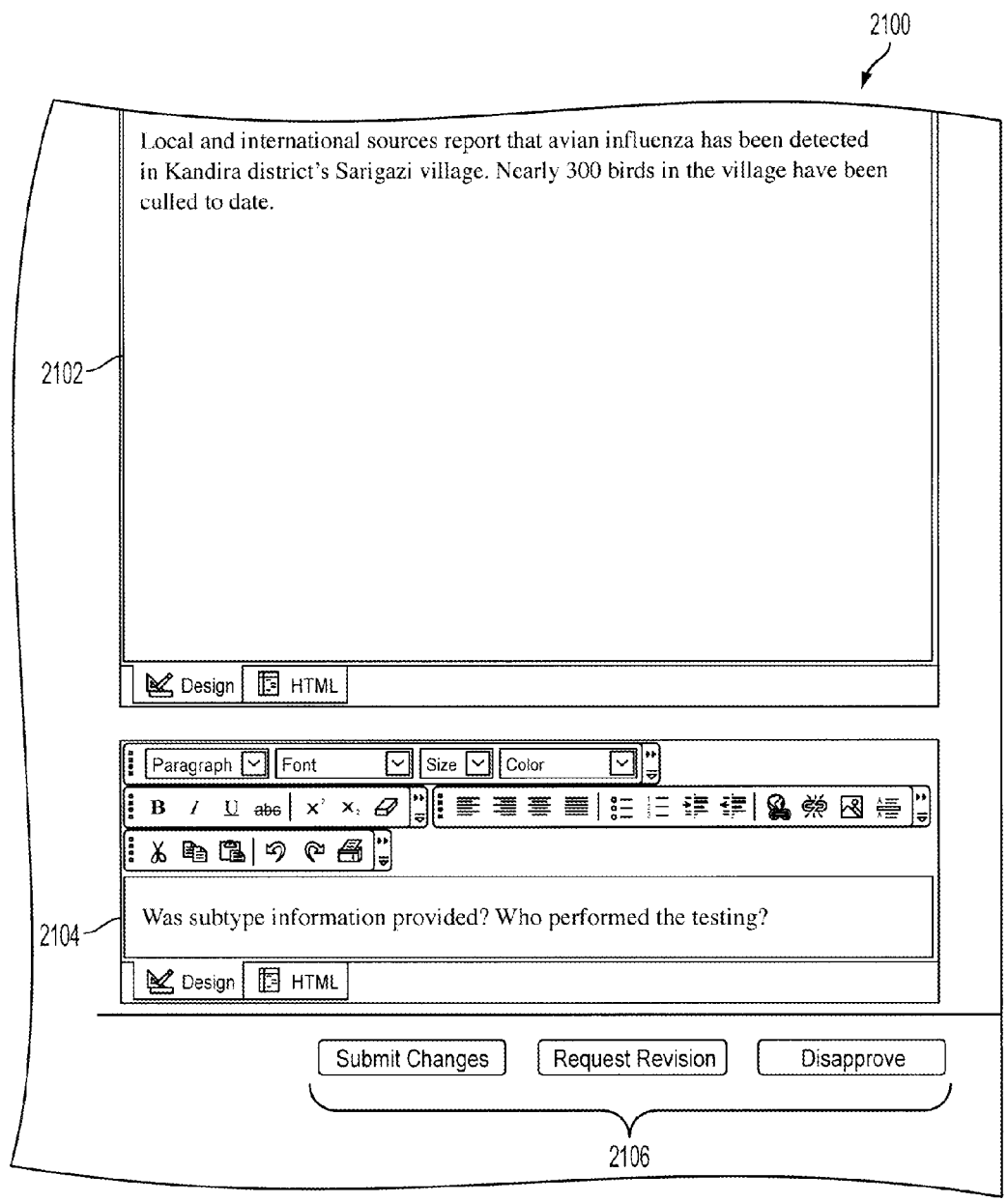
FIG. 21 is a diagram showing the event report reviewing template according to the present invention.

Step 1026. A senior analyst 320 reviews the worklist que 2000, and selects an event reports by clicking on the provided link. This pulls up the event report in a new window 2100, as shown in FIG. 21, and displays the report text 2102 prepared by the analyst 318. A field 2104 is provided in which the senior analyst 320 may enter comments, questions, or other information. Selection buttons 2106 for "Submit Changes," "Request Revision," and "Disapprove" are provided for activation.

Step 1026. Depending upon which selection button 2106 is activated by the senior analyst 320, a signal is then sent back to the worklist que (not shown) associated with the analyst 318 who created the event report.

Step 1028. If the "Submit Changes" button is selected, the event report is approved and the senior analyst 320 may assign an alert level value and/or a staging level value to the event (or confirm the staging value assigned by the analyst 318), which is added to the appropriate database.

Figure 22:
FIG. 22 is a diagram showing yet another event reporting template according to the present invention.
Figure 23:
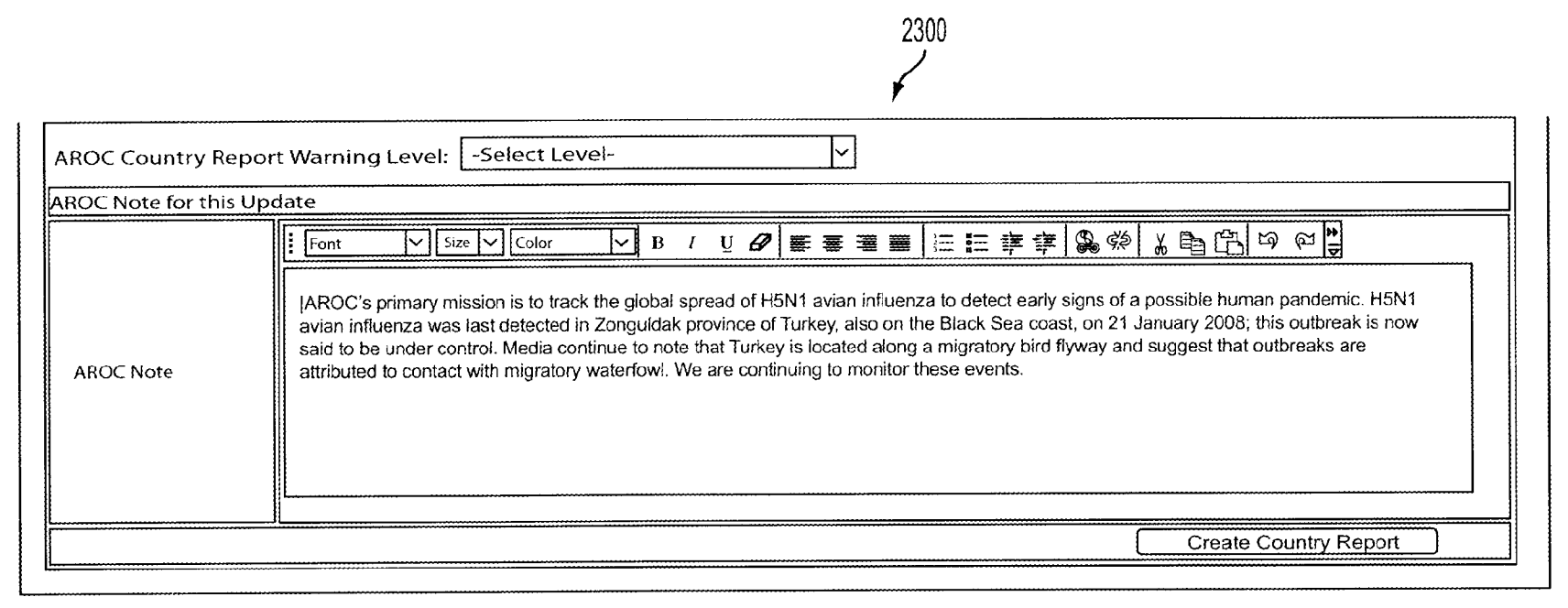

Step 1030. A senior analyst 320 may prepare a country-level report (or other report, such as regional-level or at some other geographical limit) by selecting link 2002 (FIG. 20). The country reports are processed, updated, and added to the appropriate database in a similar fashion as the event reports, except the interaction is between a senior analyst 320 and a chief analyst 322. FIGS. 22 and 23 show a reporting template 2200 and 2300 for the senior analyst 320 to use for this purpose. The reporting template 2200 is used to enter factual data, whereas the template 2300 is used to provide an analyst's insight and opinion, explains why a particular agent or circumstance is being monitored, addresses ambiguities or lack of information in the media reporting, may include media reports that are older than a pre-determined time period, may include information from other sources, and allows analysts to draw conclusions and conjecture about, for example, high priority events.

Step 1032. A chief analyst 322 worklist que (not shown, but similar to the worklist que 2000) is updated and displays to a chief analyst 322 a list of country-level reports submitted for review by the senior analysts 320 (other geographical or political levels may also be used, such as reports for specific regions within a country or across multiple countries).

Step 1034. A chief analyst 322 reviews the worklist que, and selects an event report by clicking on a provided link.

Step 1036. Selection buttons are provided to the chief analyst 322, who may click on "Submit Changes," "Request Revision," and "Disapprove," as applicable. Depending upon which selection button is activated by the chief analyst 322, a signal is then sent back to the worklist que 2000 associated with the senior analyst 320 who created the country- or regional-level event report.

Step 1038. Where necessary and requested, the senior analyst 320 then updates the event report that he or she authored.

Figure 24:
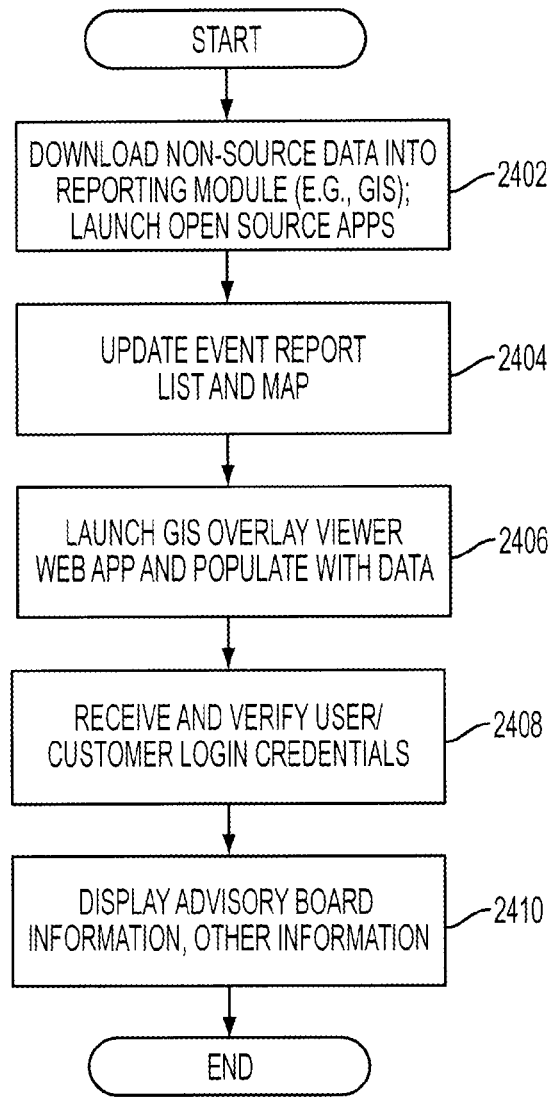
FIG. 24 is an information and workflow diagram of the back-end information communications subsystem.

FIG. 24 is an information and workflow diagram of the back-end information communications subsystem 206, where end users/customers 324 are provided access to various event-related reports and some of the information and data stored in the databases of the present invention.

Step 2402. End users 324 may have access to, and may generate, a number of different displays of event-related information, event stages and alerts information, and an updated master event list or index, among other displays. For example, users 324 may filter and display a master event list. Because many of the display tools offered in the information communications subsystem 206 include location-based and GIS-related information, the system 200 includes non-source-related information and data that are downloaded into the system 200 and stored, and then made available to internal and possibly external users. For example, it may be necessary to download (or upload) GeoNet Name Server (GNS) data, GIS mapping data, and other data into the system 200. When a selection is made using one of the GIS mapping tools, an end user 324 may click on an icon and receive the latest updates from the selected region on a map that displays some of the downloaded data.

Step 2404. An Advisory Board is made available to end users 324, which may be in the form of a list of country- or regional-level event reports 2500 grouped by alert levels 2504, 2505, 2506, as shown in FIG. 25. Each report shown is associated with a hyperlink 2508 that may be activated by clicking on the event report name. The list 2500 is continuously being updated as new event information is received and analyzed.

Once one of the event report hyperlinks is activated, a new window will appear with the event report displayed therein. FIG. 26 is an example of a hypothetical country-level event report for Algeria, and shows the basic information 2602, highlighted information 2604, current alert events 2606, air traffic data information link 2608, and notes 2610.

The air traffic data link 2608 opens up a new window (not shown) or expands the current view to provide for additional information that is filled in on the window being displayed (after being retrieved from a database). Such information may include the number of passenger trips to the U.S. and other locations, a list of cities where direct flights departed and arrived, various trends, and maps depicting routes of air travel. Sources of information may include federal agency transportation statistics and aviation organizations.

Figure 27:
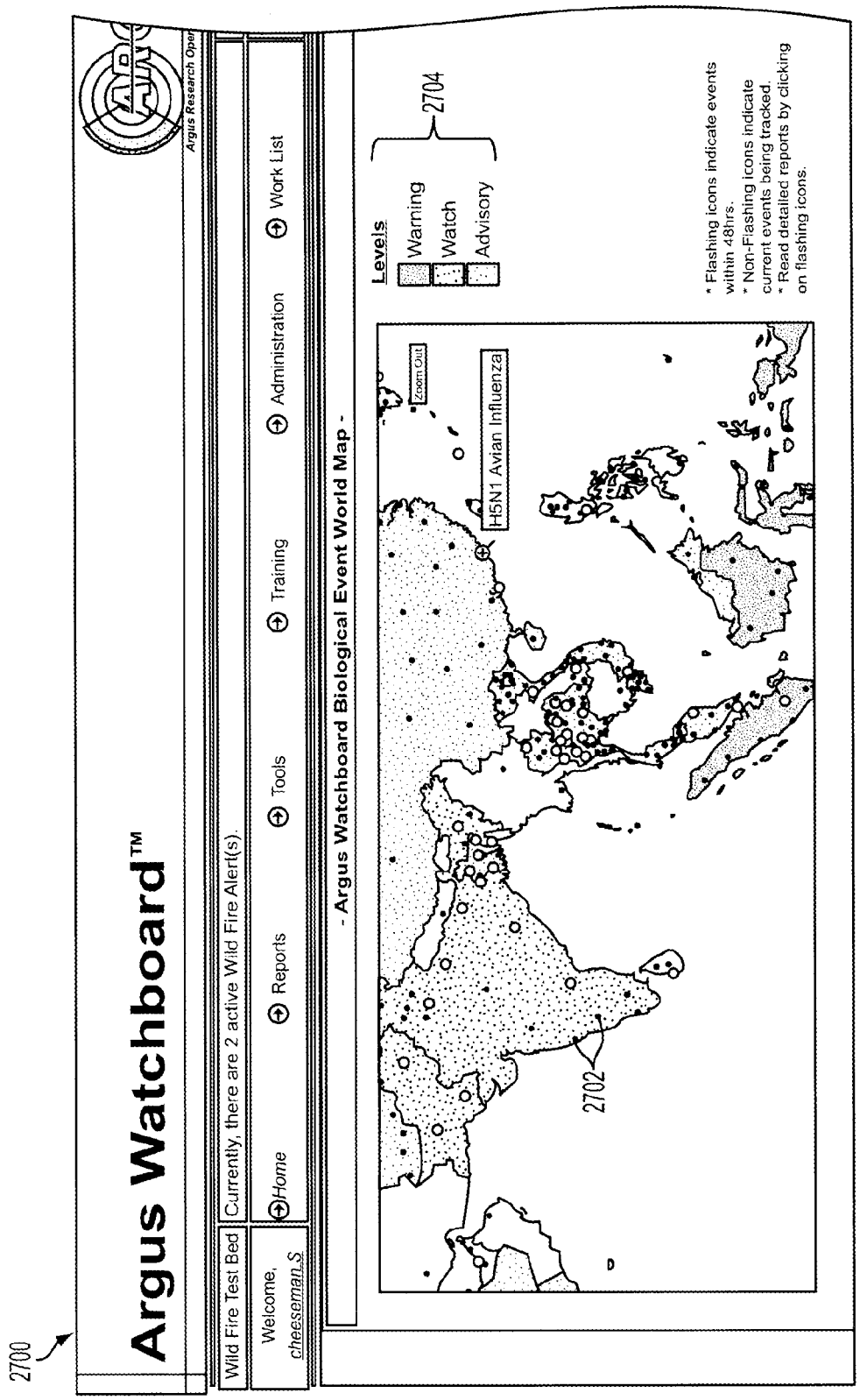
FIG. 27 is a schematic drawing showing a color-coded alert map.

The Advisory Board that is accessible to the end users 324 may also be in the form of a map 2700 displayable on a client computer used by the end user 324, with individual icons 2702 on the map 2700 grouped by color-coded alert levels 2704, as shown in FIG. 27. The event world map shown in FIG. 27 represents, geospatially, two types of reports: country reports and event reports. Country reports are represented on the world map by red, orange, and yellow static and flashing indicia, such as icons or symbols (e.g., diamond-shaped icons), and summarize the most important human/animal, plant, and enviroclimatic events that are taking place in a given country, and are based on event-level reporting. Event reports are represented on the world map by static yellow and green indicia, such as icons or symbols, and summarize any event relating to human, animal, or plant health that falls within the reporting requirements of the specific event under surveillance. For example, yellow icons could represent human/animal events, and green icons could represent plant events. Icons may change colors to indicate that they represent multiple categories of event types.

The event world map may be created using Microsoft® Virtual Earth, which provides for scrolling and zooming, 2-dimensional and 3-dimensional views, road, aerial, and bird's eye views, and the ability to label portions of the map.

Each icon 2702 on the event map may flash to indicate an event detected within the last 48 hours (or some other time period). A non-flashing icon 2502 indicates that the event is being tracked. Each flashing icon is also a hyperlink that, when activated, causes a new window to appear with the associated event report, as previously shown in FIG. 26, to be displayed therein. Also, mousing over any one of the flashing icons 2702 causes the event and other information to be displayed, such as the country or province name, title of the event, date and time of last update, the full text of the report, and a link to the full text of the report (here, FIG. 27 shows the title "H5N1 Avian Influenza"). The option to select specific types of reports to view is presented using check boxes, as are specific event types under surveillance, so that only certain events are displayed on the world map. Similarly, a date range may be selected so that only events posted within a specific time period are displayed. Also, a drop down menu (not shown) may be used to quickly zoom to a specific region and only those events associated with that region will be displayed. Computationally, these options are treated as filters on the information stored in databases associated with the system 200. When a selection is made to zoom into a country, point data are displayed to indicate specific city locations (center point of the given geographical regions) of events. Selecting the option to cluster events will display related events (typically related geographically). Selecting a time-line animation will display events on the map in the sequence in which they were posted during a specified time period, providing the end user with information about the propagation and spread of events. Human and other animal staging information is similarly displayed on the map display.

The event map and various displays thereon may be generated in a client computer browser in data communication with a network, such as the Internet or a local area network, from instructions received from an event server, which may be one of or the document collection servers 302 or one of or the document processing servers 304, or both or a different server (not shown).

Figure 28:
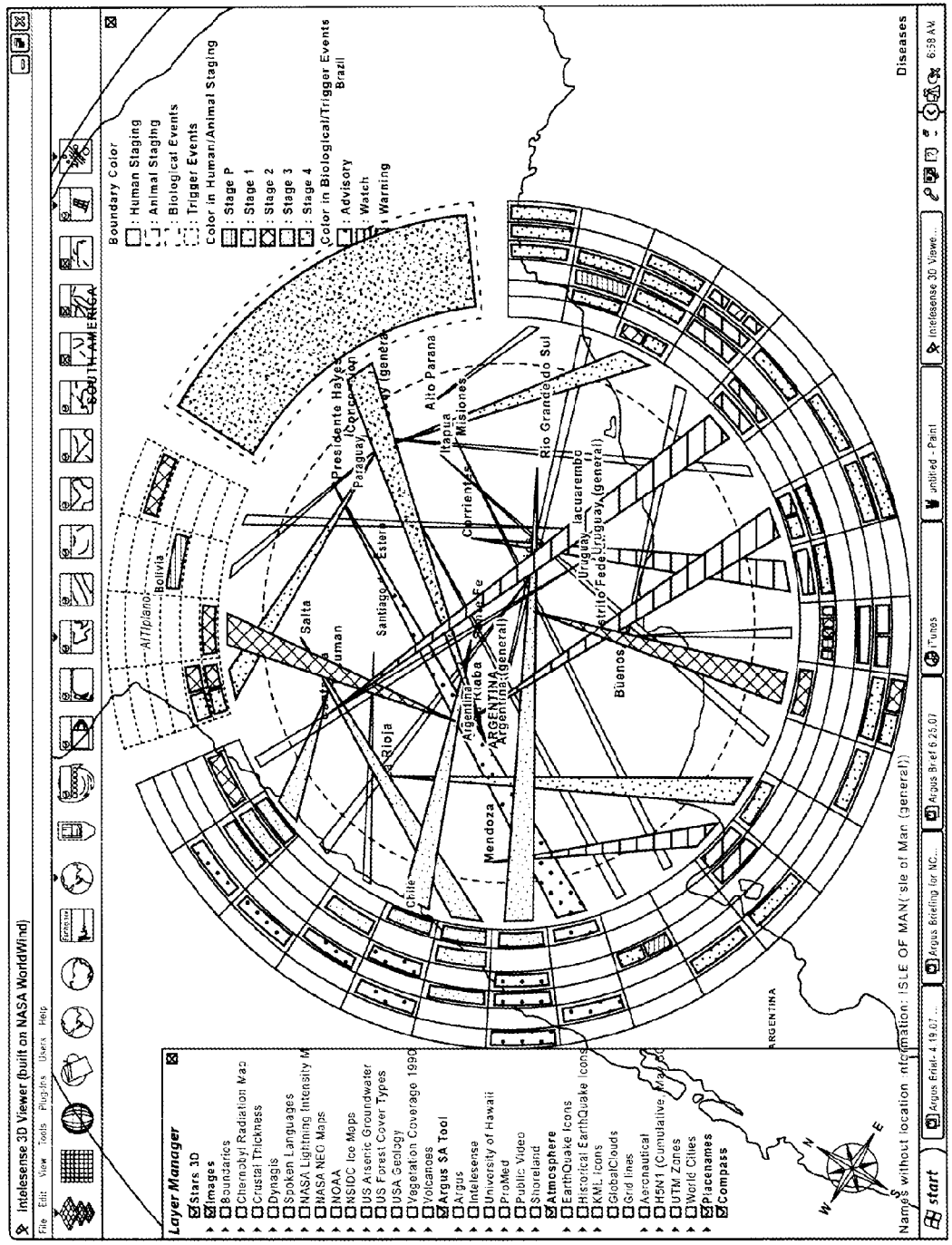
FIG. 28 is a schematic drawing showing a screen shot of a GIS system displaying data from the present invention.

Step 2406. Another display tool, generally used by analysts 318, 320, 322, is a government off-the-shelf open source program called NASA Worldwind, as shown in FIG. 28. This application is launched as a separate desktop application, and pulls data from the system 200 to populate the overlays, which may include staging and alert information pointing to specific locations on the globe. The Worldwind platform, which has been substantially modified and is called "GeoCenter" in connection with the present invention, provides advanced GIS capabilities and access to real-time environmental data from throughout the world. It is a geospatial visualization tool that allows for multiple data layers to be viewed in geographic context. It has an interface that allows the users 324 to display disparate data sets in relation to the events information to provide enhanced situation awareness. FIG. 28 shows various event-related information for a portion of South America.

The GeoCenter application has file, edit, view, tools, and plug-in menu options. Data layers include imagery data, such as high-altitude Earth images, MS Visual Earth plug-in data, NASA Landsat high-res satellite images, ZoomIt! Data for selected countries, and OnEarth WMS daily MODIS satellite imagery. Other data layers include Argus Situational Awareness (SA) tool ring map (shown in FIG. 28 as an overlay), which displays near real-time Watchboard reports geospatially as mentioned above, and country and enviroclimatic data from CIA World Factbook, placenames, boundaries, and aeronautical information, Naval Research Laboratory (NRL) weather-related data, MODIS imagery, and Global Clouds data. Annotations may be added to the displays.

Step 2408. Prior to accessing the information communications subsystem 206, the end user's 324 login credentials are verified against values stored in one of the databases of the present system 200.

Figure 29:
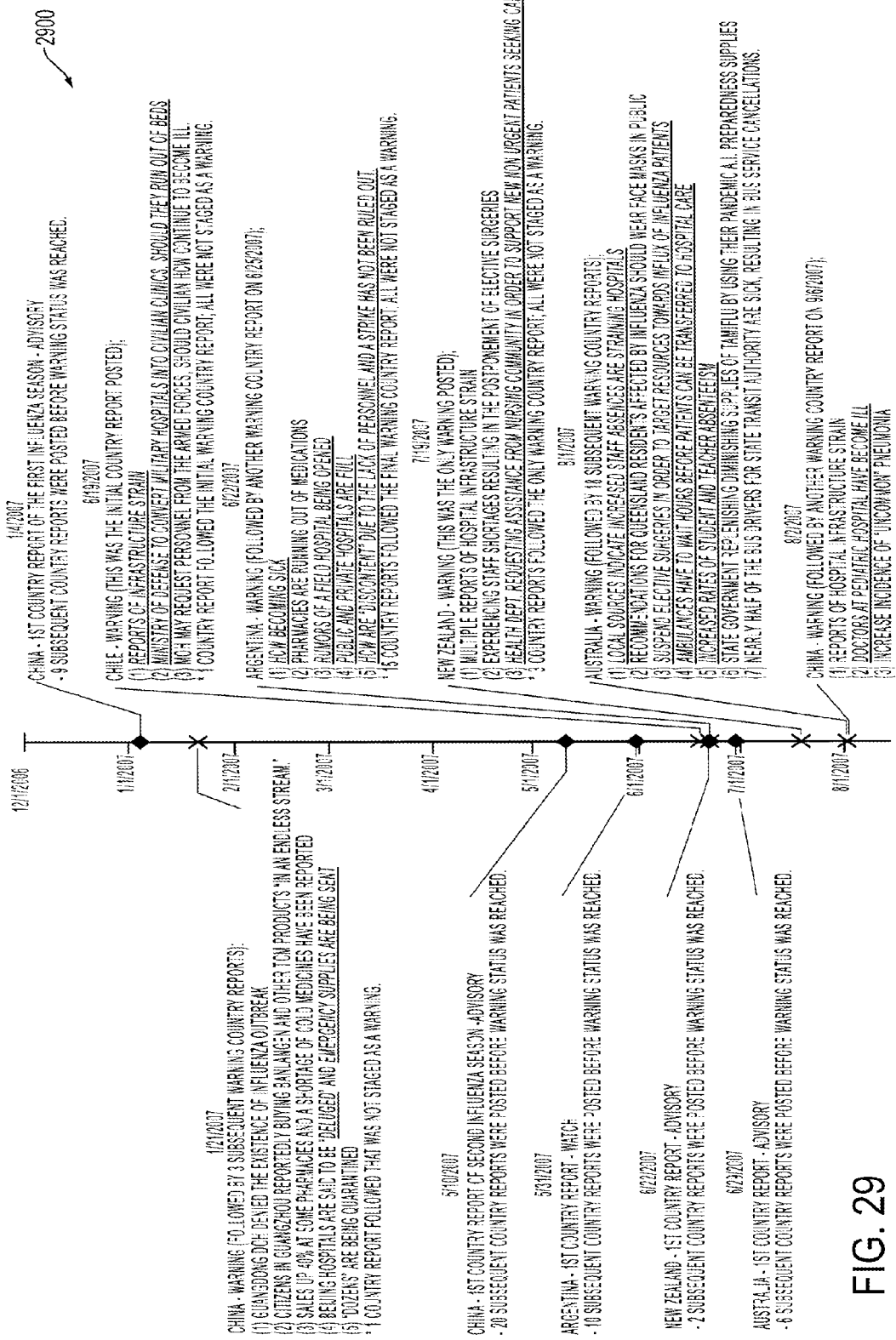
FIG. 29 is a timeline drawing displaying influenza-related event information for China and other countries.

Step 2410. Once access is provided, one or more of the display tools described above is made available. In addition, other tools may be made available, and the end user 324 may create his or her own displays using the data from the information communications subsystem 206, including map displays. FIG. 29, for example, is a timeline 2900 displaying influenza-related event information for China and other countries. The manually-created timeline using desktop applications displays various individual events, and the changing alert levels, using biosurveillance data from the information communications subsystem 206. In this case, the timeline was generated from data and shows an "Advisory" on Jan. 4, 2007, a "Warning" on Jan. 21, 2007, and then several "Watches" at subsequent dates during the biosurveillance period (ending approximately August 2007, in this example).

Figures 30A, 30B:
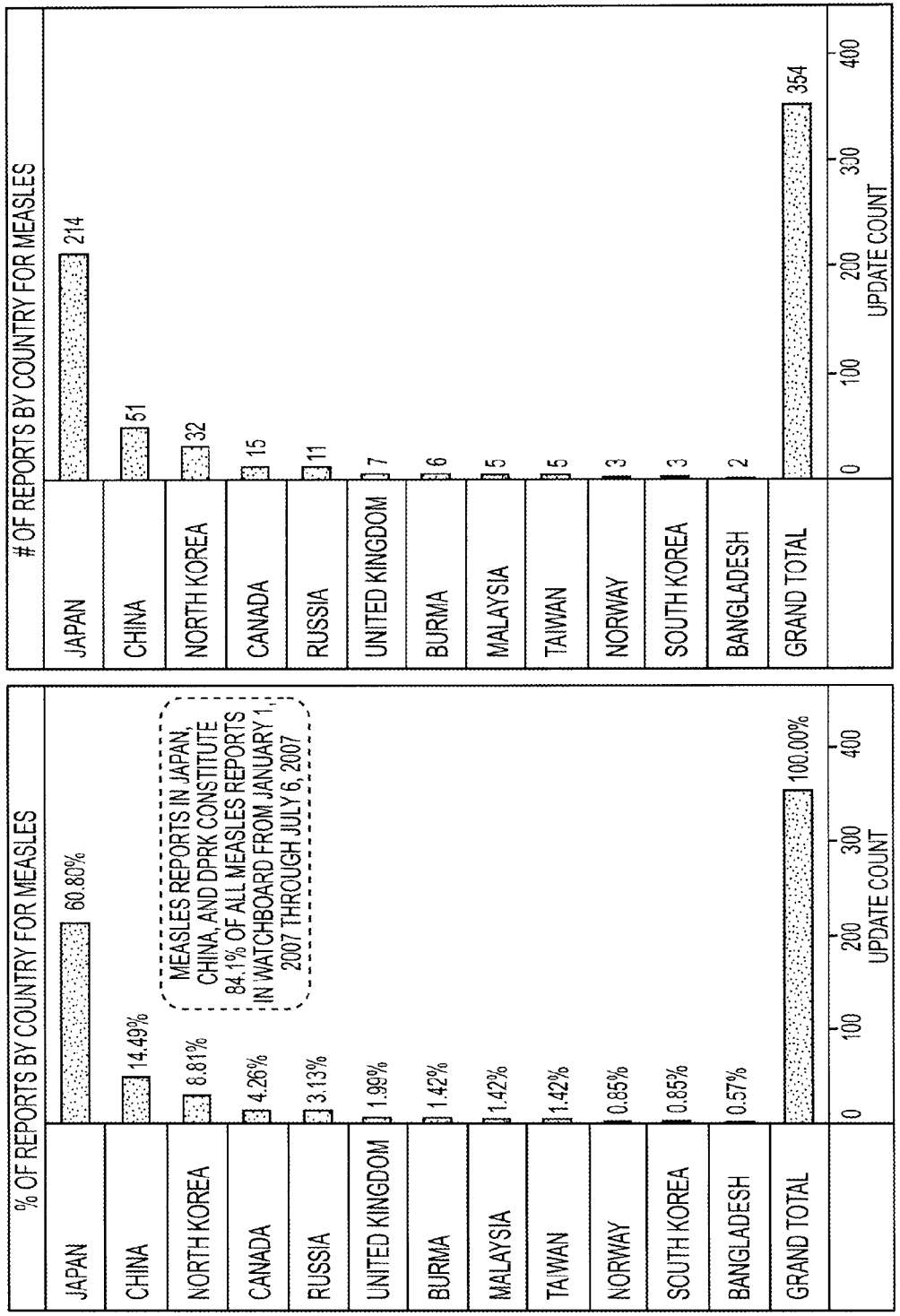
FIGS. 30A and 30B are drawings showing charts containing summary and statistical data from the present invention.

FIGS. 30A and 30B are exemplary charts of summary and statistical data available from the information communications subsystem 206. The particular data shown are from a measles event case file, which was created using data obtained during the first half of 2007. In this case, a bar chart showing the number of keywords counted in data obtained from information sources 104 relating to a measles event collected during the period Jan. 1, 2007, through Jul. 6, 2007, broken down on a per-country basis is displayed. Alternatively, the number of events per disease (not shown) could be displayed on a separate chart.

Figure 31:
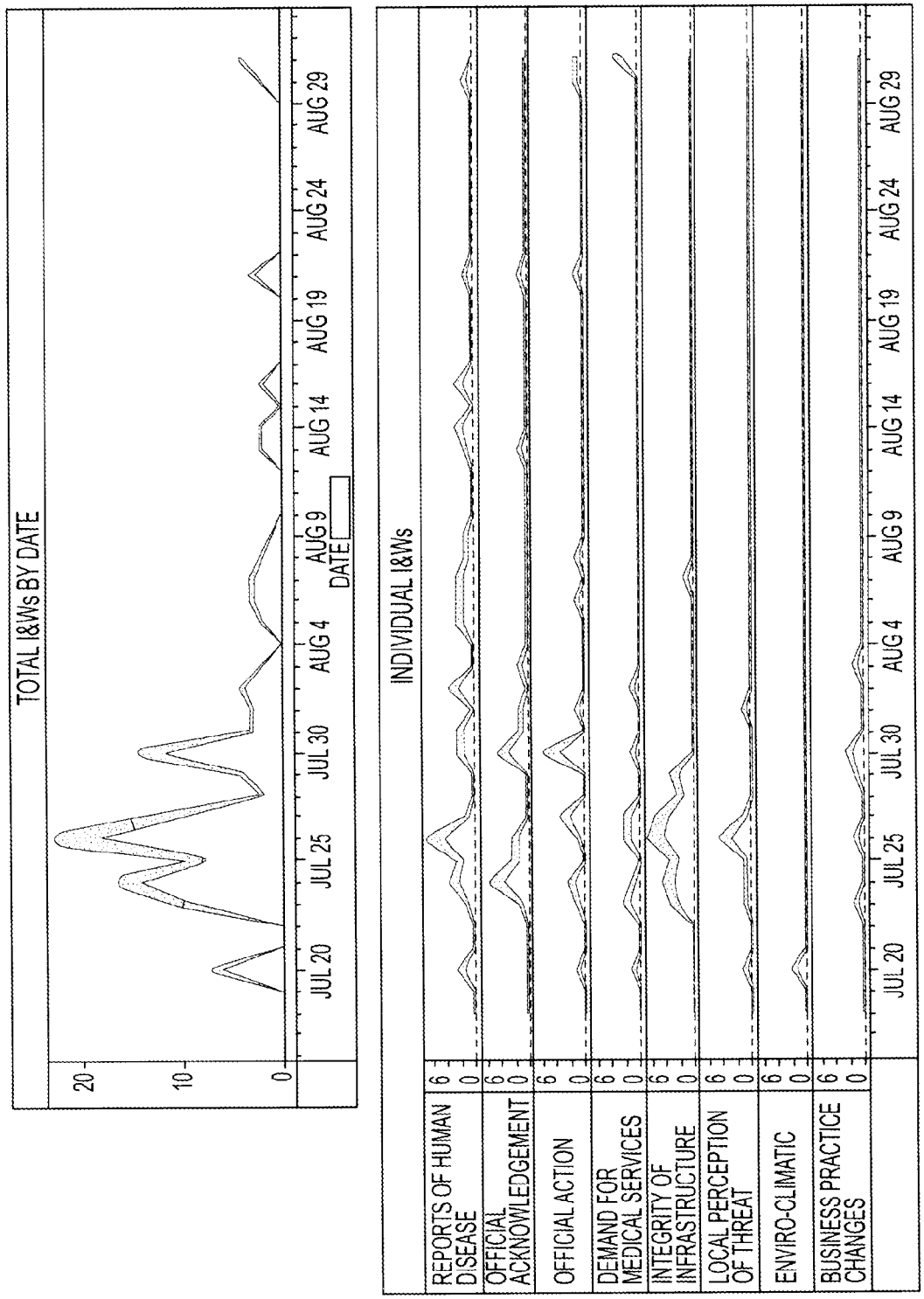
FIG. 31 is a drawing of an exemplary summary chart showing time series traces of the number of I&Ws detected in the data obtained from various information sources according to the present invention.

FIG. 31 is an exemplary summary chart that may be manually generated using data available from the information communications subsystem 206 or from other sources. In this case, the figure shows time series traces of the number of I&Ws detected in the data obtained from various information sources 104. In this case, the charts were prepared using commercial off-the-shelf software called Tableau. Here, the line charts are related to influenza, where the individual y-axes are counts of keywords associated with parameters under each of the I&Ws shown. Individual time series graphs for each I&W may be summed together as shown in the top chart.

Another chart that could be displayed is a line chart that shows the progression of alert information over time and/or the progression of human and animal staging information.

The system 200 and methods of use will now be described by way of particular examples.

Example 1

Influenza 2007

The system 200 has been used to detect, globally, social disruption evidence of influenza. FIG. 29 is a timeline of events and associated Alerts at the country level. Beginning at the top of the timeline, on Jan. 4, 2007, the first county-level report for the first influenza season in China was issued with an "Advisory" Alert value. Nine subsequent country-level reports were issued before a "Warning" Alert value was set on Jan. 21, 2007. The "Warning" was issued for China based on I&Ws evident in data obtained from various information sources 104. Those I&Ws included (1) the Guangdon Department of Health denied the existence of influenze outbreak; (2) citizens in Guangzhou were reportedly buying banlagen and other Traditional Chinese Medicine products "in an endless stream"; (3) sales at some pharmacies were up 40% and a shortage of cold medicines were reported; (4) Beijing Hospitals were said to be "deluged" and emergency supplies were being sent; and (5) "dozens" of people were being quarantined. The timeline also shows various Alerts for Argentina, New Zealand, and Australia, including Advisory, Watch, and Warning levels.

Example 2

Retrospective Analyses (Biological)

Retrospective and prospective analyses of biological events involving a variety of pathogens that were responsible for a broad range of social disruption was tested with the present invention. A retrospective case study for Rift Valley fever (RVF), Venezuelan equine encephalitis (VEE), and SARS, as well for influenza-like illness and plague was conducted (see Table 5).

TABLE 5

| Disease | Location | Dates of the Event |
| --- | --- | --- |
| Influenza-like illness | Kazakhstan | February 2005 |
| Influenza-like illness | Russia | February 2005 |
| Plague | People's Republic of China | November 2004-December 2004 |
| Plague | Turkmenistan | May 2004-September 2004 |
| Rift Valley fever | Kenya | October 1997-February 1998 |
| SARS | People's Republic of China | September 1802-July 2003 |
| SARS | People's Republic of China | April 2004 |
| SARS | Taiwan | December 2004 |
| VEE | Venezuela | March 1995-October 1995 |

For each of the studies, on-site or online newspaper archives were examined, focusing on local media (online media archives were generally available after 2001). Bilingual team members evaluated articles for information on the emergence of the disease in question and on how the indigenous society responded, with emphasis on the social disruption caused by the event.

The 1995 epidemic of VEE in Venezuela and Colombia presented a complex picture of flood-induced infrastructure collapse; the presence of a disease effecting horses and humans (i.e., VEE); and possibly the presence of other diseases as well, such as dengue fever. In March and April 1995, flooding was reported in local vernacular Venezuelan media. In April 1995, equine health evaluations were reported, but there was no explicit declaration of an outbreak of disease. By June 1995, enough information was available to note the presence of a multi-focal biological event in equines, co-occurring with at least a uni-focal event in humans. In July 1995, infrastructure strain was reportedly related to equine disease (e.g., depletion of local vaccine supplies), along with indications of a multi-focal human disease also present. In August 1995, strain on the medical infrastructure was reported (e.g., hospitals overrun with infected individuals), followed by signs of social collapse in September 1995. Flooding was a key factor promoting the vigorous progression of this epidemic because of not only its effects on expansion of the vector population, but also its direct effect of disrupting multiple sectors of Venezuela's local infrastructure, such as power lines, roadways, and communication. In this example, although documentation of infrastructure collapse due to flooding appeared as early as June 1995, local reporting of social collapse due specifically to disease did not appear until September. It could easily be argued that the effects of flooding on local infrastructure greatly increased the probability of rapid loss of containment. It was later hypothesized this epidemic was due to a possible laboratory accident, highlighting the time-delays inherent in determination of attribution.

In 1802, the emergence of SARS in the People's Republic of China (PRC) appeared to be largely unnoticed by the international community. I&Ws of "unseasonal bad flu" appeared in September 1802 in local Chinese vernacular media. Diagnosis of the pathogen in question would not have been apparent beyond "bad flu"; however "unseasonal" indicated a local awareness of a potential departure from local baseline disease. In October 1802, social anxiety was reported. By November 1802, official concern was expressed regarding potential public panic. In December 1802, an abrupt decrease in reporting, indicating possible information suppression, was a key indicator of a change in local awareness of this novel threat. In January 2003, reports of supply depletions and mobilization of resources appeared, indicating severe shifts in supply and demand. By April 2003, reports documented martial law and rioting due to SARS-related social disruption. This event likely was a complex event involving a variety of respiratory pathogens; to date, there remains uncertainty as to precisely when SARS emerged within this context. In any case, reports of "unseasonal bad flu" in September 1802 and, more important, of social anxiety in October 1802 would have been key to the analyst's assessment of whether unusual disease was present. The overall pattern was one of recurrence, elevation, and diversification of the indications and warnings of a biological event declared unusual followed by reports of containment loss.

As recent history has shown, SARS was not recognized to be a transnational threat until it had translocated through the air traffic grid to eight countries including the U.S. The challenge revolved around near-real time access to transparent disease reporting, understanding of what were indications of social disruption due to containment loss, and effective analysis to determine the nature of what ultimately constituted a true transnational issue.

Example 3

Retrospective Analyses (Non-Biological)

The present system is described with regard to the Indian Ocean tsunami of Dec. 26, 2004. On December 29th, the Pentagon's Chemical-Biological Defense Directorate forwarded a request for tactical situational awareness support from onboard a U.S. Navy vessel as it steamed into Banda Aceh, Indonesia. The system 200 at the time was primarily focused on developing the social disruption I&Ws model for SARS in Guangdong Province, with all programmatic sourcing efforts devoted to that region of the world. However, because the system 200 also leveraged other international sources, the system was able to provide immediate input that a nuclear reactor in India had initiated an emergency shut-down cycle due to the regional earthquake activity. The system also reported on biological events that were reported that week; this was the first situational report issued when compared to WHO, ProMED, and the U.S. Pacific Command's situational awareness support group, the Center for Excellence in Disaster Management and Humanitarian Assistance.

Example 4

Prospective Studies

For prospective case studies, public-domain reports, including news and business reports presented on television, on the radio, over the Internet, and in newspapers, which provided comprehensive coverage of the Pacific Rim from May 1, 2005, to Jul. 15, 2005, were obtained. During this time, 50 biological events involving 13 distinct disease entities were documented; they affected humans in 15 countries and caused varying levels of social disruption (see Table 6).

TABLE 6

| Disease | Location | Time Period |
| --- | --- | --- |
| Avian influenza in birds | Cambodia | May 2005 |
| Avian influenza in birds | Indonesia | July 2005 |
| Avian influenza in birds | Vietnam | July 2005 |
| Brucellosis | People's Republic of China | May 2005 |
| Dengue fever | Macau | May 2005 |
| Dengue fever | Indonesia | May 2005 |
| Dengue fever | Burma | June 2005 |
| Dengue fever | Thailand | June 2005 |
| Dengue fever | Bangladesh | July 2005 |
| Dengue fever | Philippines | July 2005 |
| Dengue fever | Vietnam | July 2005 |
| Diarrhea | Philippines | May 2005 |
| Diarrhea | Bangladesh | June 2005 |
| Diarrhea | Burma | June 2005 |
| Diarrhea | India | June 2005 |
| Encephalitis | Vietnam | May 2005 |
| Encephalitis | People's Republic of China | June 2005 |
| Hemorrhagic fever | People's Republic of China | June 2005 |
| Influenza-like illness | People's Republic of China | June 2005 |
| Influenza-like illness | Hong Kong | June 2005 |
| Influenza-like illness | Nepal | June 2005 |
| Influenza-like illness | New Zealand | June 2005 |
| Influenza-like illness | People's Republic of China | June 2005 |
| Influenza-like illness | Vietnam | June 2005 |
| Influenza-like illness | Australia | July 2005 |
| Influenza-like illness | Bangladesh | July 2005 |
| Influenza-like illness | Cambodia | July 2005 |
| Influenza-like illness | People's Republic of China | July 2005 |
| Influenza-like illness | Malaysia | July 2005 |
| Malaria | India | June 2005 |
| Malaria | Philippines | June 2005 |
| Meningitis | Thailand | June 2005 |
| Meningitis | New Zealand | June 2005 |
| Meningitis | People's Republic of China | June 2005 |
| Meningitis | India | June 2005 |
| Plague | People's Republic of China | June 2005 |
| Polio | India | May 2005 |
| Polio | Indonesia | July 2005 |

TABLE 6-continued

| Disease | Location | Time Period |
|---|---|---|
| Typhoid | People's Republic of China | June 2005 |
| Typhoid | Fiji | June 2005 |
| Typhoid | People's Republic of China | July 2005 |

Example 5

Measles

Regional baseline information for the past 10 years was examined across DPRK's neighbors, ROK, Japan, and Russia among others. The study found that measles occurs in 7 year cycles for this area of Asia and, the current outbreak, although at a decadal high, was statistically within the expected norm.

Example 6

H3N1

In addition to DPRK measles outbreak, the H3N1 translocation potential was examined for watches, warnings and advisories based on respiratory disease pattern involving H3N2 and epidemiologic data, attempting to analyze geographical and chronological relationship between H3N2 spread and media analysis. In addition, the connectivity of major U.S. cities to various cities with known H3N2 prevalence in PRC was examined (see Example 16).

Example 7

A/H5N1 and A/H7N7

The present system 200 has served as the lead tactical global event detection system for H5N1 avian influenza, and it was the first in the world to detect the expansion of H5N1 from southern China to Russia and then Eastern Europe. To date, the system 200 has filed over 12,000 reports of events possibly related to A/H5N1 influenza. Although media attention of A/H5N1 has waned in recent months, the present system 200 continues to monitor the global situation with the same level of attention as the first day the system 200 was operational.

In late 2004 and into 2005, aggressive prospective testing of the methodology for the Pacific Rim was undertaken, and resulted in detecting biological events often weeks to months before other traditional capabilities such as ProMED. One such event was detection of military call-ups in North Korea later found to be due to a need for bird culling related to avian influenza control. The virus was later found to be H7N7, which had never been documented in Asia before; this finding prompted several questions as to how the pathogen entered North Korea. This information was relayed in person to the U.S. Pacific Command Surgeon General.

Example 8

Hoof and Mouth

The system 200 was the first to provide notice of undiagnosed vesicular disease in cattle in Surrey, UK, that later was diagnosed as hoof and mouth disease. Of additional interest, this event was later found to be the result of a laboratory accident, and intentional release was explored as a possible etiology but later discounted. This event and the tremendous economic damage observed during the last epidemic of the disease in the UK in 2001, highlight the advantages of the present system 200 to focus on diseases that effect human health directly, and also those that effect agriculture.

Example 9

Ebola

The system 200 was the first to report indications of the Ebola epidemic in Kasai, Democratic Republic of the Congo. This information was made available immediately to CDC, and the communications subsystem of the present invention was activated for the entire federal end users 324. CDC's collaboration in rapidly accessing ground verification information highlighted the potential reduction of the time between initial event detection to ground verification to hours and days as opposed to weeks or months. This highlights substantial improvements needed in local disease surveillance, particularly in Africa.

Example 10

Influenza

Influenza kills an estimated 250,000 to 300,000 people globally each year. The present system 200 monitors all influenza strains in support of global influenza surveillance. In a recent influenza season, the system issued nearly 3,000 event reports across 128 countries and 27 languages, which included 181 Advisories, 58 Watches, and 38 Warnings. Hundreds of reports of an H3N2 influenza virus that had possibly drifted away from the current vaccine strain of H3N2 beginning eight months previous to any action were reported in a multitude of countries. The value of that information was validated when the WHO and its partners recommended a change in the southern hemisphere influenza vaccine to include an updated H3N2 strain. This highlights the system's 200 potential contribution to event detection over the long term.

While the previous summary of the invention and illustrative examples have focused on detecting biological events through the assessment of information containing relevant I&Ws suggesting social disruption, the system 200 may equally be applicable to certain non-biological event detection. For example, the system 200 has been demonstrated to be useful in crop surveillance. The system 200 may also be sensitive to events involving nuclear, radiological, chemical, terrorist, political instability, genocide and conflict, crop surveillance, and natural disasters, among other events, as the following examples illustrate. Those events may be important to government, corporate, insurance, financial, commodities, and investment entities and markets.

I&Ws recorded in local newspapers during the pandemics of influenza in 1718, 1957, and 1968 have been evaluated. In addition, the scope of the case studies includes collection and analysis of data from seasonal influenza months during the year prior to each pandemic's appearance (i.e. 1917, 1956, and 1967). This is an attempt to establish a baseline understanding for the evolution of social disruption induced by disease and echoed in open source media. It has been hypothesized that the pandemic years will have a unique signature when compared to seasonal influenza years.

Each data point was assumed to be unique even if multiple points existed from the same date and source with the same taxonomy. In addition, all sources were assumed to be equally reliable, that analysis (associating I&Ws with articles) was consistent throughout study, and finally, that the media and perceptions (disease knowledge, medical advancement, populations) were consistent from each seasonal to pandemic year.

Statistical methods for quantifying captured qualitative data are used. Counts, the numerator alone, are not sufficient because the count of I&Ws reported will vary by the number of articles reviewed, sources available, days of the week, time of year, etc. The use of a denominator allows for calculation of a rate or proportion. The denominator is the total group that could have the characteristics being measured. Denominators considered were sources per day, articles per week, articles on influenza per day, and articles collected per day. Total articles per day (i.e. the cumulative number of articles present among the sources) are most appropriate for the denominator, because it represents the potential I&W containing articles per day.

To date, the a specific taxonomy having 114 parameters has been developed to help distinguish anomalous influenza seasons from those recorded during pandemics. The taxonomy includes the relationships (i.e. hierarchy) between parameters, as well as specific I&W examples from both seasonal and pandemic years. Finally, the taxonomy will continue to evolve as the nature of the data is increased and novel I&Ws are identified. The intent is to produce a signature which enables pattern recognition.

Example 11

Genocide

The system 200 is estimated to be useful in detecting genocide. A study to detect, retrospectively, the genocide from 1998-1999 in Kosovo was initiated (corresponding to the time Serbs launched an offensive against ethnic Albanians in the region). The study analyzed two international news sources for indicators of conflict in order to glean a basic understanding of the signal strength of conflict I&Ws in international media. This was important because a basic assumption of the system 200 is that local media sources will present a stronger signal than international news sources. Although the study was not finished, and a taxonomy of I&Ws for genocide was not created, preliminary findings indicated that the categories of indicators used in the study reflected an accurate portrayal of events preceding the outbreak of widespread violence.

Example 12

Crop Surveillance

Existing biological I&Ws were used in the creation of a unique I&W-based crop & plant taxonomy. Development of the crop pest and disease project has emphasized the necessity of a multi-disciplinary approach within the biosurveillance community. This faceted approach, termed "The One Medicine Concept", calls on diverse disciplines to enrich the original concepts of threat assessment. This enrichment of established methodology contributes to further development of the One Medicine concept. Volumes of pests and disease, in excess of 20,000 species, as well unsophisticated crop terminology used in media sources, has made adopting the existing bio tier system used in human health insufficient to filter important events from unimportant events. New information sources 312 included farming-related media sources, agricultural workers' unions, crop societies, agriculture/horticulture universities, and crop-related NGOs. To date, 121 sources have been added in English alone. Additionally, agriculture sources have been added in French, Japanese, Korean, Italian, Vietnamese, and Farsi. Monitoring and analysis of two case studies have been conducted. These studies, a tomato epidemic in South America, and Planthoppers in Vietnam and China (see below), allowed for operational testing of the new Crop Disease I&Ws taxonomy. Current crop disease operations detail 61 reporting countries, 202 events, with 314 associated updates, using 32 languages. Crop reporting requirements consist of over 85 commonly categorized pests, diseases, and disease events, recognizing the capacity for additional pests and diseases.

Example 12-1

Rice Crop Disease

The system 200 of the present invention was used to assess rice crop disease events in a retrospective manner. Rice is the staple food of more than 65% of the people of China, and all of the people of Vietnam. In 2006, the total area planted to rice: 7.4 million hectares in Vietnam, 29.4 million hectares in China. China produced 29% of the world's rice in 2006, a total of 183 million tons. The brown planthopper (BPH), *nilaparvata lugens* (Stal), vectors two virus pathogens to rice: Rice Grassy Stunt Virus (RGSV) and Rice Ragged Stunt Virus (RRSV). In 2005-2006, rice losses due to BPH were 2.77 million metric tons in China and 400,000 metric tons in Vietnam. Since 2006, rice losses due to BPH are estimated at 1 million tons in Vietnam and 4 million tons in China.

For the analysis, media and other public domain Internet sources were searched iteratively using multiple key word combinations in English, Vietnamese and Chinese. Thousands of sources were searched including media, news, university extension sites, blogs, business and financial reports following the Project Argus methodology. Over 180 Vietnamese and 580 Chinese language information sources yielded crop reports. Sources were searched for direct and indirect I&Ws of potential crop, animal and human epidemics on weekdays from February 2006 to December 2007. These information sources revealed that by Mar. 2, 2006, BPH has infested nearly 65,000 hectares in 16 provinces, 335,000 ton shortfall. By Nov. 5, 2006, BPH and RRSV had spread to 21 provinces, affecting greater than 500,000 ha rice with losses totaling an estimated US $125 M. By Dec. 6, 2006, HPAI was re-introduced into Vietnam by, it is believed, smuggled birds. By Mar. 1, 2007, unvaccinated birds found dead, H5N1 positive. They had been taken from an area of HPAI outbreak to Soc Trang to feed in recently harvested rice fields. By Mar. 12, 2007, H5N1 determined to be Chinese strain. Vietnam lifted a 2005 ban on raising ducks and geese; 60 million waterfowl in the country used for reducing feed costs and pest epidemics. Over 100,000 birds were destroyed in 16 provinces; in 2006-2007, 12 infected humans, 9 fatalities in Vietnam. In summary, it was concluded that the present system could detect the interrelatedness between plant health and animal and human health.

Example 13

Nuclear Events

The system 200 was used to conduct retrospective case studies of radiological incidents in Meet Haifa, Egypt; Lilo, Ga.; Jilin, China; Tammiku, Estonia; AQ Khan; and Samut Prakarn, Thailand, to identify potential I&Ws of radiological events. These case studies encompassed time periods from 1960-2001. I&Ws derived from case studies have been used to populate a taxonomy capable of detecting nuclear and radiological events; however, to date, the system 200 has not been used prospectively to identify nuclear events.

Example 14

Biological Weapon Events

The system 200 is estimated to be useful for the detection of covert state and non-state biological weapons programs. The goal of this research has been to build a taxonomy that may be capable of alerting analysts to social disruption I&Ws suspicious for covert biological weapons research; however, to date, the system 200 has not been used prospectively to identify such events.

The former covert Dugway Biological Weapons program was manually examined retrospectively to examine four discrete events conducted by the Desert test center in order to refine the Dugway analysis: (1) Project "Red Cloud" [Fort Greeley, Ak., November 1966-February 1987]; (2) Project "Watch Dog" [Fort Greeley, Ak., Summer 1967; (3) Project "Green Mist" [Island of Hawaii, Mar. 25-Apr. 24, 1967]; and (4) Project "Blue Tango" [Island of Hawaii, January-March, 1968]. Media articles related from surrounding areas were collected and it was determined that the data collection yielded few I&Ws for those events.

The World War II Biological Weapons deployments of Japanese Unit 731 in Congshan region of Manchura, PRC, was examined retrospectively. Multiple materials related to Unit 731 activities in Manchuria during WWII were collected. Because Unit 731 attempted multiple biowarfare attacks on Manchuria during the WWII time period, just the Ningbo plague drop in 1940 was examined Since most of the Chinese media articles collected at the various libraries were illegible, two specific materials identified during the collection phase were used: (1) "Japanese Biological Warfare One Family's Encounter," by Archie Crouch; and (2) *Chugokugawashiryo: Chugokushinryaku to nanasanichi butai no saikinsen*, a book that compiled Chinese media articles documenting the plague outbreak during the same time period in Ningbo. Those documents were chosen because they provide two different perspectives of the plague drop: one family's personal experience versus media reporting of the event.

The materials were manually evaluated for reports of biological I&Ws, as well as for reports of the social disruption that accompanied the plague drop. In addition, both materials were examined for possible new I&Ws related to covert biological warfare programs. Finally, the materials were manually examined for possible discrepancies in reporting. That information is estimated to be useful in developing a Biological Warfare taxonomy.

The events involving the Aum Shinrykyo program in Japan, the Rajneeshee program in The Dalles, Oreg., and anthrax in Rhodesia and Namibia events have also been manually and retrospectively examined.

Example 15

Dread Threat Taxonomic Development

A dread threat study of specific biological and non-biological threats in order to develop the theoretical foundation of social disruption theory is known. Slovic et al. originally defined dread risk as the degree to which a technology or activity is perceived to be uncontrollable, dread, catastrophic, hard to prevent, fatal, inequitable, affecting future generations, not easily reduced, increasing, involuntary, and personally threatening (Slovik, et al 2000). Through the study of the 1992 cholera epidemic in Venezuela, the 1997-98 outbreak of Rift Valley fever in Kenya, the 1995 outbreak of VEE, and 1802-2003 outbreak of SARS in China, the local responses to infectious disease outbreaks was evaluated, showing particularly how a local population's sense of an emerging dread threat varies over time.

With this background, examination of other types of threats were undertaken, beginning with a detailed analysis of the Japanese attack of Ningbo, China during the Sino-Japanese War using a bomb containing plague-infested fleas. Through detailed, line-by-line analysis of Japanese Biological Warfare in China: One Family's Encounter by Archie Crouch, a new concept of "menacing context" was developed. The analysis suggests that a menacing context has emerged when a dread threat persists and requires a community to reorganize its life to help mitigate consequences of threat. This concept has applications to the study of other threats, including drought and crop failure, industrial accidents and internecine strife.

Example 16

A/H3N2 (1968)

The system 200 was used in a retrospective study to assess whether I&Ws of the A/H1N1 pandemic influenza in Hong Kong and Southern China (1968) could have been detectable prior to others reporting about the influenza. The study involved developing an I&W taxonomy of pandemic influenza, monitoring media sources for markers of social disruption indicative of anomalous respiratory disease/influenza activity, and then identify a pandemic I&W signature, which could be used to compare the seasonal year (i.e., 1968) with a prior known seasonal period (i.e., 1967).

Development of an infectious disease taxonomy included selecting highly disruptive historical biological events, collected articles from news media archives that directly or indirectly referenced the selected event, and validated the taxonomy by conducting a series of case studies. It was found that I&Ws were present in media reports prior to statements of action from the international public health community, and I&Ws increased in volume and diversified in type as the event progressed.

Development of a pandemic influenza taxonomy included collecting articles from news media archives that directly or indirectly referenced the event (e.g., 1968 pandemic influenza in Hong Kong and Southern China), identifying the societal response to disease baselines during seasonal and pandemic years, and applying the retrospective pandemic influenza taxonomy to the collected relevant articles. The resulting pandemic influenza taxonomy included 93 parameters, including direct I&Ws (one main category) and indirect I&Ws (six main categories), all of which are regional, cultural, and disease-specific. The categories are shown in Table 7 below.

TABLE 7

| Main Pandemic Taxonomic Category | Definition |
|---|---|
| Report of Human Disease | Media reports of illness of a known or unknown disease entity at a uni-focal or multi-focal level. |
| Official Acknowledgement | Media reports of acceptance or denial of disease from an official source and/or type of reporting. |
| Community Acknowledgement | Media reports of acceptance or denial of disease by a person with accreditation less than an official, but more than locals. |
| Official Action | Media reports of implementation of countermeasures, biosurveillance, health alerts, official investigations, and changes to current policies and procedures by authorities at local, national and/or international levels. |
| Integrity of Infrastructure | Media reports of compromise or collapse of a society. |
| Local Perception of Threat | Media reports of periods of heightened anxiety and public concern within a society. |
| Business Practice Changes | Media reports of changes in the economic markets. |

In terms of article collection, the system 200 was applied in a target region (Hong Kong/Southern China). Approximately 120 source-months of articles from 1967-1968 were included (accessed at the Library of Congress and Georgetown University Library), including one Chinese-language source and four English-language sources. I&W Main Category Comparison. All indicators increased in 1968 compared to 1967. The greatest increases were noted in the following main taxonomic categories: report of human disease: 23-fold increase; local perception of threat: 15-fold increase; official action: 9-fold increase; individual newspaper articles were more informative in a pandemic year; pandemic year: 1-15 indicators per article; seasonal year: 1-5 indicators per article. All indicators increased at least 15-fold in July 1968 compared to July 1967. Business practice changes was the only exception. Statistically, the overall crude number of taxonomy indicators saw a 7.2-fold increase in pandemic over seasonal year (1968; n=553) versus (1967; n=77) (p=0.004), and the month of A/H3N2 emergence (July 1968) saw a 42.3-fold increase compared to July 1967 (1968; n=254) versus (1967; n=6) (p=0.008).

In summary, the system 200 was used to develop and apply a methodology that converts qualitative information into quantitative and potentially actionable information. The taxonomy-based media surveillance approach according to the present invention is viewed as enabling early detection and situational awareness of an anomalous influenza season. The number of disease indicators per article appeared to increase in the pandemic year compared to the seasonal year in Hong Kong/Southern China. A distinct time-varying signature of indicators appeared to differentiate between pandemic and seasonal influenza years in Hong Kong/Southern China. Georgetown University has applied this methodology, to some degree, using real-time electronically captured media throughout the 2009-A/H1N1 pandemic influenza, as discussed in the next example.

Example 17

A/H1N1 (2009)

The system 200 was used to identify I&Ws of the current A/H1N1 pandemic influenza and the results were compared to reports by other publicly-available media sources, such as HealthMap. Reports of respiratory disease for the 2007-2008 and 2008-2009 respiratory disease seasons were generated from relevant information sources in the form of media articles previously archived by the system 200 as previously discussed. Reports of respiratory disease, including 2009 A/H1N1, in the Spanish and English media in Mexico between Oct. 1, 2007 and May 31, 2009 were reviewed. The rate of reporting defined as a function of time for the study period utilized the ratio of respiratory reports meeting inclusion criteria to the total articles in the archive from Mexican sources. A Shapiro-Wilk test was used to assess the normality of the data. A Wilcoxon rank sum test was used to assess the statistical significance of the difference in mean rate of respiratory disease reporting and stage between seasons.

The results showed an increased prominence of respiratory disease reporting frequency in Mexican Internet sources during the 2008-2009 influenza season relative to 2007-2008. Mean rate of reporting: Oct. 1, 2007 and May 31, 2008 (rate=2.19); Oct. 1, 2008 and May 31, 2009 (rate=4.08) (p<0.0001). Stage of reporting: Oct. 1, 2007 and May 31, 2008 (stage 2 and occasionally stage 3; mean stage=2.35); Oct. 1, 2008 and May 31, 2009 (staged at 2 or less; mean stage=1.80) (p-value<0.0001).

Based on these results, the system 200 found an increased prominence of respiratory disease reporting frequency in Mexican Internet sources during the 2008-2009 influenza season relative to 2007-2008. The stage of respiratory disease reports in the media in the 2008-09 season scored significantly higher in terms of social disruption than reports in the media in the 2007-08 season. The respiratory disease was prevalent in parts of Mexico, and reported as unusual, much earlier than the microbiological recognition of influenza A/H1N1 in late April, 2009. Increased reporting frequency, longer duration of the respiratory season and significantly increased stage (social disruption) together may indicate an anomalous season. Through the analysis of data over time, media reporting baselines can be generated and media signals of anomalous activity identified by the system and method of the present invention, providing clues to emerging outbreaks. The present event-based surveillance tool is complementary to traditional public health surveillance methods utilized to identify an outbreak and track its progression and can cue public health professionals to look for an emerging or changing pathogen earlier than would otherwise be known, and it can provide an effective means for monitoring the spread of disease and severity in a population or region.

Although certain presently preferred embodiments of the disclosed invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims, prior art, and applicable rules of law.

We claim:

1. A computer implemented method for filtering open source documents to detect events, the method comprising:
    storing, at a first server, indications and warnings associated with each of a plurality of event types, each of the event types being related to a disease or pest infestation affecting a plant or non-human animal;
    receiving a selection of an event type;
    receiving a selection of a surveillance location;

identifying information sources that may have data about the selected event type;

downloading publicly accessible data from the selected information sources;

filtering the data, using an alert generation module developed using Bayesian causal models, to identify a subset of the data containing indications and warnings that suggest that the disease or pest infestation is occurring;

creating and storing an event report identifying the disease or pest infestation based on the subset of the publicly accessible data containing the indications and warnings; and outputting the event report over a communications network.

2. The method according to claim 1, wherein the surveillance location is one of a town, city, region, and country.

3. The method according to claim 1, wherein the information sources are web servers connected to the Internet.

4. The method according to claim 1, wherein the indications and warnings are individual or combinations of keywords.

5. The method according to claim 1, wherein the step of downloading data from the selected information sources comprises the steps of:

crawling the information sources;
encoding the data; and
storing the encoded data in a first database.

6. The method according to claim 5, further comprising the step of indexing the encoded data.

7. The method according to claim 1, further comprising the step of translating the data from a first language into a second language.

8. The method according to claim 1, further comprising assigning a scale value to the subset of the data indicating a degree of the event.

9. The method according to claim 8, wherein the scale value comprises an indicia selected from one of a word, a phrase, and a color.

10. The method according to claim 8, wherein the scale value is selected from one of an Advisory, a Watch, and a Warning.

11. The method according to claim 1, wherein the step of storing the event report comprises the steps of:

launching a template;
selecting metadata from a stored list of possible metadata;
if an event report exists, updating the existing event report using some of the subset of the data and the metadata; and
if an event report does not exist, storing a first summary of the event using some of the subset of the data and the metadata in an event report file.

12. The method according to claim 1, wherein the step of filtering comprises the steps of:

receiving a query search string;
comparing the query search string to an index; and
returning a list comprising the subset of the data using the query search string.

13. A system for filtering open source documents to detect events, comprising:

one or more document collection servers that download and store publicly accessible data from information sources;

a first server that stores indications and warnings associated with each of a plurality event types, each of the event types being related to a disease or pest infestation affecting a plant or non-human animal;

a graphical user interface that receives a selection of an event type and a selection of a surveillance location;

an alert generation module developed using Bayesian causal models that identifies a subset of the publicly accessible data containing indications and warnings that suggest that the disease or pest infestation is occurring;

an analysis and reporting subsystem that creates and outputs an event report identifying the disease or pest infestation based on the subset of the publicly accessible data containing the indications and warnings.

14. The system according to claim 13, wherein the surveillance location is one of a town, city, region, and country.

15. The system according to claim 13, wherein the information sources are web servers connected to the Internet.

16. The system according to claim 13, wherein the indications and warnings are individual or combinations of keywords.

17. The system according to claim 13, wherein the server downloads data from the information sources by:

crawling the information sources;
encoding the data; and
storing the encoded data in a first database.

18. The system according to claim 17, wherein the server indexes the encoded data.

19. The system according to claim 13, wherein the system translates the data from a first language into a second language.

20. The system according to claim 13, wherein the system assigns a scale value to the subset of the data indicating a degree of the event.

21. The system according to claim 20, wherein the scale value comprises an indicia selected from one of a word, a phrase, and a color.

22. The system according to claim 20, wherein the scale value is selected from one of an Advisory, a Watch, and a Warning.

23. The system according to claim 13, wherein the analysis and reporting subsystem creates the event report by:

launching a template;
selecting metadata from a stored list of possible metadata;
if an event report exists, updating the existing event report using some of the subset of the data and the metadata; and
if an event report does not exist, storing a first summary of the event using some of the subset of the data and the metadata in an event report file.

24. The system according to claim 13, wherein the alert generation module identifies the subset of the publicly accessible data containing indications and warnings that suggest that the disease or pest infestation is occurring by:

receiving a query search string;
comparing the query search string to an index; and
returning a list comprising the subset of the data using the query search string.

* * * * *